US012391958B2

(12) United States Patent
Schneider et al.

(10) Patent No.: US 12,391,958 B2
(45) Date of Patent: Aug. 19, 2025

(54) COMPOSITIONS AND METHODS FOR TREATING CANCER WITH ANTI-CD38 IMMUNOTHERAPY

(71) Applicants: Lentigen Technology, Inc., Gaithersburg, MD (US); The U.S.A., as represented by the Secretary, Department of Health and Human Services, Bethesda, MD (US)

(72) Inventors: Dina Schneider, Potomac, MD (US); Rimas J. Orentas, Seattle, WA (US); Boro Dropulic, Ellicott City, MD (US); Dimiter S. Dimitrov, Frederick, MD (US); Zhongyu Zhu, Frederick, MD (US)

(73) Assignees: Lentigen Technology, Inc., Gaithersburg, MD (US); The U.S.A., as represented by The Secretary, Department of Health and Human Services, Bethesda, MD (US)

(*) Notice: Subject to any disclaimer, the term of this patent is extended or adjusted under 35 U.S.C. 154(b) by 1094 days.

(21) Appl. No.: 17/331,733

(22) Filed: May 27, 2021

(65) Prior Publication Data

US 2021/0353675 A1 Nov. 18, 2021

Related U.S. Application Data

(62) Division of application No. 16/698,186, filed on Nov. 27, 2019, now Pat. No. 11,103,533.

(60) Provisional application No. 62/773,940, filed on Nov. 30, 2018.

(51) Int. Cl.

| | |
|---|---|
| ***C12N 15/85*** | (2006.01) |
| ***A61K 35/17*** | (2025.01) |
| ***A61K 39/00*** | (2006.01) |
| ***A61K 40/11*** | (2025.01) |
| ***A61K 40/31*** | (2025.01) |
| ***A61K 40/42*** | (2025.01) |
| ***A61P 35/02*** | (2006.01) |
| ***C07K 14/705*** | (2006.01) |
| ***C07K 16/28*** | (2006.01) |
| ***C12N 5/0783*** | (2010.01) |
| ***C12N 15/86*** | (2006.01) |

(52) U.S. Cl.

CPC .............. *C12N 15/86* (2013.01); *A61K 40/11* (2025.01); *A61K 40/31* (2025.01); *A61K 40/4222* (2025.01); *A61P 35/02* (2018.01); *C07K 16/2896* (2013.01); *C12N 5/0636* (2013.01); *A61K 2239/48* (2023.05)

(58) Field of Classification Search

None

See application file for complete search history.

(56) References Cited

U.S. PATENT DOCUMENTS

| | | | |
|---|---|---|---|
| 11,103,533 | B2 | 8/2021 | Schneider et al. |
| 2020/0197440 | A1 | 6/2020 | Schneider et al. |

FOREIGN PATENT DOCUMENTS

| | | |
|---|---|---|
| CN | 108495641 A | 9/2018 |
| WO | WO 2015121454 | 8/2015 |
| WO | WO 2017025323 | 2/2017 |

OTHER PUBLICATIONS

Malavasi ct al., "CD38 and chronic lymphocytic leukemia: a decade later." Blood, The Joamal of the American Society of Hematology, Sentember 29, 2011, 118(13):3470-3478.*

Xiao et al., mRNA-based chimeric antigen receptor T cell therapy: Basic principles, recent advances and future directions, Interdiscip. Med. 2024, pp. 1-15.*

Drent et al., "Pre-clinical evaluation of CD38 chimeric antigen receptor engineered T cells for the treatment of multiple myeloma," Haematologica, May 2016, 101(5):616-25.

Zhang et al., "Research Progress of Chimeric Antigen Receptor T Cell Therapy in Multiple Myeloma," Chinese Journal of Cellular and Molecular Immunology, 2018 vol. 34(5):469, 2 pages (English abstract only).

Drent et al., "A rational strategy for reducing on-target off-tumor effects of CD38-chimeric antigen receptors by affinity optimization," Mol. Ther., 2017, 25(8):1946-1958.

Malavasi et al., "CD38 and chronic lymphocytic leukemia: a decade later," Blood, The Journal of the American Society of Hematology, Sep. 29, 2011, 118(13):3470-3478.

Mihara et al., "Activated T-cell-mediated immunotherapy with a chimeric receptor against CD38 in B-cell non-Hodgkin lymphoma," J. Immunother., 2009, 32(7):737-743.

Mirzaei et al., "Chimeric antigen receptors T cell therapy in solid tumor: challenges and clinical applications," Frontiers in Immunology, 2017, pp. 1-13.

Morandi et al., "CD38: a target for immunotherapeutic approaches in multiple myeloma," Frontiers in Immunology, 2018, 9:2722, 9 pages.

Newick et al., "Chimeric antigen receptor T-cell therapy for solid tumors," Mol. Ther.—Oncolytics, 2016. 3:1-7.

(Continued)

*Primary Examiner* — Maria Marvich

(74) *Attorney, Agent, or Firm* — Serge Sira, Esq.; Gregory J. Hwa, Esq.; Fish & Richardson P.C.

(57) ABSTRACT

Chimeric antigen receptors containing CD38 antigen binding domains are disclosed. Nucleic acids, recombinant expression vectors, host cells, antigen binding fragments, and pharmaceutical compositions, relating to the chimeric antigen receptors are also disclosed. Methods of treating or preventing cancer in a subject, and methods of making chimeric antigen receptor T cells are also disclosed.

21 Claims, 5 Drawing Sheets

Specification includes a Sequence Listing.

(56) References Cited

OTHER PUBLICATIONS

PCT International Preliminary Report on Patentability in International Application. No. PCT/US2019/063761, dated Jun. 10, 2021, 10 pages.
PCT International Search Report and Written Opinion in PCT Application. No. PCT/US2019/063761, dated Mar. 30, 2020, 16 pages.
Yoshida et al., "All-trans retinoic acid enhances cytotoxic effect of T cells with an anti-CD38 chimeric antigen receptor in acute myeloid leukemia," Clinical & Translational Immunology, 2016, 5(12):e116.

* cited by examiner hScFv aCD38 | CD8 TM | CD137 | CD3z

FIGURE 1

COMPOSITIONS AND METHODS FOR TREATING CANCER WITH ANTI-CD38 IMMUNOTHERAPY

CROSS-REFERENCE TO RELATED APPLICATIONS

This application is a divisional of U.S. patent application Ser. No. 16/698,186 (now U.S. Pat. No. 11,103,533), filed on Nov. 27, 2019, which claims the benefit of priority under 35 U.S.C. Section 119(e) to U.S. Provisional Patent Application No. 62/773,940, filed on Nov. 30, 2018, the entire contents of which are incorporated herein by reference.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. The Government of the United States has certain rights in this invention.

SEQUENCE LISTING

The instant application contains a Sequence Listing which has been submitted electronically in ASCII format and is hereby incorporated by reference in its entirety. Said ASCII copy, created on May 25, 2021, is named Sequence_Listing and is 192,512 bytes in size.

FIELD OF THE DISCLOSURE

This application relates to the field of cancer, particularly to CD38 antigen binding domains and chimeric antigen receptors (CARs) containing such CD38 antigen binding domains and methods of use thereof.

BACKGROUND

Cancer is one of the most deadly threats to human health. In the U.S. alone, cancer affects nearly 1.3 million new patients each year, and is the second leading cause of death after cardiovascular disease, accounting for approximately 1 in 4 deaths. Solid tumors are responsible for most of those deaths. Although there have been significant advances in the medical treatment of certain cancers, the overall 5-year survival rate for all cancers has improved only by about 10% in the past 20 years. Cancers. or malignant tumors, metastasize and grow rapidly in an uncontrolled manner, making treatment extremely difficult.

Multiple myeloma ("MM") is a debilitating and often incurable disease, with over 30,000 new cases diagnosed in the U.S. every year (source: MM research foundation). MM is the second most prevalent blood cancer in the U.S., after Non-Hodgkin's Lymphoma ("NHL"), (Smith L, McCourt O, Henrich M, et al. Multiple myeloma and physical activity: a scoping review. BMJ Open. 2015; 5: e009576). MM impacts plasma cells in the bone marrow, and may lead to bone marrow failure and patient death (National Cancer Institute. A snapshot of myeloma. Nov. 5, 2014. see the world wide web at cancer.gov). Complications of myeloma include bone pain, bone loss, anemia, immunosuppression, kidney disfunction, neuropathy (Mayo Clinic staff. Diseases and conditions: multiple myeloma: treatments and drugs. Dec. 4, 2015).

First line therapy for MM includes proteasome inhibitors, immunomodulatory drugs, steroids, histone deacetylase ("HDAC") inhibitors, and chemotherapy. These approaches are aimed at killing MM cells, however, many of them are also associated with broad immunosuppression and systemic toxicities.

Immunotherapy approaches to MM include the FDA-approved monoclonal antibodies Empliciti (elotuzumab, targets SLAMF7) and Darzalex (daratumumab, targets CD38). In addition, checkpoint inhibitors are being evaluated in clinical trials for MM patients. Despite the abundance of treatment options, the survival rate for patients with advanced stages of MM is only 83 months for stage II MM, and 43 month for stage III (American Cancer Society, see the world wide web at cancer.org). Therefore, better therapeutic modalities are urgently needed for MM and other $CD38^+$ malignancies.

Like MM, B-cell chronic lymphocytic leukemia ("CLL") is another difficult-to-treat malignancy. CLL is a lymphoproliferative disease with variable survival prognosis, ranging from months to decades. The disease impacts mainly the elderly, with median time of onset over 65 years of age. However, despite the advanced onset age, CLL diagnosis tends to shorten patients' life expectancy (Shanafelt, Tait. "Treatment of older patients with chronic lymphocytic leukemia: key questions and current answers." ASH Education Program Book 2013.1 (2013): 158-167.). The rate of disease progression is typically dependent on the type of BCR mutations present (Dighiero, Guillaume. "CLL biology and prognosis." ASH Education Program Book 2005.1 (2005): 278-284.). Moreover, in CLL, CD38 serves as a marker for unfavorable disease prognosis. CD38 expression in CLL is associated with enhanced leukemic cell proliferation, enhanced migration, and heightened responsiveness to BCR-mediated signaling (Malavasi, Fabio, et al. "CD38 and chronic lymphocytic leukemia: a decade later." Blood (2011): blood-2011). While patients whose prognosis is good may not need to be treated for CLL, it is virtually incurable and early treatment does not improve prognosis. The first line treatment for CLL typically includes a combination of several therapeutic agents, i.e. chemotherapeutics (cyclophosphamide, fludarabine), anti-CD20 antibody Rituximab (Rituxan), BTK inhibitor Ibrutinib, high dose prednisolone, or Alemtuzumab (Campath). Despite the existence of a great array of treatment agents, CLL treatment regiments tend to be aggressive, and toxicities remain a problem. The elderly and co-morbid patients remain especially vulnerable to CLL-treatment-associated toxicities, such as immunosuppression and susceptibility to infections (Barrientos, Jacqueline C. "Management of chronic lymphocytic leukemia in the elderly." Cancer Control 22.4_suppl (2015): 17-23; Smolej, Lukáš. "How I treat elderly or comorbid patients with chronic lymphocytic leukemia." Acta Medica (Hradec Kralove) 53.4 (2010): 213-220).

Due to suboptimal efficacy and toxicities associated with the treatment of CD38-positive malignancies, better treatment options are needed. CAR-based approaches to the treatment of CD38-positive malignancies and CD38-positive tumor microenvironment cells, may provide a much needed therapeutic option for patients who are unable to tolerate the toxicity associated with the conventional first line therapies. Moreover, CAR T approaches are expected to lack the non-selective, and often irreversible toxicity associated with chemotherapy, or chemo/immunotherapy combinations. Moreover, a CAR T cells is a "living drug," and thus is expected to remain in the body of the patient for an extended period of time or indefinitely, providing long-term therapeutic effect. These characteristics of CAR T cells are postulated to obviate the need for repeat treatments, and reduce the probability of the disease's relapse.

CAR approaches targeting CD38 are superior to chemotherapy because they may achieve better efficacy in eliminating CD38$^+$ tumor cells and tumor stem cells, and because they avoid the toxicities associated with chemotherapy. Importantly, CAR T cells are expected to be more efficient than chemotherapy in eliminating minimal residual disease, resulting in better long-term treatment prognosis. Furthermore, CAR T cells targeting CD38 ("CAR38") may be used for tumor debulking as a bridge to transplant, as may help patient with high tumor burden become eligible for BMT.

CAR38 represents an improvement over prior art because unique human ScFv (hereinafter "hScFv") sequences are used in the CAR design, as opposed to murine-derived ScFvs employed in CAR designs elsewhere. Mouse-derived sequences carry the risk of immunogenicity, and may induce allergic or anaphylactic responses in patients, leading to CAR T elimination, or life-threatening anaphylaxis.

Chimeric Antigen Receptors (CARs) are hybrid molecules comprising three essential units: (1) an extracellular antigen-binding motif, (2) linking/transmembrane motifs, and (3) intracellular T-cell signaling motifs (Long A H, Haso W M, Orentas R J. Lessons learned from a highly-active CD22-specific chimeric antigen receptor. Oncoimmunology. 2013; 2 (4):e23621). The antigen-binding motif of a CAR is commonly fashioned after an single chain Fragment variable (ScFv), the minimal binding domain of an immunoglobulin (Ig) molecule. Alternate antigen-binding motifs, such as receptor ligands (i.e., IL-13 has been engineered to bind tumor expressed IL-13 receptor), intact immune receptors, library-derived peptides, and innate immune system effector molecules (such as NKG2D) also have been engineered. Alternate cell targets for CAR expression (such as NK or gamma-delta T cells) are also under development (Brown C E et al. Clin Cancer Res. 2012; 18(8):2199-209; Lehner M et al. PLoS One. 2012; 7 (2):e31210). There remains significant work with regard to defining the most active T-cell population to transduce with CAR vectors, determining the optimal culture and expansion techniques, and defining the molecular details of the CAR protein structure itself.

The linking motifs of a CAR can be a relatively stable structural domain, such as the constant domain of IgG, or designed to be an extended flexible linker. Structural motifs, such as those derived from IgG constant domains, can be used to extend the ScFv binding domain away from the T-cell plasma membrane surface. This may be important for some tumor targets where the binding domain is particularly close to the tumor cell surface membrane (such as for the disialoganglioside GD2; Orentas et al., unpublished observations). To date, the signaling motifs used in CARs always include the CD3-ζ chain because this core motif is the key signal for T cell activation. The first reported second-generation CARs featured CD28 signaling domains and the CD28 transmembrane sequence. This motif was used in third-generation CARs containing CD137 (4-1BB) signaling motifs as well (Zhao Y et al. J Immunol. 2009; 183 (9): 5563-74). With the advent of new technology, the activation of T cells with beads linked to anti-CD3 and anti-CD28 antibody, and the presence of the canonical "signal 2" from CD28 was no longer required to be encoded by the CAR itself. Using bead activation, third-generation vectors were found to be not superior to second-generation vectors in in vitro assays, and they provided no clear benefit over second-generation vectors in mouse models of leukemia (Haso W, Lee D W, Shah N N, Stetler-Stevenson M, Yuan C M, Pastan I H, Dimitrov D S, Morgan R A, FitzGerald D J, Barrett D M, Wayne A S, Mackall C L, Orentas R J. Anti-CD22-chimeric antigen receptors targeting B cell precursor acute lymphoblastic leukemia, Blood. 2013; 121 (7):1165-74; Kochenderfer J N et al. Blood. 2012; 119 (12):2709-20). This is borne out by the clinical success of CD19-specific CARs that are in a second generation CD28/CD3-ζ (Lee D W et al. American Society of Hematology Annual Meeting. New Orleans, LA; Dec. 7-10, 2013) and a CD137/CD3-ζ signaling format (Porter D L et al. N Engl J Med. 2011; 365 (8): 725-33). In addition to CD137, other tumor necrosis factor receptor superfamily members such as OX40 also are able to provide important persistence signals in CAR-transduced T cells (Yvon E et al. Clin Cancer Res. 2009; 15(18):5852-60). Equally important are the culture conditions under which the CAR T-cell populations were cultured.

T-cell-based immunotherapy has become a new frontier in synthetic biology; multiple promoters and gene products are envisioned to steer these highly potent cells to the tumor microenvironment, where T cells can both evade negative regulatory signals and mediate effective tumor killing. The elimination of unwanted T cells through the drug-induced dimerization of inducible caspase 9 constructs with AP1903 demonstrates one way in which a powerful switch that can control T-cell populations can be initiated pharmacologically (Di Stasi A et al. N Engl J Med. 2011; 365(18):1673-83). The creation of effector T-cell populations that are immune to the negative regulatory effects of transforming growth factor-O by the expression of a decoy receptor further demonstrates that degree to which effector T cells can be engineered for optimal antitumor activity (Foster A E et al. J Immunother. 2008; 31(5):500-5). Thus, while it appears that CARs can trigger T-cell activation in a manner similar to an endogenous T-cell receptor, a major impediment to the clinical application of this technology to date has been limited in vivo expansion of CAR$^+$ T cells, rapid disappearance of the cells after infusion, and disappointing clinical activity. Accordingly, there is an urgent and long felt need in the art for discovering novel compositions and methods for treatment of MM and CLL using an approach that can exhibit specific and efficacious anti-tumor effect without the aforementioned shortcomings (i.e. high toxicity, insufficient efficacy).

The present invention addresses these needs by providing CAR compositions and therapeutic methods that can be used to treat cancers and other diseases and/or conditions. In particular, the present invention as disclosed and described herein provides CARs that may be used for the treatment of diseases, disorders or conditions associated with dysregulated expression of CD38 and which CARs contain CD38 antigen binding domains that exhibit a high surface expression on transduced T cells, exhibit a high degree of cytolysis and transduced T cell in vivo expansion and persistence.

SUMMARY

Novel anti-CD38 antibodies or antigen binding domains thereof and chimeric antigen receptors (CARs) that contain such CD38 antigen binding domains are provided herein, as well as host cells (e.g., T cells) expressing the receptors, and nucleic acid molecules encoding the receptors. CAR may consist either of a single molecule expressed on the effector cell surface, or a CAR comprised of an effector cell-expressed signaling module and a soluble targeting module, such as when the soluble targeting module binds to the cell-expressed signaling module, a complete functional CAR is formed. The CARs exhibit a high surface expression on transduced T cells, with a high degree of cytolysis and transduced T cell expansion and persistence in vivo. Methods of using the disclosed CARs, host cells, and nucleic acid molecules are also provided, for example, to treat a cancer in a subject.

Thus, in one aspect, an isolated polynucleotide encoding a human anti-CD38 antibody or a fragment thereof is provided comprising a nucleic acid sequence selected from the group consisting of SEQ ID NOs: 1, 3, 5, 7, 9, 11, 15, 17, 19, 21, 23, 25, 69, 71, 73, and 75.

In one embodiment, an isolated polynucleotide encoding a fully human anti-CD38 antibody or a fragment thereof is provided, wherein the antibody or a fragment thereof comprises a fragment selected from the group consisting of an Fab fragment, an $F(ab')_2$ fragment, an Fv fragment, and a single chain Fv (ScFv).

In one embodiment, an isolated polynucleotide encoding a fully human anti-CD38 antibody or a fragment thereof is provided, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, and 76.

In one aspect, an isolated nucleic acid molecule encoding a chimeric antigen receptor (CAR) is provided comprising, from N-terminus to C-terminus, at least one CD38 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 73, and 75, at least one transmembrane domain, and at least one intracellular signaling domain.

In one embodiment, an isolated nucleic acid molecule encoding the CAR is provided wherein the encoded extracellular CD38 antigen binding domain comprises at least one single chain variable fragment of an antibody that binds to CD38.

In another embodiment, an isolated nucleic acid molecule encoding the CAR is provided wherein the encoded extracellular CD38 antigen binding domain comprises at least one heavy chain variable region of an antibody that binds to CD38.

In one embodiment, the targeting domain of the CAR is expressed separately in the form of monoclonal antibody, ScFv Fab, Fab'2 and is containing an antigen-targeting domain comprising a nucleic acid sequence selected from the group consisting of SEQ ID NOs: 1, 3, 5, 7, 9, 11, 15, 17, 19, 21, 23, 25, 69, 71, 73, and 75 coupled to an additional binding tag or epitope, whereas the effector-cell expressed component of the CAR contains a binding domain specifically directed to bind the tag or epitope expressed on the soluble CAR module, such as specific binding on the soluble component of the CAR to the cell bound component of the CAR forms the full functional CAR structure.

In another embodiment, the targeting domain of the CAR is expressed separately in the form of a monoclonal antibody, ScFv Fab, Fab'2 and contains an antigen-targeting domain comprising a nucleic acid sequence selected from the group consisting of SEQ ID NOs: 1, 3, 5, 7, 9, 11, 15, 17, 19, 21, 23, 25, 69, 71, 73, and 75, and an additional ScFv, whereas the effector-cell expressed component of the CAR contains a tag or epitope specifically reactive with the additional ScFv expressed on the soluble CAR module, such as specific binding on the soluble component of the CAR to the cell bound component of the CAR forms the full functional CAR structure.

In yet another embodiment, an isolated nucleic acid molecule encoding the CAR is provided wherein the encoded CAR extracellular CD38 antigen binding domain further comprises at least one lipocalin-based antigen binding antigen (anticalins) that binds to CD38.

In one embodiment, an isolated nucleic acid molecule is provided wherein the encoded extracellular CD38 antigen binding domain is connected to the transmembrane domain by a linker domain.

In another embodiment, an isolated nucleic acid molecule encoding the CAR is provided wherein the encoded CD38 extracellular antigen binding domain is preceded by a sequence encoding a leader or signal peptide.

In yet another embodiment, an isolated nucleic acid molecule encoding the CAR is provided comprising at least one CD38 antigen binding domain encoded by a nucleotide sequence comprising a nucleic acid sequence selected from the group consisting of SEQ ID NOs: 1, 3, 5, 7, 9, 11, 15, 17, 19, 21, 23, 25, 69, 71, 73, and 75, and wherein the CAR additionally encodes an extracellular antigen binding domain targets an antigen that includes, but is not limited to, CD19, CD20, CD22, ROR1, mesothelin, CD33, CD38, CD138, BCMA (CD269), GPC2, GPC3, FGFR4, c-Met, PSMA, Glycolipid F77, EGFRvIII, GD-2, NY-ESO-1 TCR, MAGE A3 TCR, or any combination thereof.

In certain embodiments, an isolated nucleic acid molecule encoding the CAR is provided wherein the additionally encoded extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In one aspect, the CARs provided herein further comprise a linker or spacer domain.

In one embodiment, an isolated nucleic acid molecule encoding the CAR is provided wherein the extracellular CD38 antigen binding domain, the intracellular signaling domain, or both are connected to the transmembrane domain by a linker or spacer domain.

In one embodiment, an isolated nucleic acid molecule encoding the CAR is provided wherein the encoded linker domain is derived from the extracellular domain of CD8 or CD28, and is linked to a transmembrane domain.

In another embodiment, an isolated nucleic acid molecule encoding the CAR is provided wherein the encoded CAR further comprises a transmembrane domain that comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In yet another embodiment, an isolated nucleic acid molecule encoding the CAR is provided wherein the encoded intracellular signaling domain further comprises a CD3 zeta intracellular domain.

In one embodiment, an isolated nucleic acid molecule encoding the CAR is provided wherein the encoded intracellular signaling domain is arranged on a C-terminal side relative to the CD3 zeta intracellular domain.

In another embodiment, an isolated nucleic acid molecule encoding the CAR is provided wherein the encoded at least one intracellular signaling domain comprises a costimulatory domain, a primary signaling domain, or a combination thereof.

In further embodiments, an isolated nucleic acid molecule encoding the CAR is provided wherein the encoded at least one costimulatory domain comprises a functional signaling domain of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, an isolated nucleic acid molecule encoding the CAR is provided that further contains a leader sequence or signal peptide wherein the leader or signal peptide nucleotide sequence comprises the nucleotide sequence of SEQ ID NO: 13, SEQ ID NO: 39, SEQ ID NO: 41, or SEQ ID NO: 43.

In yet another embodiment, an isolated nucleic acid molecule encoding the CAR is provided wherein the encoded leader sequence comprises the amino acid sequence of SEQ ID NO: 14 SEQ ID NO: 40, SEQ ID NO: 42, or SEQ ID NO: 44.

In one aspect, a chimeric antigen receptor (CAR) is provided herein comprising, from N-terminus to C-terminus, at least one CD38 antigen binding domain, at least one transmembrane domain, and at least one intracellular signaling domain.

In one embodiment, a CAR is provided wherein the extracellular CD38 antigen binding domain comprises at least one single chain variable fragment of an antibody that binds to the antigen, or at least one heavy chain variable region of an antibody that binds to the antigen, or a combination thereof.

In another embodiment, a CAR is provided wherein the at least one transmembrane domain comprises a transmembrane domain of a protein selected from the group consisting of the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and CD154, or a combination thereof.

In some embodiments, the CAR is provided wherein CAR additionally encodes an extracellular antigen binding domain comprising CD19, CD20, CD22, ROR1, mesothelin, CD33, CD38, CD123 (IL3RA), CD138, BCMA (CD269), GPC2, GPC3, FGFR4, c-Met, PSMA, Glycolipid F77, EGFRvIII, GD-2, NY-ESO-1 TCR, MAGE A3 TCR, or an amino acid sequence with 85%, 90%, 95%, 96%, 97%, 98% or 99% identity thereof, or any combination thereof.

In one embodiment, the CAR is provided wherein the extracellular antigen binding domain comprises an anti-CD19 ScFv antigen binding domain, an anti-CD20 ScFv antigen binding domain, an anti-CD22 ScFv antigen binding domain, an anti-ROR1 ScFv antigen binding domain, an anti-mesothelin ScFv antigen binding domain, an anti-CD33 ScFv antigen binding domain, an anti-CD38 ScFv antigen binding domain, an anti-CD123 (IL3RA) ScFv antigen binding domain, an anti-CD138 ScFv antigen binding domain, an anti-BCMA (CD269) ScFv antigen binding domain, an anti-GPC2 ScFv antigen binding domain, an anti-GPC3 ScFv antigen binding domain, an anti-FGFR4 ScFv antigen binding domain, an anti-c-Met ScFv antigen binding domain, an anti-PMSA ScFv antigen binding domain, an anti-glycolipid F77 ScFv antigen binding domain, an anti-EGFRvIII ScFv antigen binding domain, an anti-GD-2 ScFv antigen binding domain, an anti-NY-ESo-1 TCR ScFv antigen binding domain, an anti-MAGE A3 TCR ScFv antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises an immunoglobulin variable heavy chain only (VH) anti-CD19 antigen binding domain, an anti-CD20 VH antigen binding domain, an anti-CD22 VH antigen binding domain, an anti-ROR1 VH antigen binding domain, an anti-mesothelin VH antigen binding domain, an anti-CD33 VH antigen binding domain, an anti-CD38 VH antigen binding domain, an anti-CD123 (IL3RA) VH antigen binding domain, an anti-CD138 VH antigen binding domain, an anti-BCMA (CD269) VH antigen binding domain, an anti-GPC2 VH antigen binding domain, an anti-GPC3 VH antigen binding domain, an anti-FGFR4 VH antigen binding domain, an anti-c-Met VH antigen binding domain, an anti-PMSA VH antigen binding domain, an anti-glycolipid F77 VH antigen binding domain, an anti-EGFRvIII VH antigen binding domain, an anti-GD-2 VH antigen binding domain, an anti-NY-ESO-1 TCR VH antigen binding domain, an anti-MAGE A3 TCR VH antigen binding domain, or an amino acid sequence with 85%, 90%, 95%, 96%, 97%, 98% or 99% identity thereof, or any combination thereof.

In another embodiment, the CAR is provided wherein the extracellular antigen binding domain comprises a protein or a peptide (P) sequence capable of specifically binding target antigen, which may be derived from a natural or a synthetic sequence comprising anti-CD19 P antigen binding domain, an anti-CD20 P antigen binding domain, an anti-CD22 P antigen binding domain, an anti-ROR1 P antigen binding domain, an anti-mesothelin P antigen binding domain, an anti-CD33 P antigen binding domain, an anti-CD38 P antigen binding domain, an anti-CD123 (IL3RA) P antigen binding domain, an anti-CD138 P antigen binding domain, an anti-BCMA (CD269) P antigen binding domain, an anti-GPC2 P antigen binding domain, an anti-GPC3 P antigen binding domain, an anti-FGFR4 P antigen binding domain, an anti-c-Met P antigen binding domain, an anti-PMSA P antigen binding domain, an anti-glycolipid F77 P antigen binding domain, an anti-EGFRvIII P antigen binding domain, an anti-GD-2 P antigen binding domain, an anti-NY-ESO-1 TCR P antigen binding domain, an anti-MAGE A3 TCR P antigen binding domain, or an amino acid sequence with 85%, 90%, 95%, 96%, 97%, 98% or 99% identity thereof, or any combination thereof. In another embodiment, a CAR is provided wherein the at least one intracellular signaling domain comprises a costimulatory domain and a primary signaling domain.

In yet another embodiment, a CAR is provided wherein the at least one intracellular signaling domain comprises a costimulatory domain comprising a functional signaling domain of a protein selected from the group consisting of OX40, CD70, CD27, CD28, CD5, ICAM-1, LFA-1 (CD11a/CD18), ICOS (CD278), DAP10, DAP12, and 4-1BB (CD137), or a combination thereof.

In one embodiment, the nucleic acid sequence encoding a CAR comprises the nucleic acid sequence of SEQ ID NO: 77. In one embodiment, the nucleic acid sequence encodes a CAR comprising the amino acid sequence of SEQ ID NO: 78.

In another embodiment, the nucleic acid sequence encoding a CAR comprises the nucleic acid sequence of SEQ ID NO: 87. In one embodiment, the nucleic acid sequence encodes a CAR comprising the amino acid sequence of SEQ ID NO: 88.

In another embodiment, the nucleic acid sequence encoding a CAR comprises the nucleic acid sequence of SEQ ID NO: 89. In one embodiment, the nucleic acid sequence encodes a CAR comprising the amino acid sequence of SEQ ID NO: 90.

In another embodiment, the nucleic acid sequence encoding a CAR comprises the nucleic acid sequence of SEQ ID NO: 91. In one embodiment, the nucleic acid sequence encodes a CAR comprising the amino acid sequence of SEQ ID NO: 92.

In another embodiment, the nucleic acid sequence encoding a CAR comprises the nucleic acid sequence of SEQ ID NO: 93. In one embodiment, the nucleic acid sequence encodes a CAR comprising the amino acid sequence of SEQ ID NO: 94.

In another embodiment, the nucleic acid sequence encoding a CAR comprises the nucleic acid sequence of SEQ ID NO: 95. In one embodiment, the nucleic acid sequence encodes a CAR comprising the amino acid sequence of SEQ ID NO: 96.

In another embodiment, the nucleic acid sequence encoding a CAR comprises the nucleic acid sequence of SEQ ID NO: 97. In one embodiment, the nucleic acid sequence encodes a CAR comprising the amino acid sequence of SEQ ID NO: 98.

In another embodiment, the nucleic acid sequence encoding a CAR comprises the nucleic acid sequence of SEQ ID NO: 99. In one embodiment, the nucleic acid sequence encodes a CAR comprising the amino acid sequence of SEQ ID NO: 100.

In another embodiment, the nucleic acid sequence encoding a CAR comprises the nucleic acid sequence of SEQ ID NO: 101. In one embodiment, the nucleic acid sequence encodes a CAR comprising the amino acid sequence of SEQ ID NO: 102.

In another embodiment, the nucleic acid sequence encoding a CAR comprises the nucleic acid sequence of SEQ ID NO: 103. In one embodiment, the nucleic acid sequence encodes a CAR comprising the amino acid sequence of SEQ ID NO: 104.

In another embodiment, the nucleic acid sequence encoding a CAR comprises the nucleic acid sequence of SEQ ID NO: 105. In one embodiment, the nucleic acid sequence encodes a CAR comprising the amino acid sequence of SEQ ID NO: 106.

In another embodiment, the nucleic acid sequence encoding a CAR comprises the nucleic acid sequence of SEQ ID NO: 107. In one embodiment, the nucleic acid sequence encodes a CAR comprising the amino acid sequence of SEQ ID NO: 108.

In another embodiment, the nucleic acid sequence encoding a CAR comprises the nucleic acid sequence of SEQ ID NO: 109. In one embodiment, the nucleic acid sequence encodes a CAR comprising the amino acid sequence of SEQ ID NO: 110.

In another embodiment, the nucleic acid sequence encoding a CAR comprises the nucleic acid sequence of SEQ ID NO: 111. In one embodiment, the nucleic acid sequence encodes a CAR comprising the amino acid sequence of SEQ ID NO: 112.

In another embodiment, the nucleic acid sequence encoding a CAR comprises the nucleic acid sequence of SEQ ID NO: 113. In one embodiment, the nucleic acid sequence encodes a CAR comprising the amino acid sequence of SEQ ID NO: 114.

In another embodiment, the nucleic acid sequence encoding a CAR comprises the nucleic acid sequence of SEQ ID NO: 115. In one embodiment, the nucleic acid sequence encodes a CAR comprising the amino acid sequence of SEQ ID NO: 116.

In one aspect, the CARs disclosed herein are modified to express or contain a detectable marker for use in diagnosis, monitoring, and/or predicting the treatment outcome such as progression free survival of cancer patients or for monitoring the progress of such treatment.

In one embodiment, the nucleic acid molecule encoding the disclosed CARs can be contained in a vector, such as a viral vector. The vector is a DNA vector, an RNA vector, a plasmid vector, a cosmid vector, a herpes virus vector, a measles virus vector, a lentivirus vector, adenoviral vector, or a retrovirus vector, or a combination thereof.

In certain embodiments, the vector further comprises a promoter wherein the promoter is an inducible promoter, a tissue specific promoter, a constitutive promoter, a suicide promoter or any combination thereof.

In yet another embodiment, the vector expressing the CAR can be further modified to include one or more operative elements to control the expression of CAR T cells, or to eliminate CAR-T cells by virtue of a suicide switch. The suicide switch can include, for example, an apoptosis inducing signaling cascade or a drug that induces cell death. In a preferred embodiment, the vector expressing the CAR can be further modified to express an enzyme such thymidine kinase (TK) or cytosine deaminase (CD).

In another aspect, host cells including the nucleic acid molecule encoding the CAR are also provided. In some embodiments, the host cell is a T cell, such as a primary T cell obtained from a subject. In one embodiment, the host cell is a $CD8^+$ T cell.

In yet another aspect, a pharmaceutical composition is provided comprising an anti-tumor effective amount of a population of human T cells, wherein the T cells comprise a nucleic acid sequence that encodes a chimeric antigen receptor (CAR), wherein the CAR comprises at least one extracellular antigen binding domain comprising a CD38 antigen binding domain comprising the amino acid sequence selected from the group consisting of SEQ ID NOs: 2, 4, 6, 8, 10, 12, 16, 18, 20, 22, 24, 26, 70, 72, 74, and 76; at least one linker domain; at least one transmembrane domain; and at least one intracellular signaling domain, wherein the T cells are T cells of a human having a cancer. The cancer includes, inter alia, a hematological cancer such as leukemia (e.g., chronic lymphocytic leukemia (CLL), acute lymphocytic leukemia (ALL), or chronic myelogenous leukemia (CML), lymphoma (e.g., mantle cell lymphoma, non-Hodgkin's lymphoma or Hodgkin's lymphoma) or multiple myeloma (MM), or a combination thereof.

In one embodiment, a pharmaceutical composition is provided wherein the at least one transmembrane domain of the CAR contains a transmembrane domain of a protein selected from the group consisting of the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In another embodiment, a pharmaceutical composition is provided wherein the human cancer includes an adult carcinoma comprising oral and pharynx cancer (tongue, mouth, pharynx, head and neck), digestive system cancers (esophagus, stomach, small intestine, colon, rectum, anus, liver, interhepatic bile duct, gallbladder, pancreas), respiratory system cancers (larynx, lung and bronchus), bones and joint cancers, soft tissue cancers, skin cancers (melanoma, basal and squamous cell carcinoma), pediatric tumors (neuroblastoma, rhabdomyosarcoma, osteosarcoma, Ewing's sarcoma), tumors of the central nervous system (brain, astrocytoma, glioblastoma, glioma), and cancers of the breast, the genital system (uterine cervix, uterine corpus, ovary, vulva, vagina, prostate, testis, penis, endometrium), the urinary system (urinary bladder, kidney and renal pelvis, ureter), the eye and orbit, the endocrine system (thyroid), and the brain and other nervous system, or any combination thereof.

In yet another embodiment, a pharmaceutical composition is provided comprising an anti-tumor effective amount of a population of human T cells of a human having a cancer wherein the cancer is a refractory cancer non-responsive to one or more chemotherapeutic agents. The cancer includes hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (Chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma (MM), lung cancer, breast cancer, ovarian cancer, prostate cancer, colon cancer, melanoma or other hematological cancer and solid tumors, or any combination thereof.

In another aspect, methods of making CAR-containing T cells (hereinafter "CAR-T cells") are provided. The methods include transducing a T cell with a vector or nucleic acid molecule encoding a disclosed CAR that specifically binds CD38, thereby making the CAR-T cell.

In yet another aspect, a method of generating a population of RNA-engineered cells is provided that comprises introducing an in vitro transcribed RNA or synthetic RNA of a nucleic acid molecule encoding a disclosed CAR into a cell of a subject, thereby generating a CAR cell.

In yet another aspect, a method for diagnosing a disease, disorder or condition associated with the expression of CD38 on a cell, is provided comprising a) contacting the cell with a human anti-CD38 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, and 76; and b) detecting the presence of CD38 wherein the presence of CD38 diagnoses for the disease, disorder or condition associated with the expression of CD38.

In one embodiment, the disease, disorder or condition associated with the expression of CD38 is cancer including hematopoietic cancer, myelodysplastic syndrome pancreatic cancer, head and neck cancer, cutaneous tumors, minimal residual disease (MRD) in acute lymphoblastic leukemia (ALL), acute myeloid leukemia (AML), adult B cell malignancies including, CLL (chronic lymphocytic leukemia), CML (chronic myelogenous leukemia), non-Hodgkin's lymphoma (NHL), pediatric B cell malignancies (including B lineage ALL (acute lymphocytic leukemia)), multiple myeloma (MM), lung cancer, breast cancer, ovarian cancer, prostate cancer, colon cancer, melanoma or other hematological cancer and solid tumors, or any combination thereof.

In another embodiment, a method of diagnosing, prognosing, or determining risk of a CD38-related disease in a mammal, is provided comprising detecting the expression of CD38 in a sample derived from the mammal comprising: a) contacting the sample with a human anti-CD38 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, and 76; and b) detecting the presence of CD38 wherein the presence of CD38 diagnoses for a CD38-related disease in the mammal.

In another embodiment, a method of inhibiting CD38-dependent T cell inhibition, is provided comprising contacting a cell with a human anti-CD38 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, and 76. In one embodiment, the cell is selected from the group consisting of a CD38-expressing tumor cell, a tumor-associated macrophage, and any combination thereof.

In another embodiment, a method of blocking T-cell inhibition mediated by a CD38-expressing cell and altering the tumor microenvironment to inhibit tumor growth in a mammal, is provided comprising administering to the mammal an effective amount of a composition comprising an isolated anti-CD38 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, and 76. In one embodiment, the cell is selected from the group consisting of a CD38-expressing tumor cell, a tumor-associated macrophage, and any combination thereof.

In another embodiment, a method of inhibiting, suppressing or preventing immunosuppression of an anti-tumor or anti-cancer immune response in a mammal, is provided comprising administering to the mammal an effective amount of a composition comprising an isolated anti-CD38 antibody or fragment thereof, wherein the antibody or a fragment thereof comprises an amino acid sequence selected from the group consisting of SEQ ID NOs: 2, 4, 6, 8, 10, 12, 16, 18, 20, 22, 24, 26, 70, 72, 74, or 76. In one embodiment, the antibody or fragment thereof inhibits the interaction between a first cell with a T cell, wherein the first cell is selected from the group consisting of a CD38-expressing tumor cell, a tumor-associated macrophage, and any combination thereof.

In another aspect, a method is provided for inducing an anti-tumor immunity in a mammal comprising administering to the mammal a therapeutically effective amount of a T cell transduced with vector or nucleic acid molecule encoding a disclosed CAR.

In another embodiment, a method of treating or preventing cancer in a mammal is provided comprising administering to the mammal one or more of the disclosed CARs, in an amount effective to treat or prevent cancer in the mammal. The method includes administering to the subject a therapeutically effective amount of host cells expressing a disclosed CAR that specifically binds CD38 and/or one or more of the aforementioned antigens, under conditions sufficient to form an immune complex of the antigen binding domain on the CAR and the extracellular domain of CD38 and/or one or more of the aforementioned antigens in the subject.

In yet another embodiment, a method is provided for treating a mammal having a disease, disorder or condition associated with an elevated expression of a tumor antigen, the method comprising administering to the subject a pharmaceutical composition comprising an anti-tumor effective amount of a population of T cells, wherein the T cells comprise a nucleic acid sequence that encodes a chimeric antigen receptor (CAR), wherein the CAR includes at least one extracellular CD38 antigen binding domain comprising the amino acid sequence of SEQ ID NOs: 2, 4, 6, 8, 10, 12, 16, 18, 20, 22, 24, 26, 70, 72, 74, or 76, or any combination thereof, at least one linker or spacer domain, at least one transmembrane domain, at least one intracellular signaling domain, and wherein the T cells are T cells of the subject having cancer.

In yet another embodiment, a method is provided for treating cancer in a subject in need thereof comprising administering to the subject a pharmaceutical composition comprising an anti-tumor effective amount of a population of T cells, wherein the T cells comprise a nucleic acid sequence that encodes a chimeric antigen receptor (CAR), wherein the CAR comprises at least one CD38 antigen binding domain comprising the amino acid sequence of SEQ ID NOs: 2, 4, 6, 8, 10, 12, 16, 18, 20, 22, 24, 26, 70, 72, 74, or 76, or any combination thereof, at least one linker or spacer domain, at least one transmembrane domain, at least one intracellular signaling domain, wherein the T cells are T cells of the subject having cancer. In some embodiments of the aforementioned methods, the at least one transmembrane domain comprises a transmembrane the alpha, beta or zeta chain of the T-cell receptor, CD28, CD3 epsilon, CD45, CD4, CD5, CD8, CD9, CD16, CD22, Mesothelin, CD33, CD37, CD64, CD80, CD86, CD134, CD137 and CD154, or a combination thereof.

In yet another embodiment, a method is provided for generating a persisting population of genetically engineered T cells in a human diagnosed with cancer. In one embodiment, the method comprises administering to a human a T cell genetically engineered to express a CAR wherein the CAR comprises at least one CD38 antigen binding domain comprising the amino acid sequence of SEQ ID NOs: 2, 4, 6, 8, 10, 12, 16, 18, 20, 22, 24, 26, 70, 72, 74, or 76, or any combination thereof, at least one transmembrane domain; and at least one intracellular signaling domain wherein the persisting population of genetically engineered T cells, or the population of progeny of the T cells, persists in the human for at least one month, two months, three months, four months, five months, six months, seven months, eight months, nine months, ten months, eleven months, twelve months, two years, or three years after administration.

In one embodiment, the progeny T cells in the human comprise a memory T cell. In another embodiment, the T cell is an autologous T cell.

In all of the aspects and embodiments of methods described herein, any of the aforementioned cancers, diseases, disorders or conditions associated with an elevated expression of a tumor antigen that may be treated or prevented or ameliorated using one or more of the CARs disclosed herein, In yet another aspect, a kit is provided for making a chimeric antigen receptor T-cell as described supra or for preventing, treating, or ameliorating any of the cancers, diseases, disorders or conditions associated with an elevated expression of a tumor antigen in a subject as described supra, comprising a container comprising any one of the nucleic acid molecules, vectors, host cells, or compositions disclosed supra or any combination thereof, and instructions for using the kit.

It will be understood that the CARs, host cells, nucleic acids, and methods are useful beyond the specific aspects and embodiments that are described in detail herein. The foregoing features and advantages of the disclosure will become more apparent from the following detailed description, which proceeds with reference to the accompanying figures.

BRIEF DESCRIPTION OF THE FIGURES

FIG. 1 depicts the general structure of CARs targeting CD38. The anti-CD38 ScFv targeting domain was linked in frame to CD8 hinge and transmembrane domain, the 4-1BB (CD137) costimulatory domain and the CD3 zeta signaling domain.

FIG. 4A shows IFNg cytokine production by CAR-T, listed on the x-axis, upon overnight co-culture with RPMI-8226, and MM1.S tumor lines at an E:T ratio of 10:1 measured using ELISA. FIG. 4B shows TNFa cytokine production by CAR-T, listed on the x-axis, upon overnight co-culture with RPMI-8226, and MM1.S tumor lines at an E:T ratio of 10:1 measured using ELISA. Bars represent mean+SD of three replicate samples. Data are representative of three independent experiments performed with CAR T cells from three separate donors.

DETAILED DESCRIPTION

Definitions

Figure 2:
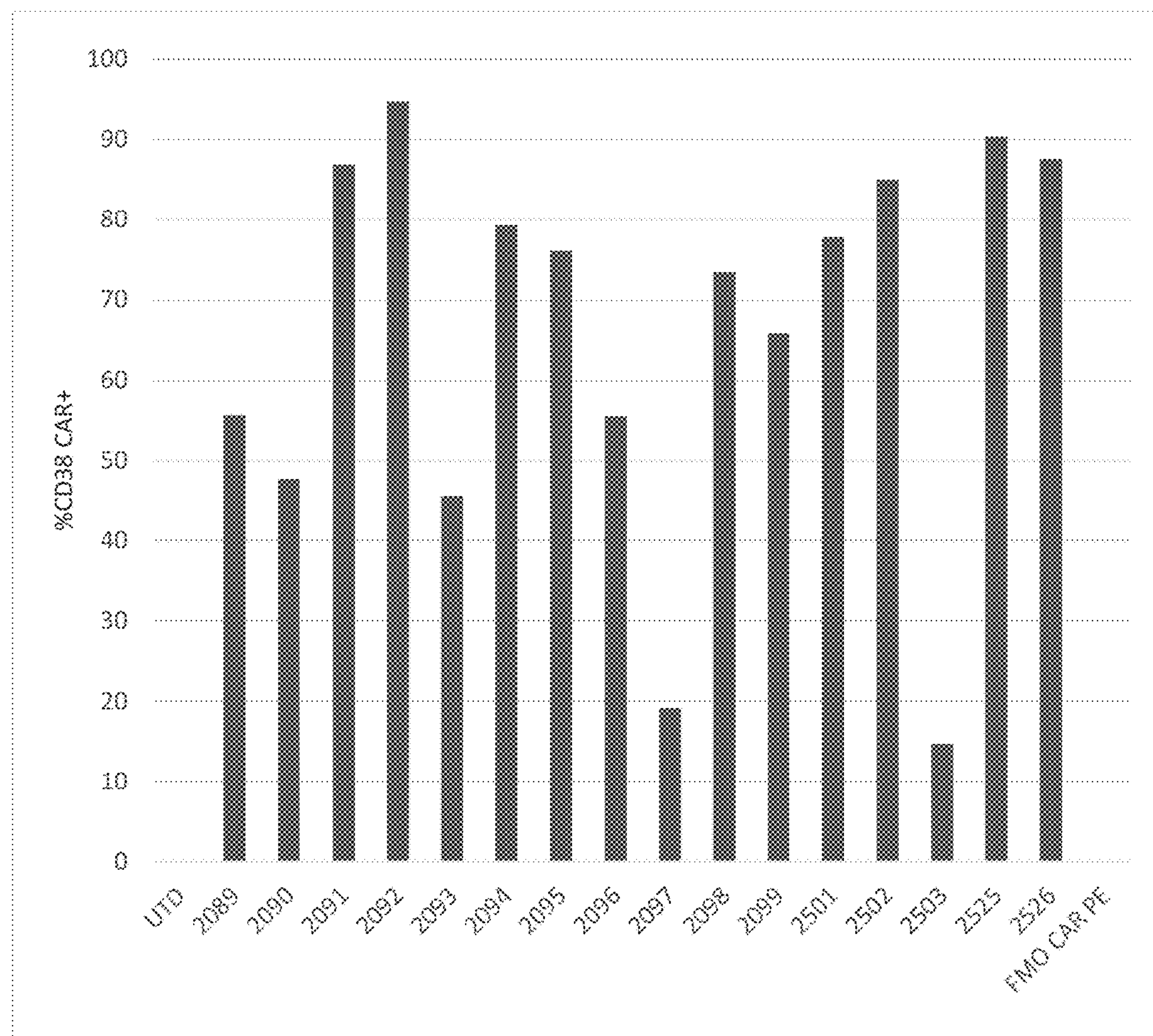
FIG. 2 depicts surface expression of CD38-targeting CAR T constructs on human primary T cells. CAR T expression was determined by flow cytometry. T cells were activated with Miltenyi Biotec TransAct™ CD3 CD28 reagent in the presence of IL-2, and transduced with LV as described in Materials and Methods. On culture day 8, viable transduced T cells (7-AAD negative) were assayed for CAR surface expression using CD38-His reagent, followed by anti-His-PE. The CAR construct LV used in transduction is listed below each bar. Bars represent the percentage of CAR T-positive populations in relation to non-transduced T cell control (UTD). Data are representative of three independent experiments performed with CAR T cells from three separate donors.

As used herein, the singular forms "a," "an," and "the," refer to both the singular as well as plural, unless the context clearly indicates otherwise. For example, the term "an antigen" includes single or plural antigens and can be considered equivalent to the phrase "at least one antigen." As used herein, the term "comprises" means "includes." Thus, "comprising an antigen" means "including an antigen" without excluding other elements. The phrase "and/or" means "and" or "or." It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the Materials, Methods, and Examples are illustrative only and not intended to be limiting. To facilitate review of the various embodiments, the following explanations of terms are provided:

The term "about" when referring to a measurable value such as an amount, a temporal duration, and the like, is meant to encompass variations of .+-.20% or in some instances .+-.10%, or in some instances .+-.5%, or in some instances .+-.1%, or in some instances .+-.0.1% from the specified value, as such variations are appropriate to perform the disclosed methods.

Unless otherwise noted, the technical terms herein are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: A Comprehensive Desk Reference*, published by VCH Publishers, Inc., 1995; and other similar references.

The present disclosure provides for CD38 antibodies or fragments thereof as well as chimeric antigen receptors (CARs) having such CD38 antigen binding domains. The enhancement of the functional activity of the CAR directly relates to the enhancement of functional activity of the CAR-expressing T cell. As a result of one or more of these modifications, the CARs exhibit both a high degree of cytokine-induced cytolysis and cell surface expression on transduced T cells, along with an increased level of in vivo T cell expansion and persistence of the transduced CAR-expressing T cell.

The unique ability to combine functional moieties derived from different protein domains has been a key innovative feature of Chimeric Antigen Receptors (CARs). The choice of each of these protein domains is a key design feature, as is the way in which they are specifically combined. Each design domain is an essential component that can be used across different CAR platforms to engineer the function of lymphocytes. For example, the choice of the extracellular binding domain can make an otherwise ineffective CAR be effective.

The invariable framework components of the immunoglobulin-derived protein sequences used to create the extracellular antigen binding domain of a CAR can either be entirely neutral, or they can self-associate and drive the T cell to a state of metabolic exhaustion, thus making the therapeutic T cell expressing that CAR far less effective. This occurs independently of the antigen binding function of this CAR domain. Furthermore, the choice of the intracellular signaling domain(s) also can govern the activity and the durability of the therapeutic lymphocyte population used for immunotherapy. While the ability to bind target antigen and the ability to transmit an activation signal to the T cell through these extracellular and intracellular domains, respectively, are important CAR design aspects, what has also become apparent is that the choice of the source of the extracellular antigen binding fragments can have a significant effect on the efficacy of the CAR and thereby have a defining role for the function and clinical utility of the CAR.

Surprisingly and unexpectedly it has now been discovered that use of an entirely human antigen binding domain in a CAR, rather than using mouse-derived antigen binding fragments which are prone to induce anti-mouse immune response and CAR T elimination in a host (c.f., the UPenn-sponsored clinical trial using mouse derived SS1 ScFv sequence, NCT02159716), may also determine the functional activity of a CAR-expressing T cell.

The CARs disclosed herein are expressed at a high level in a cell. A cell expressing the CAR has a high in vivo proliferation rate, produces large amounts of cytokines, and has a high cytotoxic activity against a cell having, on its surface, a CD38 antigen to which a CAR binds. The use of a human extracellular CD38 antigen binding domain results in generation of a CAR that functions better in vivo, while avoiding the induction of anti-CAR immunity in the host immune response and the killing of the CAR T cell population. The CARs expressing the entirely human extracellular CD38 ScFv antigen binding domain exhibit superior activities/properties including i) prevention of poor CAR T persistence and function as seen with mouse-derived binding sequences; ii) lack of requirement for regional delivery of the CAR to be efficacious; and iii) ability to generate CAR T cell designs based both on binders with high and low affinity to CD38. This latter property allows investigators to better tune efficacy vs toxicity, and/or tissue specificity of the CAR T product, since lower-affinity binders may have higher specificity to tumors vs normal tissues due to higher expression of CD38 on tumors than normal tissue, which may prevent on-target off tumor toxicity and bystander cell killing.

What follows is a detailed description of the inventive CARs including a description of their extracellular CD38 antigen binding domain, the transmembrane domain and the intracellular domain, along with additional description of the CARs, antibodies and antigen binding fragments thereof, conjugates, nucleotides, expression, vectors, and host cells, methods of treatment, compositions, and kits employing the disclosed CARs.

A. Chimeric Antigen Receptors (CARs)

The CARs disclosed herein comprise at least one CD38 antigen binding domain capable of binding to CD38, at least one transmembrane domain, and at least one intracellular domain.

A chimeric antigen receptor (CAR) is an artificially constructed hybrid protein or polypeptide containing the antigen binding domains of an antibody (e.g., single chain variable fragment (ScFv)) linked to T-cell signaling domains via the transmembrane domain. Characteristics of CARs include their ability to redirect T-cell specificity and reactivity toward a selected target in a non-MHC-restricted manner, and exploiting the antigen-binding properties of monoclonal antibodies. The non-MHC-restricted antigen recognition gives T cells expressing CARs the ability to recognize antigen independent of antigen processing, thus bypassing a major mechanism of tumor escape. Moreover, when expressed in T-cells, CARs advantageously do not dimerize with endogenous T cell receptor (TCR) alpha and beta chains.

As disclosed herein, the intracellular T cell signaling domains of the CARs can include, for example, a T cell receptor signaling domain, a T cell costimulatory signaling domain, or both. The T cell receptor signaling domain refers to a portion of the CAR comprising the intracellular domain of a T cell receptor, such as, for example, and not by way of limitation, the intracellular portion of the CD3 zeta protein. The costimulatory signaling domain refers to a portion of the CAR comprising the intracellular domain of a costimulatory molecule, which is a cell surface molecule other than an antigen receptor or their ligands that are required for an efficient response of lymphocytes to antigen.

1. Extracellular Domain

In one embodiment, the CAR comprises a target-specific binding element otherwise referred to as an antigen binding domain or moiety. The choice of domain depends upon the type and number of ligands that define the surface of a target cell. For example, the antigen binding domain may be chosen to recognize a ligand that acts as a cell surface marker on target cells associated with a particular disease state. Thus, examples of cell surface markers that may act as ligands for the antigen binding domain in the CAR include those associated with viral, bacterial and parasitic infections, autoimmune disease and cancer cells.

In one embodiment, the CAR can be engineered to target a tumor antigen of interest by way of engineering a desired antigen binding domain that specifically binds to an antigen on a tumor cell. Tumor antigens are proteins that are produced by tumor cells that elicit an immune response, particularly T-cell mediated immune responses. The selection of the antigen binding domain will depend on the particular type of cancer to be treated. Tumor antigens include, for example, a glioma-associated antigen, carcinoembryonic antigen (CEA), .beta.-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and CD38. The tumor antigens disclosed herein are merely included by way of example. The list is not intended to be exclusive and further examples will be readily apparent to those of skill in the art.

In one embodiment, the tumor antigen comprises one or more antigenic cancer epitopes associated with a malignant tumor. Malignant tumors express a number of proteins that can serve as target antigens for an immune attack. These molecules include, but are not limited to, tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

In one preferred embodiment, the tumor antigen is CD38 and the tumors associated with expression of CD38 comprise lung mesothelioma, ovarian, and pancreatic cancers that express high levels of the extracellular protein CD38, or any combination thereof.

The type of tumor antigen may also be a tumor-specific antigen (TSA) or a tumor-associated antigen (TAA). A TSA is unique to tumor cells and does not occur on other cells in the body. A TAA is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond, or they may be antigens that are normally present at extremely low levels on normal cells, but which are expressed at much higher levels on tumor cells.

Non-limiting examples of TSAs or TAAs include the following: Differentiation antigens such as MART-1/MelanA (MART-I), gp100 (Pmel 17), tyrosinase, TRP-1, TRP-2 and tumor-specific multi-lineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In one embodiment, the antigen binding domain portion of the CAR targets an antigen that includes but is not limited to CD19, CD20, CD22, ROR1, CD123, CD33, CD38, c-Met, PSMA, Glycolipid F77, EGFRvIII, GD-2, MY-ESO-1 TCR, MAGE A3 TCR, and the like.

In a preferred embodiment, the antigen binding domain portion of the CAR targets the extracellular CD38 antigen.

In one preferred embodiment, the isolated nucleic acid molecule encoding the extracellular CD38 hScFv M3801 antigen binding domain comprises a nucleotide sequence of SEQ ID NO: 1, or a sequence with 85%, 90%, 95%, 96%, 97%, 98% or 99% identity thereof. In one embodiment, an isolated nucleic acid molecule is provided wherein the encoded extracellular CD38 hScFv M3801 antigen binding domain comprises an amino acid sequence of SEQ ID NO: 2, or an amino acid sequence with 85%, 90%, 95%, 96%, 97%, 98% or 99% identity to an amino acid sequence of SEQ ID NO: 2.

In one preferred embodiment, the isolated nucleic acid molecule encoding the extracellular CD38 hScFv M3802 antigen binding domain comprises a nucleotide sequence of SEQ ID NO: 3, or a sequence with 85%, 90%, 95%, 96%, 97%, 98% or 99% identity thereof. In one embodiment, an isolated nucleic acid molecule is provided wherein the encoded extracellular CD38 hScFv M3802 antigen binding domain comprises an amino acid sequence of SEQ ID NO: 4, or an amino acid sequence with 85%, 90%, 95%, 96%, 97%, 98% or 99% identity to an amino acid sequence of SEQ ID NO: 4.

In one preferred embodiment, the isolated nucleic acid molecule encoding the extracellular CD38 hScFv M3803 antigen binding domain comprises a nucleotide sequence of SEQ ID NO: 5, or a sequence with 85%, 90%, 95%, 96%, 97%, 98% or 99% identity thereof. In one embodiment, an isolated nucleic acid molecule is provided wherein the encoded extracellular CD38 hScFv M3803 antigen binding domain comprises an amino acid sequence of SEQ ID NO: 6, or an amino acid sequence with 85%, 90%, 95%, 96%, 97%, 98% or 99% identity to an amino acid sequence of SEQ ID NO: 6.

In one preferred embodiment, the isolated nucleic acid molecule encoding the extracellular CD38 hScFv M3804 antigen binding domain comprises a nucleotide sequence of SEQ ID NO: 7, or a sequence with 85%, 90%, 95%, 96%, 97%, 98% or 99% identity thereof. In one embodiment, an isolated nucleic acid molecule is provided wherein the encoded extracellular CD38 hScFv M3804 antigen binding domain comprises an amino acid sequence of SEQ ID NO: 8, or an amino acid sequence with 85%, 90%, 95%, 96%, 97%, 98% or 99% identity to an amino acid sequence of SEQ ID NO: 8.

In one preferred embodiment, the isolated nucleic acid molecule encoding the extracellular CD38 hScFv M3806 antigen binding domain comprises a nucleotide sequence of SEQ ID NO: 9, or a sequence with 85%, 90%, 95%, 96%, 97%, 98% or 99% identity thereof. In one embodiment, an isolated nucleic acid molecule is provided wherein the encoded extracellular CD38 hScFv M3806 antigen binding domain comprises an amino acid sequence of SEQ ID NO: 10, or an amino acid sequence with 85%, 90%, 95%, 96%, 97%, 98% or 99% identity to an amino acid sequence of SEQ ID NO: 10.

In one preferred embodiment, the isolated nucleic acid molecule encoding the extracellular CD38 hScFv M3808 antigen binding domain comprises a nucleotide sequence of SEQ ID NO: 11, or a sequence with 85%, 90%, 95%, 96%, 97%, 98% or 99% identity thereof. In one embodiment, an isolated nucleic acid molecule is provided wherein the encoded extracellular CD38 hScFv M3808 antigen binding domain comprises an amino acid sequence of SEQ ID NO: 12, or an amino acid sequence with 85%, 90%, 95%, 96%, 97%, 98% or 99% identity to an amino acid sequence of SEQ ID NO: 12.

In one preferred embodiment, the isolated nucleic acid molecule encoding the extracellular CD38 hScFv M3809 antigen binding domain comprises a nucleotide sequence of SEQ ID NO: 15, or a sequence with 85%, 90%, 95%, 96%, 97%, 98% or 99% identity thereof. In one embodiment, an isolated nucleic acid molecule is provided wherein the encoded extracellular CD38 hScFv M3809 antigen binding domain comprises an amino acid sequence of SEQ ID NO: 16, or an amino acid sequence with 85%, 90%, 95%, 96%, 97%, 98% or 99% identity to an amino acid sequence of SEQ ID NO: 16.

In one preferred embodiment, the isolated nucleic acid molecule encoding the extracellular CD38 hScFv M3810 antigen binding domain comprises a nucleotide sequence of SEQ ID NO: 17, or a sequence with 85%, 90%, 95%, 96%, 97%, 98% or 99% identity thereof. In one embodiment, an isolated nucleic acid molecule is provided wherein the encoded extracellular CD38 hScFv M3810 antigen binding domain comprises an amino acid sequence of SEQ ID NO: 18, or an amino acid sequence with 85%, 90%, 95%, 96%, 97%, 98% or 99% identity to an amino acid sequence of SEQ ID NO: 18.

In one preferred embodiment, the isolated nucleic acid molecule encoding the extracellular CD38 hScFv M3811 antigen binding domain comprises a nucleotide sequence of SEQ ID NO: 19, or a sequence with 85%, 90%, 95%, 96%, 97%, 98% or 99% identity thereof. In one embodiment, an isolated nucleic acid molecule is provided wherein the encoded extracellular CD38 hScFv M3811 antigen binding domain comprises an amino acid sequence of SEQ ID NO: 20, or an amino acid sequence with 85%, 90%, 95%, 96%, 97%, 98% or 99% identity to an amino acid sequence of SEQ ID NO: 20.

In one preferred embodiment, the isolated nucleic acid molecule encoding the extracellular CD38 hScFv M3812 antigen binding domain comprises a nucleotide sequence of SEQ ID NO: 21, or a sequence with 85%, 90%, 95%, 96%, 97%, 98% or 99% identity thereof. In one embodiment, an isolated nucleic acid molecule is provided wherein the encoded extracellular CD38 hScFv M3812 antigen binding domain comprises an amino acid sequence of SEQ ID NO: 22, or an amino acid sequence with 85%, 90%, 95%, 96%, 97%, 98% or 99% identity to an amino acid sequence of SEQ ID NO: 22.

In one preferred embodiment, the isolated nucleic acid molecule encoding the extracellular CD38 hScFv M3815 antigen binding domain comprises a nucleotide sequence of SEQ ID NO: 23, or a sequence with 85%, 90%, 95%, 96%, 97%, 98% or 99% identity thereof. In one embodiment, an isolated nucleic acid molecule is provided wherein the encoded extracellular CD38 hScFv M3815 antigen binding domain comprises an amino acid sequence of SEQ ID NO: 24, or an amino acid sequence with 85%, 90%, 95%, 96%, 97%, 98% or 99% identity to an amino acid sequence of SEQ ID NO: 24.

In one preferred embodiment, the isolated nucleic acid molecule encoding the extracellular CD38 hScFv M3815_P antigen binding domain comprises a nucleotide sequence of SEQ ID NO: 25, or a sequence with 85%, 90%, 95%, 96%, 97%, 98% or 99% identity thereof. In one embodiment, an isolated nucleic acid molecule is provided wherein the encoded extracellular CD38 hScFv M3815_P antigen binding domain comprises an amino acid sequence of SEQ ID NO: 26, or an amino acid sequence with 85%, 90%, 95%, 96%, 97%, 98% or 99% identity to an amino acid sequence of SEQ ID NO: 26.

In one preferred embodiment, the isolated nucleic acid molecule encoding the extracellular CD38 hScFv M3816 antigen binding domain comprises a nucleotide sequence of SEQ ID NO: 69, or a sequence with 85%, 90%, 95%, 96%, 97%, 98% or 99% identity thereof. In one embodiment, an isolated nucleic acid molecule is provided wherein the encoded extracellular CD38 hScFv M3816 antigen binding domain comprises an amino acid sequence of SEQ ID NO: 70, or an amino acid sequence with 85%, 90%, 95%, 96%, 97%, 98% or 99% identity to an amino acid sequence of SEQ ID NO: 70.

In one preferred embodiment, the isolated nucleic acid molecule encoding the extracellular CD38 hScFv M3817 antigen binding domain comprises a nucleotide sequence of SEQ ID NO: 71, or a sequence with 85%, 90%, 95%, 96%, 97%, 98% or 99% identity thereof. In one embodiment, an isolated nucleic acid molecule is provided wherein the encoded extracellular CD38 hScFv M3817 antigen binding domain comprises an amino acid sequence of SEQ ID NO: 72, or an amino acid sequence with 85%, 90%, 95%, 96%, 97%, 98% or 99% identity to an amino acid sequence of SEQ ID NO: 72.

In one preferred embodiment, the isolated nucleic acid molecule encoding the extracellular CD38 hScFv M8DR H_L antigen binding domain comprises a nucleotide sequence of SEQ ID NO: 73, or a sequence with 85%, 90%, 95%, 96%, 97%, 98% or 99% identity thereof. In one embodiment, an isolated nucleic acid molecule is provided wherein the encoded extracellular CD38 hScFv M8DR H_L antigen binding domain comprises an amino acid sequence of SEQ ID NO: 74, or an amino acid sequence with 85%, 90%, 95%, 96%, 97%, 98% or 99% identity to an amino acid sequence of SEQ ID NO: 74.

In one preferred embodiment, the isolated nucleic acid molecule encoding the extracellular CD38 hScFv M8DR L_H antigen binding domain comprises a nucleotide sequence of SEQ ID NO: 75, or a sequence with 85%, 90%, 95%, 96%, 97%, 98% or 99% identity thereof. In one embodiment, an isolated nucleic acid molecule is provided wherein the encoded extracellular CD38 hScFv M8DR L_H antigen binding domain comprises an amino acid sequence of SEQ ID NO: 76, or an amino acid sequence with 85%, 90%, 95%, 96%, 97%, 98% or 99% identity to an amino acid sequence of SEQ ID NO: 74.

The generation and binding characteristics of the specific CD38 variable heavy chain only and ScFv antigen binding fragments or antigen binders described herein is shown in Example 1.

In the various embodiments of the CD38-specific CARs disclosed herein, the general scheme is set forth in FIG. 1 and includes, from the N-terminus to the C-terminus, a signal or leader peptide, anti-CD38 hScFv, extracellular linker, CD8 transmembrane, 4-1BB, CD3 zeta, wherein the bolded text represents the cloning sites for linking domains.

In another embodiment, the nucleic acid sequence encoding a CAR comprises the nucleic acid sequence of SEQ ID NO: 77, and encodes the CAR comprising the amino acid sequence as set forth in SEQ ID NO: 78.

In another embodiment, the nucleic acid sequence encoding a CAR comprises the nucleic acid sequence of SEQ ID NO: 77 or a sequence with 85%, 90%, 95%, 96%, 97%, 98% or 99% identity thereof, and encodes the CAR comprising the amino acid sequence as set forth in SEQ ID NO: 78 or a sequence with 85%, 90%, 95%, 96%, 97%, 98% or 99% identity thereof.

In another embodiment, the nucleic acid sequence encoding a CAR comprises the nucleic acid sequence of SEQ ID NO: 87, and encodes the CAR comprising the amino acid sequence as set forth in SEQ ID NO: 88.

In another embodiment, the nucleic acid sequence encoding a CAR comprises the nucleic acid sequence of SEQ ID NO: 87 or a sequence with 85%, 90%, 95%, 96%, 97%, 98% or 99% identity thereof, and encodes the CAR comprising the amino acid sequence as set forth in SEQ ID NO: 88 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 89, and encodes the CAR comprising the amino acid sequence as set forth in SEQ ID NO: 90.

In yet another embodiment, the nucleic acid sequence encoding a CAR comprises the nucleic acid sequence of SEQ ID NO: 89 or a sequence with 85%, 90%, 95%, 96%, 97%, 98% or 99% identity thereof, and encodes the CAR comprising the amino acid sequence as set forth in SEQ ID NO: 90 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 91, and encodes the CAR comprising the amino acid sequence as set forth in SEQ ID NO: 92.

In yet another embodiment, the nucleic acid sequence encoding a CAR comprises the nucleic acid sequence of SEQ ID NO: 91 or a sequence with 85%, 90%, 95%, 96%, 97%, 98% or 99% identity thereof, and encodes the CAR comprising the amino acid sequence as set forth in SEQ ID NO: 92 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 93, and encodes the CAR comprising the amino acid sequence as set forth in SEQ ID NO: 94.

In yet another embodiment, the nucleic acid sequence encoding a CAR comprises the nucleic acid sequence of SEQ ID NO: 93 or a sequence with 85%, 90%, 95%, 96%, 97%, 98% or 99% identity thereof, and encodes the CAR comprising the amino acid sequence as set forth in SEQ ID NO: 94 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 95, and encodes the CAR comprising the amino acid sequence as set forth in SEQ ID NO: 96.

In yet another embodiment, the nucleic acid sequence encoding a CAR comprises the nucleic acid sequence of SEQ ID NO: 95 or a sequence with 85%, 90%, 95%, 96%, 97%, 98% or 99% identity thereof, and encodes the CAR comprising the amino acid sequence as set forth in SEQ ID NO: 96 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 97, and encodes the CAR comprising the amino acid sequence as set forth in SEQ ID NO: 98.

In yet another embodiment, the nucleic acid sequence encoding a CAR comprises the nucleic acid sequence of SEQ ID NO: 97 or a sequence with 85%, 90%, 95%, 96%, 97%, 98% or 99% identity thereof, and encodes the CAR comprising the amino acid sequence as set forth in SEQ ID NO: 98 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 99, and encodes the CAR comprising the amino acid sequence as set forth in SEQ ID NO: 100.

In yet another embodiment, the nucleic acid sequence encoding a CAR comprises the nucleic acid sequence of SEQ ID NO: 99 or a sequence with 85%, 90%, 95%, 96%, 97%, 98% or 99% identity thereof, and encodes the CAR comprising the amino acid sequence as set forth in SEQ ID NO: 100 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 101, and encodes the CAR comprising the amino acid sequence as set forth in SEQ ID NO: 102.

In yet another embodiment, the nucleic acid sequence encoding a CAR comprises the nucleic acid sequence of SEQ ID NO: 101 or a sequence with 85%, 90%, 95%, 96%, 97%, 98% or 99% identity thereof, and encodes the CAR comprising the amino acid sequence as set forth in SEQ ID NO: 102 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 103, and encodes the CAR comprising the amino acid sequence as set forth in SEQ ID NO: 104.

In yet another embodiment, the nucleic acid sequence encoding a CAR comprises the nucleic acid sequence of SEQ ID NO: 103 or a sequence with 85%, 90%, 95%, 96%, 97%, 98% or 99% identity thereof, and encodes the CAR comprising the amino acid sequence as set forth in SEQ ID NO: 104 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 105, and encodes the CAR comprising the amino acid sequence as set forth in SEQ ID NO: 106.

In yet another embodiment, the nucleic acid sequence encoding a CAR comprises the nucleic acid sequence of SEQ ID NO: 105 or a sequence with 85%, 90%, 95%, 96%, 97%, 98% or 99% identity thereof, and encodes the CAR comprising the amino acid sequence as set forth in SEQ ID NO: 106 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 107, and encodes the CAR comprising the amino acid sequence as set forth in SEQ ID NO: 108.

In yet another embodiment, the nucleic acid sequence encoding a CAR comprises the nucleic acid sequence of SEQ ID NO: 107 or a sequence with 85%, 90%, 95%, 96%, 97%, 98% or 99% identity thereof, and encodes the CAR comprising the amino acid sequence as set forth in SEQ ID NO: 108 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 109, and encodes the CAR comprising the amino acid sequence as set forth in SEQ ID NO: 110.

In yet another embodiment, the nucleic acid sequence encoding a CAR comprises the nucleic acid sequence of SEQ ID NO: 109 or a sequence with 85%, 90%, 95%, 96%, 97%, 98% or 99% identity thereof, and encodes the CAR comprising the amino acid sequence as set forth in SEQ ID NO: 110 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 111, and encodes the CAR comprising the amino acid sequence as set forth in SEQ ID NO: 112.

In yet another embodiment, the nucleic acid sequence encoding a CAR comprises the nucleic acid sequence of SEQ ID NO: 111 or a sequence with 85%, 90%, 95%, 96%, 97%, 98% or 99% identity thereof, and encodes the CAR comprising the amino acid sequence as set forth in SEQ ID NO: 112 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 113, and encodes the CAR comprising the amino acid sequence as set forth in SEQ ID NO: 114.

In yet another embodiment, the nucleic acid sequence encoding a CAR comprises the nucleic acid sequence of SEQ ID NO: 113 or a sequence with 85%, 90%, 95%, 96%, 97%, 98% or 99% identity thereof, and encodes the CAR comprising the amino acid sequence as set forth in SEQ ID NO: 114 or a sequence with 85%, 90%, 95%, 96%, 97%, 98% or 99% identity thereof.

In yet another embodiment, the nucleic acid sequence encoding a CAR comprises the nucleic acid sequence of SEQ ID NO: 115, and encodes the CAR comprising the amino acid sequence as set forth in SEQ ID NO: 116.

In yet another embodiment, the nucleic acid sequence encoding a CAR comprises the nucleic acid sequence of SEQ ID NO: 115 or a sequence with 85%, 90%, 95%, 96%, 97%, 98% or 99% identity thereof, and encodes the CAR comprising the amino acid sequence as set forth in SEQ ID NO: 116 or a sequence with 85%, 90%, 95%, 96%, 97%, 98% or 99% identity thereof.

The surface expression of anti-CD38 CARs incorporating immunoglobulin heavy chain variable domain (VH) and single chain fragment variable (ScFv) sequences reactive with CD38 antigen, is shown in Example 2 infra. CAR T expression was determined by flow cytometry. On culture day 8, viable transduced T cells (7-AAD negative) were assayed for CAR surface expression using CD38-His reagent, followed by anti-His-PE. The CAR construct LV used in transduction is listed below each bar. Bars represent the percentage of CAR T-positive populations in relation to non-transduced T cell control (UTD). Data are representative of three independent experiments performed with CAR T cells from three separate donors.

Figure 3A:
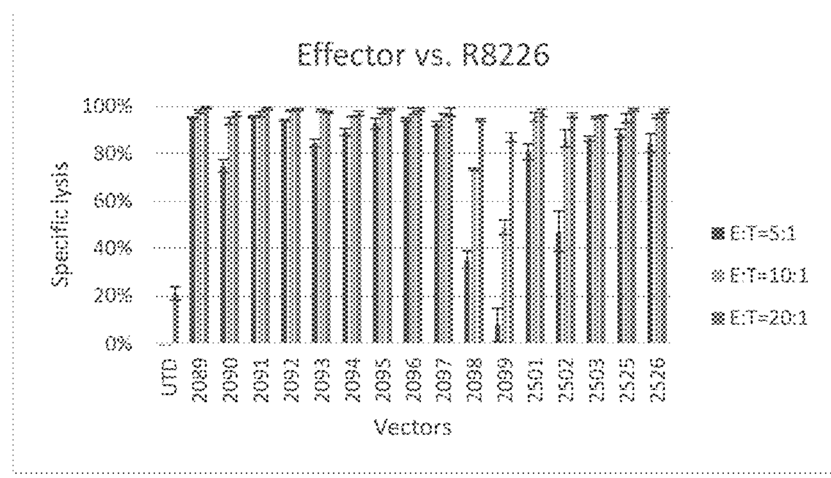
FIGS. 3A-C depict CAR T cytotoxicity in vitro. Luciferase-based cytotoxicity assays were performed using CD38-positive tumor lines RPMI-8226 (FIG. 3A), and MM1.S (FIG. 3B), or CD38-negative cell line 293T (FIG. 3C), stably transduced with luciferase. Bars represent mean+SD values from three technical replicates. Data are representative of three independent experiments performed with CAR T cells from three separate donors.
Figure 3B:
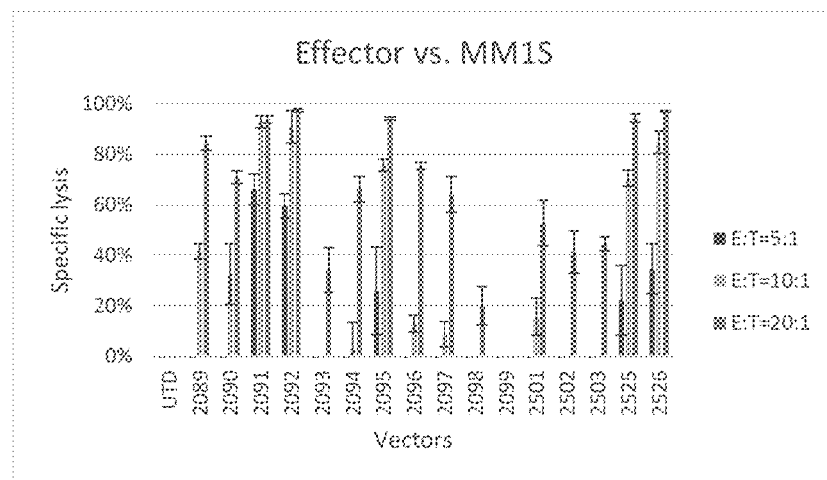
Figure 3C:
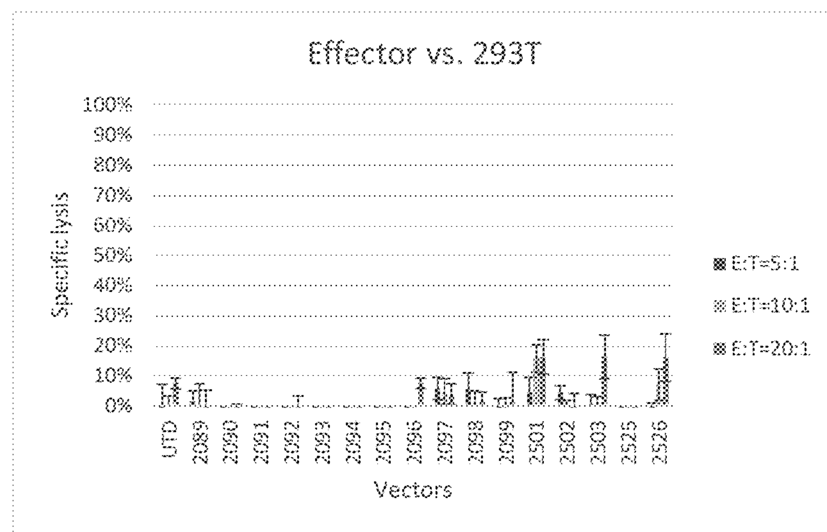

The cytotoxic potential of CAR38 candidates was assessed in luciferase-based overnight killing assays using CD38-positive tumor lines RPMI-8226, and MM1.S, or CD38-negative cell line 293T, stably transduced with luciferase. Bars represent mean+SD values from three technical replicates. Data are representative of three independent experiments performed with CAR T cells from three separate donors (FIGS. 3A-C). CAR T cells (effectors) and tumor cells (targets) were co-incubated overnight at effector to target ratio (E:T) of 5, 10, or 20. Most CAR constructs showed very potent tumor lytic activity vs $CD38^+$ tumor line RPMI-8226 (FIG. 3A), which was comparable to the positive control constructs LTG2525 and LTG2526, comprised of the comparator ScFv sequence in orientation VL-VH or VH-VL, respectively. The exception were constructs LTG2098, LTG2099, which were less cytotoxic than the positive control LTG 2525 and 2526 (FIG. 3A). By contrast, no appreciable lysis was seen for the negative control UTD (untransduced T cells), demonstrating that the tumor lysis is CAR-dependent (FIG. 3A). In killing assay vs CD38+ MM1.S cells, which are less susceptible to CAR T killing than RPMI-8226, differences in potency between CAR constructs were more prominent (FIG. 3B). CAR test constructs with the strongest anti-MM1.S lytic activity were LTG2091, LTG2092, which achieved lytic capacity greater than the control constructs LTG2525 and LTG2526 (FIG. 3B). Most other constructs achieved MM1.S lysis in high-intermediate range, and constructs LTG2099, 2093, 2098 had low lytic activity in this cells line (FIG. 3B).

Next, all CAR candidates and controls were tested in killing assay vs $CD38^-$ cell line 293T (FIG. 3C). In this instance, no lytic activity above background levels was observed for most CAR constructs, as compared to the positive control CAR LTG 2526, indicating these CAR constructs require CD38 expression for activation, which is a feature of CAR safety. An exception to this observation were construct 2501, 2503, which showed low level of CD38-independent killing activity at high E:T ratios (FIG. 3C). The non-specific killing activity of these two constructs could not be predicted based on binder data alone, and is therefore non-obvious. Overall, the cytolytic activity of most CD38 CARs in this set that was observed against CD38-expressing MM1.S and RPMI-8226 tumor cells is both target-specific and CART-dependent.

Figure 4A:
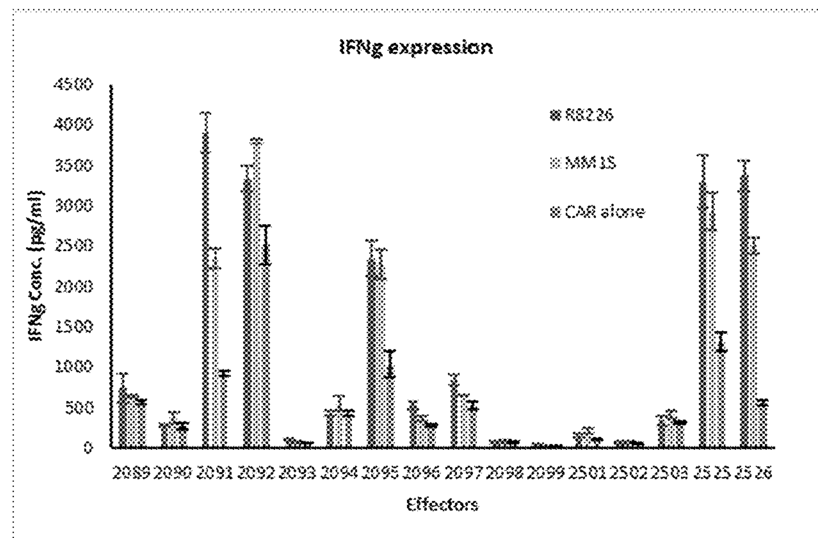
FIGS. 4A-B depict CAR T cytokine release in response to MM cell lines.
Figure 4B:
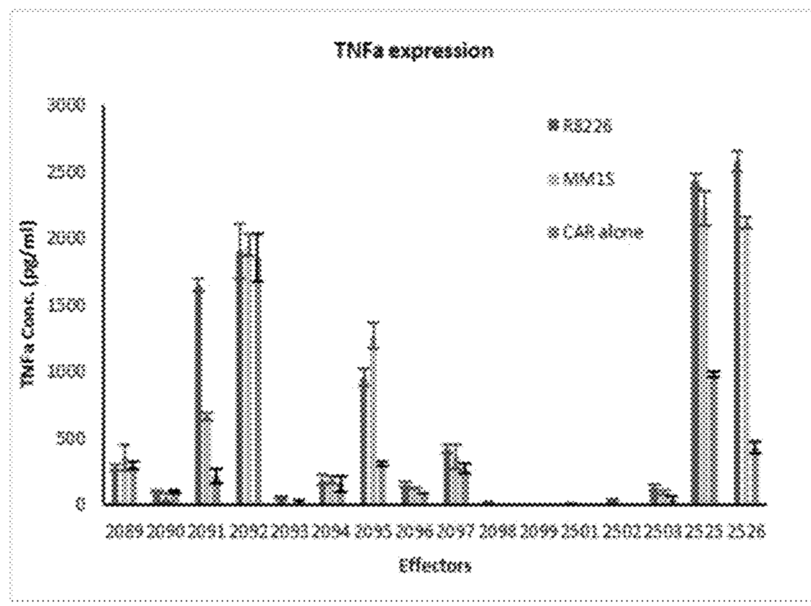

The capacity of anti-CD38 CAR T cells for secretion of pro-inflammatory cytokines IFNg and TNFa was then evaluated (FIG. 4). Cytokine production by CAR-T, listed on the x-axis, upon overnight co-culture with RPMI-8226, and MM1.S tumor lines at an E:T ratio of 10:1, was measured using ELISA. Of note, CAR T-expressing cells LTG2091, LTG2092 and LTG2095 elaborated high levels of IFN gamma and TNF alpha, which was comparable to the positive controls LTG2525 and LTG2526, whereas most of the other CAR constructs, as well as the negative control UTD group yielded low or no appreciable cytokine induction (FIGS. 4A-B). This result is in agreement with the strongest in vitro cytolytic function of LTG2091, LTG2092 and LTG2095 (c.f., FIGS. 3A-C). A second subset of constructs which did not produce high levels of cytokines, however still have high-moderate anti-tumor activity, includes LTG2089, 2090, 2094, 2096, 2097. This finding also suggests that it may be possible to select CAR38 constructs which efficiently kill tumors yet have a low risk of inducing cytokine release syndrome, thus have a better safety profile.

Without being intended to limit to any particular mechanism of action, it is believed that possible reasons for the enhanced therapeutic function associated with the exemplary CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or any combination thereof.

While the disclosure has been illustrated with an exemplary extracellular CD38 variable heavy chain only and ScFv antigen binding domains, other nucleotide and/or amino acid variants within the CD38 variable heavy chain only and ScFv antigen binding domains may be used to derive the CD38 antigen binding domains for use in the CARs described herein.

Depending on the desired antigen to be targeted, the CAR can be additionally engineered to include the appropriate antigen binding domain that is specific to the desired antigen target. For example, if CD19 is the desired antigen that is to be targeted, an antibody for CD19 can be used as the antigen bind domain incorporation into the CAR.

In one exemplary embodiment, the antigen binding domain portion of the CAR additionally targets CD19. Preferably, the antigen binding domain in the CAR is anti-CD19 ScFv, wherein the nucleic acid sequence of the anti-CD19 ScFv comprises the sequence set forth in SEQ ID NO: 37 In one embodiment, the anti-CD19 ScFv comprises the nucleic acid sequence that encodes the amino acid sequence of SEQ ID NO: 30. In another embodiment, the anti-CD19 ScFv portion of the CAR comprises the amino acid sequence set forth in SEQ ID NO: 38.

In one aspect of the present invention, there is provided a CAR capable of binding to a non-TSA or non-TAA including, for example and not by way of limitation, an antigen derived from Retroviridae (e.g. human immunodeficiency viruses such as HIV-1 and HIV-LP), Picornaviridae (e.g. poliovirus, hepatitis A virus, enterovirus, human coxsackievirus, rhinovirus, and echovirus), rubella virus, coronavirus, vesicular stomatitis virus, rabies virus, ebola virus, parainfluenza virus, mumps virus, measles virus, respiratory syncytial virus, influenza virus, hepatitis B virus, parvovirus, Adenoviridae, Herpesviridae [e.g. type 1 and type 2 herpes simplex virus (HSV), varicella-zoster virus, cytomegalovirus (CMV), and herpes virus], Poxviridae (e.g. smallpox virus, vaccinia virus, and pox virus), or hepatitis C virus, or any combination thereof.

In another aspect of the present invention, there is provided a CAR capable of binding to an antigen derived from a bacterial strain of Staphylococci, *Streptococcus, Escherichia coli, Pseudomonas*, or *Salmonella*. Particularly, there is provided a CAR capable of binding to an antigen derived from an infectious bacterium, for example, *Helicobacter* pyloris, *Legionella* pneumophilia, a bacterial strain of Mycobacteria sps. (e.g. *M. tuberculosis, M. avium, M. intracellulare, M. kansaii*, or *M. gordonea*), *Staphylococcus aureus, Neisseria gonorrhoeae, Neisseria meningitides, Listeria monocytogenes, Streptococcus pyogenes*, Group A *Streptococcus*, Group B *Streptococcus* (*Streptococcus agalactiae*), *Streptococcus pneumoniae*, or *Clostridium tetani*, or a combination thereof.

2. Transmembrane Domain

With respect to the transmembrane domain, the CAR comprises one or more transmembrane domains fused to the extracellular CD33 antigen binding domain of the CAR.

The transmembrane domain may be derived either from a natural or from a synthetic source. Where the source is natural, the domain may be derived from any membrane-bound or transmembrane protein.

Transmembrane regions of particular use in the CARs described herein may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, mesothelin, CD33, CD37, CD64, CD80, CD86, CD134, CD137, CD154. Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

In one embodiment, the transmembrane domain that naturally is associated with one of the domains in the CAR is used in addition to the transmembrane domains described supra.

In some instances, the transmembrane domain can be selected by amino acid substitution to avoid binding of such domains to the transmembrane domains of the same or different surface membrane proteins to minimize interactions with other members of the receptor complex.

In one embodiment, the transmembrane domain in the CAR of the invention is the CD8 transmembrane domain. In one embodiment, the CD8 transmembrane domain comprises the nucleic acid sequence of SEQ ID NO: 27. In one embodiment, the CD8 transmembrane domain comprises the nucleic acid sequence that encodes the amino acid sequence of SEQ ID NO: 28. In another embodiment, the CD8 transmembrane domain comprises the amino acid sequence of SEQ ID NO: 28.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 28, or a sequence with 95-99% identity to an amino acid sequence of SEQ ID NO: 28.

In some instances, the transmembrane domain of the CAR comprises the CD8.alpha.hinge domain. In one embodiment, the CD8 hinge domain comprises the nucleic acid sequence of SEQ ID NO: 29. In one embodiment, the CD8 hinge domain comprises the nucleic acid sequence that encodes the amino acid sequence of SEQ ID NO: 30. In another embodiment, the CD8 hinge domain comprises the amino acid sequence of SEQ ID NO: 30, or a sequence with 95-99% identify thereof.

In one embodiment, an isolated nucleic acid molecule is provided wherein the encoded linker domain is derived from the extracellular domain of CD8, and is linked to the transmembrane CD8 domain, the transmembrane CD28 domain, or a combination thereof.

In one embodiment, the transmembrane domain in the CAR of the invention is the TNFRSF19 transmembrane domain. In one embodiment, the TNFRSF19 transmembrane domain comprises the nucleic acid sequence of SEQ ID NO: 51. In one embodiment, the TNFRSF19 transmembrane domain comprises the nucleic acid sequence that encodes the amino acid sequence of SEQ ID NO: 52. In another embodiment, the TNFRSF19 transmembrane domain comprises the amino acid sequence of SEQ ID NO: 52.

In one embodiment, the encoded transmembrane domain comprises an amino acid sequence having at least one, two or three modifications (e.g., substitutions) but not more than 20, 10 or 5 modifications (e.g., substitutions) of an amino acid sequence of SEQ ID NO: 52, or a sequence with 95-99% identity to an amino acid sequence of SEQ ID NO: 52.

3. Spacer Domain

In the CAR, a spacer domain, also termed hinge domain, can be arranged between the extracellular domain and the transmembrane domain, or between the intracellular domain and the transmembrane domain. The spacer domain means any oligopeptide or polypeptide that serves to link the transmembrane domain with the extracellular domain and/or the transmembrane domain with the intracellular domain. The spacer domain comprises up to 300 amino acids, preferably 10 to 100 amino acids, and most preferably 25 to 50 amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

The spacer domain preferably has a sequence that promotes binding of a CAR with an antigen and enhances signaling into a cell. Examples of an amino acid that is expected to promote the binding include cysteine, a charged amino acid, and serine and threonine in a potential glycosylation site, and these amino acids can be used as an amino acid constituting the spacer domain.

As the spacer domain, the entire or a part of amino acid numbers 118 to 178 (SEQ ID NO: 31) which is a hinge region of CD8.alpha. (NCBI RefSeq: NP.sub.--001759.3), amino acid numbers 135 to 195 of CD8.beta. (GenBank: AAA35664.1), amino acid numbers 315 to 396 of CD4 (NCBI RefSeq: NP.sub.--000607.1), or amino acid numbers 137 to 152 of CD28 (NCBI RefSeq: NP.sub.--006130.1) can be used. Also, as the spacer domain, a part of a constant region of an antibody H chain or L chain (CH1 region or CL region, for example, a peptide having an amino acid sequence shown in SEQ ID NO: 32) can be used. Further, the spacer domain may be an artificially synthesized sequence.

In addition, an entire or a part of amino acids comprising the constant region of a human IgG4 (UniProt ID: P01861), including CH1, (amino acid numbers 1-98), hinge, SEQ ID NO: 80, and the corresponding nucleotide SEQ ID NO:79, (amino acid numbers 99-110), CH2, amino acid SEQ ID NO: 81 and corresponding nucleotide SEQ ID NO: 80, (amino acid numbers 111-220) and CH3, SEQ ID NO:84 and corresponding nucleotide SEQ ID NO: 83, (amino acid numbers 221-327) or a combination thereof, such as IgG4 Hinge CH2 CH3 domain, SEQ ID NO: 86, and the corresponding nucleotide SEQ ID NO: 85, can be used.

In one embodiment, the spacer domain of the CAR comprises the TNFRSF19 hinge domain which comprises the nucleic acid sequence of SEQ ID NO: 53. In one embodiment, the TNFRSF19 hinge domain comprises the nucleic acid sequence that encodes the amino acid sequence of SEQ ID NO: 54. In another embodiment, the TNFRSF19 hinge domain comprises the amino acid sequence of SEQ ID NO: 54, or a sequence with 95-99% identify thereof.

In one embodiment, the spacer domain of the CAR comprises the TNFRSF19 truncated hinge domain comprises the nucleic acid sequence of SEQ ID NO: 55. In one embodiment, the TNFRSF19 truncated hinge domain comprises the nucleic acid sequence that encodes the amino acid sequence of SEQ ID NO: 56. In another embodiment, the TNFRSF19 truncated hinge domain comprises the amino acid sequence of SEQ ID NO: 56, or a sequence with 95-99% identify thereof.

In one embodiment, the TNFRSF19 hinge and transmembrane domains comprise the nucleic acid sequence of SEQ ID NO: 49. In one embodiment, the TNFRSF19 hinge and transmembrane domains comprise the nucleic acid sequence that encodes the amino acid sequence of SEQ ID NO: 50. In another embodiment, the TNFRSF19 hinge and transmembrane domains comprise the amino acid sequence of SEQ ID NO: 50, or a sequence with 95-99% identify thereof.

In one embodiment, a CD8a hinge domain is fused to a TNFRSF19 transmembrane domain comprising the nucleic acid sequence of SEQ ID NO: 57. In one embodiment, the CD8a hinge domain is fused to a TNFRSF19 transmembrane domain comprises the nucleic acid sequence that encodes the amino acid sequence of SEQ ID NO: 58. In another embodiment, the CD8a hinge domain is fused to a TNFRSF19 transmembrane domain comprises the amino acid sequence of SEQ ID NO: 58, or a sequence with 95-99% identify thereof.

Further, in the CAR, a signal peptide sequence, also termed leader peptide, can be linked to the N-terminus. The signal peptide sequence exists at the N-terminus of many secretory proteins and membrane proteins, and has a length of 15 to 30 amino acids. Since many of the protein molecules mentioned above as the intracellular domain have signal peptide sequences, the signal peptides can be used as a signal peptide for the CAR. In one embodiment, the signal peptide comprises the amino acid sequence shown in SEQ ID NO: 14).

In one embodiment, the CD8 alpha leader peptide, is comprising the nucleic acid sequence of SEQ ID NO: 43. In one embodiment, CD8 alpha leader peptide comprises the nucleic acid sequence that encodes the amino acid sequence of SEQ ID NO: 44. In another embodiment, the CD8a hinge domain is fused to a TNFRSF19 transmembrane domain comprises the amino acid sequence of SEQ ID NO: 44, or a sequence with 95-99% identify thereof.

In another embodiment, the GMCSF leader peptide, is comprising the nucleic acid sequence of SEQ ID NO: 39. In one embodiment, the GMCSF leader peptide, comprises the nucleic acid sequence that encodes the amino acid sequence of SEQ ID NO: 40. In another embodiment, the CD8a hinge domain is fused to a TNFRSF19 transmembrane domain comprises the amino acid sequence of SEQ ID NO: 40, or a sequence with 95-99% identify thereof.

In another embodiment, the TNFRSF19 leader peptide is comprising the nucleic acid sequence of SEQ ID NO: 41. In one embodiment, TNFRSF19 leader peptide, and CD8 alpha leader peptide comprises the nucleic acid sequence that encodes the amino acid sequence of SEQ ID NO: 42. In another embodiment, the CD8a hinge domain is fused to a TNFRSF19 transmembrane domain comprises the amino acid sequence of SEQ ID NO: 42, or a sequence with 95-99% identify thereof.

In one embodiment, a tag sequence encoding a truncated sequence of epidermal growth factor receptor (tEGFR) is comprising the nucleic acid sequence of SEQ ID NO: 67. In one embodiment, tEGFR comprises the nucleic acid sequence that encodes the amino acid sequence of SEQ ID NO: 68. In another embodiment, the tEGFR tag comprises the amino acid sequence of SEQ ID NO: 68, or a sequence with 95-99% identify thereof.

In one embodiment, a furin recognition site and downstream T2A self-cleaving peptide sequence, designed for simultaneous bicistronic expression of the tag sequence and the CAR sequence, is comprising the nucleic acid sequence of SEQ ID NO: 65. In one embodiment, furin and T2A sequence comprises the nucleic acid sequence that encodes the amino acid sequence of SEQ ID NO: 66. In another embodiment, the tEGFR tag comprises the amino acid sequence of SEQ ID NO: 66 or a sequence with 95-99% identify thereof.

In one embodiment, an upstream furin recognition site and T2A self-cleaving peptide sequence and a furin recognition downstream site, designed for simultaneous bicistronic expression of the tag sequence and the CAR sequence, is comprising the nucleic acid sequence of SEQ ID NO: 67. In one embodiment, furin and T2A sequence comprises the nucleic acid sequence that encodes the amino acid sequence of SEQ ID NO: 68. In another embodiment, the tEGFR tag comprises the amino acid sequence of SEQ ID NO: 68 or a sequence with 95-99% identify thereof.

In one embodiment, the targeting domain of the CAR is expressed separately in the form of monoclonal antibody, ScFv Fab, Fab'2 and is containing at binding tag or epitope, whereas the effector-cell expressed component of the CAR contains a binding domain specifically directed to bind the tag or epitope expressed on the soluble CAR module, such as specific binding on the soluble component of the CAR to the cell bound component forms the full functional CAR structure.

4. Intracellular Domain

The cytoplasmic domain or otherwise the intracellular signaling domain of the CAR is responsible for activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus, the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Preferred examples of intracellular signaling domains for use in the CAR include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the CARs disclosed herein include those derived from TCR zeta (CD3 Zeta), FcR gamma, FcR beta, CD3 gamma, CD3 delta, CD3 epsilon, CD5, CD22, CD79a, CD79b, and CD66d. Specific, non-limiting examples, of the ITAM include peptides having sequences of amino acid numbers 51 to 164 of CD3.zeta. (NCBI RefSeq: NP.sub.--932170.1), amino acid numbers 45 to 86 of Fc.epsilon.RI.gamma. (NCBI RefSeq: NP.sub.--004097.1), amino acid numbers 201 to 244 of Fc.epsilon-.RI.beta. (NCBI RefSeq: NP.sub.--000130.1), amino acid numbers 139 to 182 of CD3.gamma. (NCBI RefSeq: NP.sub.--000064.1), amino acid numbers 128 to 171 of CD3 delta. (NCBI RefSeq: NP.sub.--000723.1), amino acid numbers 153 to 207 of CD3.epsilon. (NCBI RefSeq: NP.sub.--000724.1), amino acid numbers 402 to 495 of CD5 (NCBI RefSeq: NP.sub.--055022.2), amino acid numbers 707 to 847 of 0022 (NCBI RefSeq: NP.sub.--001762.2), amino acid numbers 166 to 226 of CD79a (NCBI RefSeq: NP.sub.--001774.1), amino acid numbers 182 to 229 of CD79b (NCBI RefSeq: NP.sub.--000617.1), and amino acid numbers 177 to 252 of CD66d (NCBI RefSeq: NP.sub.--001806.2), and their variants having the same function as these peptides have. The amino acid number based on amino acid sequence information of NCBI RefSeq ID or GenBank described herein is numbered based on the full length of the precursor (comprising a signal peptide sequence etc.) of each protein. In one embodiment, the cytoplasmic signaling molecule in the CAR comprises a cytoplasmic signaling sequence derived from CD3 zeta.

In a preferred embodiment, the intracellular domain of the CAR can be designed to comprise the CD3-zeta signaling domain by itself or combined with any other desired cytoplasmic domain(s) useful in the context of the CAR. For example, the intracellular domain of the CAR can comprise a CD3 zeta chain portion and a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such costimulatory molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. Specific, non-limiting examples, of such costimulatory molecules include peptides having sequences of amino acid numbers 236 to 351 of CD2 (NCBI RefSeq: NP.sub.--001758.2), amino acid numbers 421 to 458 of CD4 (NCBI RefSeq: NP.sub.--000607.1), amino acid numbers 402 to 495 of CD5 (NCBI RefSeq: NP.sub.--055022.2), amino acid numbers 207 to 235 of CD8.alpha. (NCBI RefSeq: NP.sub.--001759.3), amino acid numbers 196 to 210 of CD83 (GenBank: AAA35664.1), amino acid numbers 181 to 220 of CD28 (NCBI RefSeq: NP.sub.--006130.1), amino acid numbers 214 to 255 of CD137 (4-1BB, NCBI RefSeq: NP.sub.--001552.2), amino acid numbers 241 to 277 of CD134 (OX40, NCBI RefSeq: NP.sub.--003318.1), and amino acid numbers 166 to 199 of ICOS (NCBI RefSeq: NP.sub.--036224.1), and their variants having the same function as these peptides have. Thus, while the disclosure herein is exemplified primarily with 4-1BB as the co-stimulatory signaling element, other costimulatory elements are within the scope of the disclosure.

The cytoplasmic signaling sequences within the cytoplasmic signaling portion of the CAR may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the intracellular domain is designed to comprise the signaling domain of CD3-zeta and the signaling domain of CD28. In another embodiment, the intracellular domain is designed to comprise the signaling domain of CD3-zeta and the signaling domain of 4-1BB. In yet another embodiment, the intracellular domain is designed to comprise the signaling domain of CD3-zeta and the signaling domain of CD28 and 4-1BB.

In one embodiment, the intracellular domain in the CAR is designed to comprise the signaling domain of 4-1BB and the signaling domain of CD3-zeta, wherein the signaling domain of 4-1BB comprises the nucleic acid sequence set forth in SEQ ID NO: 33, SEQ ID NO: 45, or SEQ ID NO: 59, respectively and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of 4-1BB and the signaling domain of CD3-zeta, wherein the signaling domain of 4-1BB comprises the nucleic acid sequence that encodes the amino acid sequence of SEQ ID NO: 34, SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of 4-1BB and the signaling domain of CD3-zeta, wherein the signaling domain of 4-1BB comprises the amino acid sequence set forth in SEQ ID NO: 34, SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

In one embodiment, the intracellular domain in the CAR is designed to comprise the signaling domain of CD28 and the signaling domain of CD3-zeta, wherein the signaling domain of CD28 comprises the nucleic acid sequence set forth in SEQ ID NO: 45, or SEQ ID NO: 59, respectively, and the signaling domain of CD3-zeta comprises the nucleic acid sequence set forth in SEQ ID NO: 35, SEQ ID NO: 47, or SEQ ID NO: 61, respectively.

In one embodiment, the intracellular domain in the CAR is designed to comprise the signaling domain of CD28 and the signaling domain of CD3-zeta, wherein the signaling domain of CD28 comprises the nucleic acid sequence that encodes the amino acid sequence of SEQ ID NO: 46, or SEQ ID NO: 60, respectively and the signaling domain of CD3-zeta comprises the nucleic acid sequence that encodes the amino acid sequence of SEQ ID NO: 36, or SEQ ID NO: 48, or SEQ ID NO: 62.

In one embodiment, the intracellular domain in the CAR is designed to comprise the signaling domain of CD28 and the signaling domain of CD3-zeta, wherein the signaling domain of CD28 comprises the amino acid sequence set forth in SEQ ID NO: 46, or SEQ ID NO: 60, respectively and the signaling domain of CD3-zeta comprises the amino acid sequence set forth in SEQ ID NO: 36, SEQ ID NO: 48, or SEQ ID NO: 62, respectively.

5. Additional Description of CARs

Also expressly included within the scope of the invention are functional portions of the CARs disclosed herein. The term "functional portion" when used in reference to a CAR refers to any part or fragment of one or more of the CARs disclosed herein, which part or fragment retains the biological activity of the CAR of which it is a part (the parent CAR). Functional portions encompass, for example, those parts of a CAR that retain the ability to recognize target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function of the functional portion, e.g., recognize target cells, detect cancer, treat or prevent cancer, etc. More desirably, the additional amino acids enhance the biological activity, as compared to the biological activity of the parent CAR.

Included in the scope of the disclosure are functional variants of the CARs disclosed herein. The term "functional variant" as used herein refers to a CAR, polypeptide, or protein having substantial or significant sequence identity or similarity to a parent CAR, which functional variant retains the biological activity of the CAR of which it is a variant. Functional variants encompass, for example, those variants of the CAR described herein (the parent CAR) that retain the ability to recognize target cells to a similar extent, the same extent, or to a higher extent, as the parent CAR. In reference to the parent CAR, the functional variant can, for instance, be at least about 30%, 50%, 75%, 80%, 90%, 98% or more identical in amino acid sequence to the parent CAR.

A functional variant can, for example, comprise the amino acid sequence of the parent CAR with at least one conservative amino acid substitution. Alternatively or additionally, the functional variants can comprise the amino acid sequence of the parent CAR with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent CAR.

Amino acid substitutions of the CARs are preferably conservative amino acid substitutions. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic/negatively charged polar amino acid substituted for another acidic/negatively charged polar amino acid (e.g., Asp or Glu), an amino acid with a nonpolar side chain substituted for another amino acid with a nonpolar side chain (e.g., Ala, Gly, Val, He, Leu, Met, Phe, Pro, Trp, Cys, Val, etc.), a basic/positively charged polar amino acid substituted for another basic/positively charged polar amino acid (e.g. Lys, His, Arg, etc.), an uncharged amino acid with a polar side chain substituted for another uncharged amino acid with a polar side chain (e.g., Asn, Gin, Ser, Thr, Tyr, etc.), an amino acid with a beta-branched side-chain substituted for another amino acid with a beta-branched side-chain (e.g., He, Thr, and Val), an amino acid with an aromatic side-chain substituted for another amino acid with an aromatic side chain (e.g., His, Phe, Trp, and Tyr), etc.

The CAR can consist essentially of the specified amino acid sequence or sequences described herein, such that other components, e.g., other amino acids, do not materially change the biological activity of the functional variant.

The CARs (including functional portions and functional variants) can be of any length, i.e., can comprise any number of amino acids, provided that the CARs (or functional portions or functional variants thereof) retain their biological activity, e.g., the ability to specifically bind to antigen, detect diseased cells in a mammal, or treat or prevent disease in a mammal, etc. For example, the CAR can be about 50 to about 5000 amino acids long, such as 50, 70, 75, 100, 125, 150, 175, 200, 300, 400, 500, 600, 700, 800, 900, 1000 or more amino acids in length.

The CARs (including functional portions and functional variants of the invention) can comprise synthetic amino acids in place of one or more naturally-occurring amino acids. Such synthetic amino acids are known in the art, and include, for example, aminocyclohexane carboxylic acid, norleucine, -amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, a-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, -aminocyclopentane carboxylic acid, a-aminocyclohexane carboxylic acid, a-aminocycloheptane carboxylic acid, a-(2-amino-2-norbomane)-carboxylic acid, γ-diaminobutyric acid, β-diaminopropionic acid, homophenylalanine, and a-tert-butylglycine.

The CARs (including functional portions and functional variants) can be glycosylated, amidated, carboxylated, phosphorylated, esterified, N-acylated, cyclized via, e.g., a disulfide bridge, or converted into an acid addition salt and/or optionally dimerized or polymerized, or conjugated.

The CARs (including functional portions and functional variants thereof) can be obtained by methods known in the art. The CARs may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001; and U.S. Pat. No. 5,449,752. Also, polypeptides and proteins can be recombinantly produced using the nucleic acids described herein using standard recombinant methods. See, for instance, Sambrook et al., Molecular Cloning: A Laboratory Manual, 3rd ed., Cold Spring Harbor Press, Cold Spring Harbor, NY 2001; and Ausubel et al., Current Protocols in Molecular Biology, Greene Publishing Associates and John Wiley & Sons, NY, 1994. Further, some of the CARs (including functional portions and functional variants thereof) can be isolated and/or purified from a source, such as a plant, a bacterium, an insect, a mammal, e.g., a rat, a human, etc. Methods of isolation and purification are well-known in the art. Alternatively, the CARs described herein (including functional portions and functional variants thereof) can be commercially synthesized by companies. In this respect, the CARs can be synthetic, recombinant, isolated, and/or purified.

B. Antibodies and Antigen Binding Fragments

One embodiment further provides a CAR, a T cell expressing a CAR, an antibody, or antigen binding domain or portion thereof, which specifically binds to one or more of the antigens disclosed herein. As used herein, a "T cell expressing a CAR," or a "CAR T cell" means a T cell expressing a CAR, and has antigen specificity determined by, for example, the antibody-derived targeting domain of the CAR.

As used herein, and "antigen binding domain" can include an antibody and antigen binding fragments thereof. The term "antibody" is used herein in the broadest sense and encompasses various antibody structures, including but not limited to monoclonal antibodies, polyclonal antibodies, multi-specific antibodies (e.g., bispecific antibodies), and antigen binding fragments thereof, so long as they exhibit the desired antigen-binding activity. Non-limiting examples of antibodies include, for example, intact immunoglobulins and variants and fragments thereof known in the art that retain binding affinity for the antigen.

A "monoclonal antibody" is an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic epitope. The modifier "monoclonal" indicates the character of the antibody as being obtained from a substantially homogeneous population of antibodies, and is not to be construed as requiring production of the antibody by any particular method. In some examples, a monoclonal antibody is an antibody produced by a single clone of B lymphocytes or by a cell into which nucleic acid encoding the light and heavy variable regions of the antibody of a single antibody (or an antigen binding fragment thereof) have been transfected, or a progeny thereof. In some examples monoclonal antibodies are isolated from a subject. Monoclonal antibodies can have conservative amino acid substitutions which have substantially no effect on antigen binding or other immunoglobulin functions. Exemplary methods of production of monoclonal antibodies are known, for example, see Harlow & Lane, Antibodies, A Laboratory Manual, 2nd ed. Cold Spring Harbor Publications, New York (2013).

Typically, an immunoglobulin has heavy (H) chains and light (L) chains interconnected by disulfide bonds. Immunoglobulin genes include the kappa, lambda, alpha, gamma, delta, epsilon and mu constant region genes, as well as the myriad immunoglobulin variable domain genes. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region (or constant domain) and a variable region (or variable domain; see, e.g., Kindt et al. Kuby Immunology, 6th ed., W.H. Freeman and Co., page 91 (2007).) In several embodiments, the heavy and the light chain variable regions combine to specifically bind the antigen. In additional embodiments, only the heavy chain variable region is required. For example, naturally occurring camelid antibodies consisting of a heavy chain only are functional and stable in the absence of light chain (see, e.g., Hamers-Casterman et al., Nature, 363:446-448, 1993; Sheriff et al., Nat. Struct. Biol., 3:733-736, 1996). References to "VH" or "VH" refer to the variable region of an antibody heavy chain, including that of an antigen binding fragment, such as Fv, ScFv, dsFv or Fab. References to "VL" or "VL" refer to the variable domain of an antibody light chain, including that of an Fv, ScFv, dsFv or Fab.

Light and heavy chain variable regions contain a "framework" region interrupted by three hypervariable regions, also called "complementarity-determining regions" or "CDRs" (see, e.g., Kabat et al., Sequences of Proteins of Immunological Interest, U.S. Department of Health and Human Services, 1991). The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The amino acid sequence boundaries of a given CDR can be readily determined using any of a number of well-known schemes, including those described by Kabat et al. ("Sequences of Proteins of Immunological Interest," 5th Ed. Public Health Service, National Institutes of Health, Bethesda, MD, 1991; "Kabat" numbering scheme), Al-Lazikani et al., (JMB 273,927-948, 1997; "Chothia" numbering scheme), and Lefranc et al. ("IMGT unique numbering for immunoglobulin and T cell receptor variable domains and Ig superfamily V-like domains," Dev. Comp. Immunol., 27:55-77, 2003; "IMGT" numbering scheme). The CDRs of each chain are typically referred to as CDR1, CDR2, and CDR3 (from the N-terminus to C-terminus), and are also typically identified by the chain in which the particular CDR is located. Thus, a VH CDR3 is the CDR3 from the variable domain of the heavy chain of the antibody in which it is found, whereas a VL CDR1 is the CDR1 from the variable domain of the light chain of the antibody in which it is found. Light chain CDRs are sometimes referred to as LCDR1, LCDR2, and LCDR3. Heavy chain CDRs are sometimes referred to as HCDR1, HCDR2, and HCDR3.

An "antigen binding fragment" is a portion of a full length antibody that retains the ability to specifically recognize the cognate antigen, as well as various combinations of such portions. Non-limiting examples of antigen binding fragments include Fv, Fab, Fab', Fab'-SH, F(ab')2; diabodies; linear antibodies; single-chain antibody molecules (e.g. ScFv); and multi-specific antibodies formed from antibody fragments. Antibody fragments include antigen binding fragments either produced by the modification of whole antibodies or those synthesized de novo using recombinant DNA methodologies (see, e.g., Kontermann and Dubel (Ed), Antibody Engineering, Vols. 1-2, 2nd Ed., Springer Press, 2010).

A single-chain antibody (ScFv) is a genetically engineered molecule containing the VH and VL domains of one or more antibody(ies) linked by a suitable polypeptide linker as a genetically fused single chain molecule (see, for example, Bird et al., Science, 242:423 426, 1988; Huston et al., Proc. Natl. Acad. Sci., 85:5879 5883, 1988; Ahmad et al., Clin. Dev. Immunol., 2012, doi:10.1155/2012/980250; Marbry, IDrugs, 13:543-549, 2010). The intramolecular orientation of the VH-domain and the VL-domain in a ScFv, is typically not decisive for ScFvs. Thus, ScFvs with both possible arrangements (VH-domain-linker domain-VL-domain; VL-domain-linker domain-VH-domain) may be used.

In a dsFv, the heavy and light chain variable chains have been mutated to introduce a disulfide bond to stabilize the association of the chains. Diabodies also are included, which are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see, for example, Holliger et al., Proc. Natl. Acad. Sci., 90:6444 6448, 1993; Poljak et al., Structure, 2:1121 1123, 1994).

Antibodies also include genetically engineered forms such as chimeric antibodies (such as humanized murine antibodies) and heteroconjugate antibodies (such as bispecific antibodies). See also, Pierce Catalog and Handbook, 1994-1995 (Pierce Chemical Co., Rockford, IL); Kuby, J., Immunology, 3rd Ed., W.H. Freeman & Co., New York, 1997.

Non-naturally occurring antibodies can be constructed using solid phase peptide synthesis, can be produced recombinantly, or can be obtained, for example, by screening combinatorial libraries consisting of variable heavy chains and variable light chains as described by Huse et al., Science 246:1275-1281 (1989), which is incorporated herein by reference. These and other methods of making, for example, chimeric, humanized, CDR-grafted, single chain, and bifunctional antibodies, are well known to those skilled in the art (Winter and Harris, Immunol. Today 14:243-246 (1993); Ward et al., Nature 341:544-546 (1989); Harlow and Lane, supra, 1988; Hilyard et al., Protein Engineering: A practical approach (IRL Press 1992); Borrabeck, Antibody Engineering, 2d ed. (Oxford University Press 1995); each of which is incorporated herein by reference).

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. Antibody competition assays are known, and an exemplary competition assay is provided herein.

A "humanized" antibody or antigen binding fragment includes a human framework region and one or more CDRs from a non-human (such as a mouse, rat, or synthetic) antibody or antigen binding fragment. The non-human antibody or antigen binding fragment providing the CDRs is termed a "donor," and the human antibody or antigen binding fragment providing the framework is termed an "acceptor." In one embodiment, all the CDRs are from the donor immunoglobulin in a humanized immunoglobulin. Constant regions need not be present, but if they are, they can be substantially identical to human immunoglobulin constant regions, such as at least about 85-90%, such as about 95% or more identical. Hence, all parts of a humanized antibody or antigen binding fragment, except possibly the CDRs, are substantially identical to corresponding parts of natural human antibody sequences.

A "chimeric antibody" is an antibody which includes sequences derived from two different antibodies, which typically are of different species. In some examples, a chimeric antibody includes one or more CDRs and/or framework regions from one human antibody and CDRs and/or framework regions from another human antibody.

A "fully human antibody" or "human antibody" is an antibody which includes sequences from (or derived from) the human genome, and does not include sequence from another species. In some embodiments, a human antibody includes CDRs, framework regions, and (if present) an Fc region from (or derived from) the human genome. Human antibodies can be identified and isolated using technologies for creating antibodies based on sequences derived from the human genome, for example by phage display or using transgenic animals (see, e.g., Barbas et al. Phage display: A Laboratory Manuel. 1st Ed. New York: Cold Spring Harbor Laboratory Press, 2004. Print.; Lonberg, Nat. Biotech., 23: 1117-1125, 2005; Lonenberg, Curr. Opin. Immunol., 20:450-459, 2008).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a bispecific or bifunctional antibody has two different binding sites.

Methods of testing antibodies for the ability to bind to any functional portion of the CAR are known in the art and include any antibody-antigen binding assay, such as, for example, radioimmunoassay (RIA), ELISA, Western blot, immunoprecipitation, and competitive inhibition assays (see, e.g., Janeway et al., infra, U.S. Patent Application Publication No. 2002/0197266 A1, and U.S. Pat. No. 7,338,929).

Also, a CAR, a T cell expressing a CAR, an antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

C. Conjugates

A CAR, a T cell expressing a CAR, or monoclonal antibodies, or antigen binding fragments thereof, specific for one or more of the antigens disclosed herein, can be conjugated to an agent, such as an effector molecule or detectable marker, using any number of means known to those of skill in the art. Both covalent and noncovalent attachment means may be used. Conjugates include, but are not limited to, molecules in which there is a covalent linkage of an effector molecule or a detectable marker to an antibody or antigen binding fragment that specifically binds one or more of the antigens disclosed herein. One of skill in the art will appreciate that various effector molecules and detectable markers can be used, including (but not limited to) chemotherapeutic agents, anti-angiogenic agents, toxins, radioactive agents such as $^{125}I$, $^{32}P$, $^{14}C$, $^{3}H$ and $^{35}S$ and other labels, target moieties and ligands, etc.

The choice of a particular effector molecule or detectable marker depends on the particular target molecule or cell, and the desired biological effect. Thus, for example, the effector molecule can be a cytotoxin that is used to bring about the death of a particular target cell (such as a tumor cell).

The procedure for attaching an effector molecule or detectable marker to an antibody or antigen binding fragment varies according to the chemical structure of the effector. Polypeptides typically contain a variety of functional groups; such as carboxylic acid (COOH), free amine (—$NH_2$) or sulfhydryl (—SH) groups, which are available for reaction with a suitable functional group on an antibody to result in the binding of the effector molecule or detectable marker. Alternatively, the antibody or antigen binding fragment is derivatized to expose or attach additional reactive functional groups. The derivatization may involve attachment of any of a number of known linker molecules such as those available from Pierce Chemical Company, Rockford, IL. The linker can be any molecule used to join the antibody or antigen binding fragment to the effector molecule or detectable marker. The linker is capable of forming covalent bonds to both the antibody or antigen binding fragment and to the effector molecule or detectable marker. Suitable linkers are well known to those of skill in the art and include, but are not limited to, straight or branched-chain carbon linkers, heterocyclic carbon linkers, or peptide linkers. Where the antibody or antigen binding fragment and the effector molecule or detectable marker are polypeptides, the linkers may be joined to the constituent amino acids through their side groups (such as through a disulfide linkage to cysteine) or to the alpha carbon amino and carboxyl groups of the terminal amino acids.

In several embodiments, the linker can include a spacer element, which, when present, increases the size of the linker such that the distance between the effector molecule or the detectable marker and the antibody or antigen binding fragment is increased. Exemplary spacers are known to the person of ordinary skill, and include those listed in U.S. Pat. Nos. 7,964,5667, 498,298, 6,884,869, 6,323,315, 6,239,104, 6,034,065, 5,780,588, 5,665,860, 5,663,149, 5,635,483, 5,599,902, 5,554,725, 5,530,097, 5,521,284, 5,504,191, 5,410,024, 5,138,036, 5,076,973, 4,986,988, 4,978,744, 4,879,278, 4,816,444, and 4,486,414, as well as U.S. Pat. Pub. Nos. 20110212088 and 20110070248, each of which is incorporated by reference herein in its entirety.

In some embodiments, the linker is cleavable under intracellular conditions, such that cleavage of the linker releases the effector molecule or detectable marker from the antibody or antigen binding fragment in the intracellular environment. In yet other embodiments, the linker is not cleavable and the effector molecule or detectable marker is released, for example, by antibody degradation. In some embodiments, the linker is cleavable by a cleaving agent that is present in the intracellular environment (for example, within a lysosome or endosome or caveolea). The linker can be, for example, a peptide linker that is cleaved by an intracellular peptidase or protease enzyme, including, but not limited to, a lysosomal or endosomal protease. In some embodiments, the peptide linker is at least two amino acids long or at least three amino acids long. However, the linker can be 4, 5, 6, 7, 8, 9, 10, 11, 12, 13, 14 or 15 amino acids long, such as 1-2, 1-3, 2-5, 3-10, 3-15, 1-5, 1-10, 1-15 amino acids long. Proteases can include cathepsins B and D and plasmin, all of which are known to hydrolyze dipeptide drug derivatives resulting in the release of active drug inside target cells (see, for example, Dubowchik and Walker, 1999, Pharm. Therapeutics 83:67-123). For example, a peptide linker that is cleavable by the thiol-dependent protease cathepsin-B, can be used (for example, a Phenylalanine-Leucine or a Glycine-Phenylalanine-Leucine-Glycine linker). Other examples of such linkers are described, for example, in U.S. Pat. No. 6,214,345, incorporated herein by reference. In a specific embodiment, the peptide linker cleavable by an intracellular protease is a Valine-Citruline linker or a Phenylalanine-Lysine linker (see, for example, U.S. Pat. No. 6,214,345, which describes the synthesis of doxorubicin with the Valine-Citruline linker).

In other embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (for example, a hydrazone, semicarbazone, thiosemicarbazone, cis-aconitic amide, orthoester, acetal, ketal, or the like) can be used. (See, for example, U.S. Pat. Nos. 5,122,368; 5,824,805; 5,622,929; Dubowchik and Walker, 1999, Pharm. Therapeutics 83:67-123; Neville et al., 1989, Biol. Chem. 264:14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, for example, a thioether attached to the therapeutic agent via an acylhydrazone bond (see, for example, U.S. Pat. No. 5,622,929).

In other embodiments, the linker is cleavable under reducing conditions (for example, a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene)-, SPDB and SMPT. (See, for example, Thorpe et al., 1987, Cancer Res. 47:5924-5931; Wawrzynczak et al., In Immunoconjugates: Antibody Conjugates in Radioimagery and Therapy of Cancer (C. W. Vogel ed., Oxford U. Press, 1987); Phillips et al., Cancer Res. 68:92809290, 2008). See also U.S. Pat. No. 4,880,935.) In yet other specific embodiments, the linker is a malonate linker (Johnson et al., 1995, Anticancer Res. 15:1387-93), a maleimidobenzoyl linker (Lau et al., 1995, Bioorg-Med-Chem. 3(10):1299-1304), or a 3'-N-amide analog (Lau et al., 1995, Bioorg-Med-Chem. 3(10):1305-12).

In yet other embodiments, the linker is not cleavable and the effector molecule or detectable marker is released by antibody degradation. (See U.S. Publication No. 2005/0238649 incorporated by reference herein in its entirety).

In several embodiments, the linker is resistant to cleavage in an extracellular environment. For example, no more than about 20%, no more than about 15%, no more than about 10%, no more than about 5%, no more than about 3%, or no more than about 1% of the linkers, in a sample of conjugate, are cleaved when the conjugate is present in an extracellular environment (for example, in plasma). Whether or not a linker is resistant to cleavage in an extracellular environment can be determined, for example, by incubating the conjugate containing the linker of interest with plasma for a predetermined time period (for example, 2, 4, 8, 16, or 24 hours) and then quantitating the amount of free effector molecule or detectable marker present in the plasma. A variety of exemplary linkers that can be used in conjugates are described in WO 2004-010957, U.S. Publication No. 2006/0074008, U.S. Publication No. 20050238649, and U.S. Publication No. 2006/0024317, each of which is incorporated by reference herein in its entirety.

In several embodiments, conjugates of a CAR, a T cell expressing a CAR, an antibody, or antigen binding portion thereof, and one or more small molecule toxins, such as a calicheamicin, maytansinoids, dolastatins, auristatins, a trichothecene, and CC1065, and the derivatives of these toxins that have toxin activity, are provided.

Maytansine compounds suitable for use as maytansinoid toxin moieties are well known in the art, and can be isolated from natural sources according to known methods, produced using genetic engineering techniques (see Yu et al. (2002) PNAS 99:7968-7973), or maytansinol and maytansinol analogues prepared synthetically according to known methods. Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, each of which is incorporated herein by reference. Conjugates containing maytansinoids, methods of making same, and their therapeutic use are disclosed, for example, in U.S. Pat. Nos. 5,208,020; 5,416,064; 6,441,163 and European Patent EP 0 425 235 B1, the disclosures of which are hereby expressly incorporated by reference.

Additional toxins can be employed with a CAR, a T cell expressing a CAR, an antibody, or antigen binding portion thereof. Exemplary toxins include *Pseudomonas* exotoxin (PE), ricin, abrin, diphtheria toxin and subunits thereof, ribotoxin, ribonuclease, saporin, and calicheamicin, as well as botulinum toxins A through F. These toxins are well known in the art and many are readily available from commercial sources (for example, Sigma Chemical Company, St. Louis, MO). Contemplated toxins also include variants of the toxins (see, for example, U.S. Pat. Nos. 5,079,163 and 4,689,401).

Saporin is a toxin derived from *Saponaria officinalis* that disrupts protein synthesis by inactivating the 60S portion of the ribosomal complex (Stirpe et al., Bio/Technology, 10:405-412, 1992). However, the toxin has no mechanism for specific entry into cells, and therefore requires conjugation to an antibody or antigen binding fragment that recognizes a cell-surface protein that is internalized in order to be efficiently taken up by cells.

Diphtheria toxin is isolated from *Corynebacterium diphtheriae*. Typically, diphtheria toxin for use in immunotoxins is mutated to reduce or to eliminate non-specific toxicity. A mutant known as CRM107, which has full enzymatic activity but markedly reduced non-specific toxicity, has been known since the 1970's (Laird and Groman, J. Virol. 19:220, 1976), and has been used in human clinical trials. See, U.S. Pat. Nos. 5,792,458 and 5,208,021.

Ricin is the lectin RCA60 from *Ricinus communis* (Castor bean). For examples of ricin, see, U.S. Pat. Nos. 5,079,163 and 4,689,401. *Ricinus communis* agglutinin (RCA) occurs in two forms designated $RCA_{60}$ and $RCA_{120}$ according to their molecular weights of approximately 65 and 120 kD, respectively (Nicholson & Blaustein, J. Biochim. Biophys. Acta 266:543, 1972). The A chain is responsible for inactivating protein synthesis and killing cells. The B chain binds ricin to cell-surface galactose residues and facilitates transport of the A chain into the cytosol (Olsnes et al., Nature 249:627-631, 1974 and U.S. Pat. No. 3,060,165).

Ribonucleases have also been conjugated to targeting molecules for use as immunotoxins (see Suzuki et al., Nat. Biotech. 17:265-70, 1999). Exemplary ribotoxins such as α-sarcin and restrictocin are discussed in, for example Rathore et al., Gene 190:31-5, 1997; and Goyal and Batra, Biochem. 345 Pt 2:247-54, 2000. Calicheamicins were first isolated from *Micromonospora echinospora* and are members of the enediyne antitumor antibiotic family that cause double strand breaks in DNA that lead to apoptosis (see, for example Lee et al., J. Antibiot. 42:1070-87, 1989). The drug is the toxic moiety of an immunotoxin in clinical trials (see, for example, Gillespie et al., Ann. Oncol. 11:735-41, 2000).

Abrin includes toxic lectins from *Abrus precatorius*. The toxic principles, abrin a, b, c, and d, have a molecular weight of from about 63 and 67 kD and are composed of two disulfide-linked polypeptide chains A and B. The A chain inhibits protein synthesis; the B chain (abrin-b) binds to D-galactose residues (see, Funatsu et al., Agr. Biol. Chem. 52:1095, 1988; and Olsnes, Methods Enzymol. 50:330-335, 1978).

A CAR, a T cell expressing a CAR, monoclonal antibodies, antigen binding fragments thereof, specific for one or more of the antigens disclosed herein, can also be conjugated with a detectable marker; for example, a detectable marker capable of detection by ELISA, spectrophotometry, flow cytometry, microscopy or diagnostic imaging techniques (such as computed tomography (CT), computed axial tomography (CAT) scans, magnetic resonance imaging (MRI), nuclear magnetic resonance imaging NMRI), magnetic resonance tomography (MTR), ultrasound, fiberoptic examination, and laparoscopic examination). Specific, non-limiting examples of detectable markers include fluorophores, chemiluminescent agents, enzymatic linkages, radioactive isotopes and heavy metals or compounds (for example super paramagnetic iron oxide nanocrystals for detection by MRI). For example, useful detectable markers include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, Green fluorescent protein (GFP), Yellow fluorescent protein (YFP). A CAR, a T cell expressing a CAR, an antibody, or antigen binding portion thereof, can also be conjugated with enzymes that are useful for detection, such as horseradish peroxidase, β-galactosidase, luciferase, alkaline phosphatase, glucose oxidase and the like. When a CAR, a T cell expressing a CAR, an antibody, or antigen binding portion thereof, is conjugated with a detectable enzyme, it can be detected by adding additional reagents that the enzyme uses to produce a reaction product that can be discerned. For example, when the agent horseradish peroxidase is present the addition of hydrogen peroxide and diaminobenzidine leads to a colored reaction product, which is visually detectable. A CAR, a T cell expressing a CAR, an antibody, or antigen binding portion thereof, may also be conjugated with biotin, and detected through indirect measurement of avidin or streptavidin binding. It should be noted that the avidin itself can be conjugated with an enzyme or a fluorescent label.

A CAR, a T cell expressing a CAR, an antibody, or antigen binding portion thereof, may be conjugated with a paramagnetic agent, such as gadolinium. Paramagnetic agents such as superparamagnetic iron oxide are also of use as labels. Antibodies can also be conjugated with lanthanides (such as europium and dysprosium), and manganese. An antibody or antigen binding fragment may also be labeled with a predetermined polypeptide epitopes recognized by a secondary reporter (such as leucine zipper pair sequences, binding sites for secondary antibodies, metal binding domains, epitope tags).

A CAR, a T cell expressing a CAR, an antibody, or antigen binding portion thereof, can also be conjugated with a radiolabeled amino acid. The radiolabel may be used for both diagnostic and therapeutic purposes. For instance, the radiolabel may be used to detect one or more of the antigens disclosed herein and antigen expressing cells by x-ray, emission spectra, or other diagnostic techniques. Further, the radiolabel may be used therapeutically as a toxin for treatment of tumors in a subject, for example for treatment of a neuroblastoma. Examples of labels for polypeptides include, but are not limited to, the following radioisotopes or radionucleotides: $^{3}H$, $^{14}C$, $^{15}N$, $^{35}S$, $^{90}Y$, $^{99}Tc$, $^{111}In$, $^{125}I$, $^{131}I$.

Means of detecting such detectable markers are well known to those of skill in the art. Thus, for example, radiolabels may be detected using photographic film or scintillation counters, fluorescent markers may be detected using a photodetector to detect emitted illumination. Enzymatic labels are typically detected by providing the enzyme with a substrate and detecting the reaction product produced by the action of the enzyme on the substrate, and colorimetric labels are detected by simply visualizing the colored label.

D. Nucleotides, Expression, Vectors, and Host Cells

Further provided by an embodiment of the invention is a nucleic acid comprising a nucleotide sequence encoding any of the CARs, an antibody, or antigen binding portion thereof, described herein (including functional portions and functional variants thereof). The nucleic acids of the invention may comprise a nucleotide sequence encoding any of the leader sequences, antigen binding domains, transmembrane domains, and/or intracellular T cell signaling domains described herein.

In some embodiments, the nucleotide sequence may be codon-modified. Without being bound to a particular theory, it is believed that codon optimization of the nucleotide sequence increases the translation efficiency of the mRNA transcripts. Codon optimization of the nucleotide sequence may involve substituting a native codon for another codon that encodes the same amino acid, but can be translated by tRNA that is more readily available within a cell, thus increasing translation efficiency. Optimization of the nucleotide sequence may also reduce secondary mRNA structures that would interfere with translation, thus increasing translation efficiency.

In an embodiment of the invention, the nucleic acid may comprise a codon-modified nucleotide sequence that encodes the antigen binding domain of the inventive CAR. In another embodiment of the invention, the nucleic acid may comprise a codon-modified nucleotide sequence that encodes any of the CARs described herein (including functional portions and functional variants thereof).

"Nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. In some embodiments, the nucleic acid does not comprise any insertions, deletions, inversions, and/or substitutions. However, it may be suitable in some instances, as discussed herein, for the nucleic acid to comprise one or more insertions, deletions, inversions, and/or substitutions.

A recombinant nucleic acid may be one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques, such as those described in Sambrook et al., supra. The nucleic acids can be constructed based on chemical synthesis and/or enzymatic ligation reactions using procedures known in the art. See, for example, Sambrook et al., supra, and Ausubel et al., supra. For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, IA, USA).

The nucleic acid can comprise any isolated or purified nucleotide sequence which encodes any of the CARs or functional portions or functional variants thereof. Alternatively, the nucleotide sequence can comprise a nucleotide sequence which is degenerate to any of the sequences or a combination of degenerate sequences.

An embodiment also provides an isolated or purified nucleic acid comprising a nucleotide sequence which is complementary to the nucleotide sequence of any of the nucleic acids described herein or a nucleotide sequence which hybridizes under stringent conditions to the nucleotide sequence of any of the nucleic acids described herein.

The nucleotide sequence which hybridizes under stringent conditions may hybridize under high stringency conditions. By "high stringency conditions" is meant that the nucleotide sequence specifically hybridizes to a target sequence (the nucleotide sequence of any of the nucleic acids described herein) in an amount that is detectably stronger than non-specific hybridization. High stringency conditions include conditions which would distinguish a polynucleotide with an exact complementary sequence, or one containing only a few scattered mismatches from a random sequence that happened to have a few small regions (e.g., 3-10 bases) that matched the nucleotide sequence. Such small regions of complementarity are more easily melted than a full-length complement of 14-17 or more bases, and high stringency hybridization makes them easily distinguishable. Relatively high stringency conditions would include, for example, low salt and/or high temperature conditions, such as provided by about 0.02-0.1 M NaCl or the equivalent, at temperatures of about 50-70° C. Such high stringency conditions tolerate little, if any, mismatch between the nucleotide sequence and the template or target strand, and are particularly suitable for detecting expression of any of the inventive CARs. It is generally appreciated that conditions can be rendered more stringent by the addition of increasing amounts of formamide.

Also provided is a nucleic acid comprising a nucleotide sequence that is at least about 70% or more, e.g., about 80%, about 90%, about 91%, about 92%, about 93%, about 94%, about 95%, about 96%, about 97%, about 98%, or about 99% identical to any of the nucleic acids described herein.

In an embodiment, the nucleic acids can be incorporated into a recombinant expression vector. In this regard, an embodiment provides recombinant expression vectors comprising any of the nucleic acids. For purposes herein, the term "recombinant expression vector" means a genetically-modified oligonucleotide or polynucleotide construct that permits the expression of an mRNA, protein, polypeptide, or peptide by a host cell, when the construct comprises a nucleotide sequence encoding the mRNA, protein, polypeptide, or peptide, and the vector is contacted with the cell under conditions sufficient to have the mRNA, protein, polypeptide, or peptide expressed within the cell. The vectors are not naturally-occurring as a whole.

However, parts of the vectors can be naturally-occurring. The recombinant expression vectors can comprise any type of nucleotides, including, but not limited to DNA and RNA, which can be single-stranded or double-stranded, synthesized or obtained in part from natural sources, and which can contain natural, non-natural or altered nucleotides. The recombinant expression vectors can comprise naturally-occurring or non-naturally-occurring internucleotide linkages, or both types of linkages. Preferably, the non-naturally occurring or altered nucleotides or internucleotide linkages do not hinder the transcription or replication of the vector.

In an embodiment, the recombinant expression vector can be any suitable recombinant expression vector, and can be used to transform or transfect any suitable host cell. Suitable vectors include those designed for propagation and expansion or for expression or both, such as plasmids and viruses. The vector can be selected from the group consisting of the pUC series (Fermentas Life Sciences, Glen Burnie, MD), the pBluescript series (Stratagene, LaJolla, CA), the pET series (Novagen, Madison, WI), the pGEX series (Pharmacia Biotech, Uppsala, Sweden), and the pEX series (Clontech, Palo Alto, CA).

Bacteriophage vectors, such as λΰTIO, λϋTI 1, λZapII (Stratagene), EMBL4, and λNMI 149, also can be used. Examples of plant expression vectors include pBIO1, pBI101.2, pBHO1.3, pBI121 and pBIN19 (Clontech). Examples of animal expression vectors include pEUK-Cl, pMAM, and pMAMneo (Clontech). The recombinant expression vector may be a viral vector, e.g., a retroviral vector or a lentiviral vector. A lentiviral vector is a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include, for example, and not by way of limitation, the LENTIVECTOR® gene delivery technology from Oxford BioMedica plc, the LENTIMAX™ vector system from Lentigen and the like. Nonclinical types of lentiviral vectors are also available and would be known to one skilled in the art.

A number of transfection techniques are generally known in the art (see, e.g., Graham et al., Virology, 52: 456-467 (1973); Sambrook et al., supra; Davis et al., Basic Methods in Molecular Biology, Elsevier (1986); and Chu et al, Gene, 13: 97 (1981).

Transfection methods include calcium phosphate co-precipitation (see, e.g., Graham et al., supra), direct micro injection into cultured cells (see, e.g., Capecchi, Cell, 22: 479-488 (1980)), electroporation (see, e.g., Shigekawa et al., BioTechniques, 6: 742-751 (1988)), liposome mediated gene transfer (see, e.g., Mannino et al., BioTechniques, 6: 682-690 (1988)), lipid mediated transduction (see, e.g., Feigner et al., Proc. Natl. Acad. Sci. USA, 84: 7413-7417 (1987)), and nucleic acid delivery using high velocity microprojectiles (see, e.g., Klein et al, Nature, 327: 70-73 (1987)).

In an embodiment, the recombinant expression vectors can be prepared using standard recombinant DNA techniques described in, for example, Sambrook et al., supra, and Ausubel et al., supra. Constructs of expression vectors, which are circular or linear, can be prepared to contain a replication system functional in a prokaryotic or eukaryotic host cell. Replication systems can be derived, e.g., from ColE1, 2 μ plasmid, λ, SV40, bovine papilloma virus, and the like.

The recombinant expression vector may comprise regulatory sequences, such as transcription and translation initiation and termination codons, which are specific to the type of host cell (e.g., bacterium, fungus, plant, or animal) into which the vector is to be introduced, as appropriate, and taking into consideration whether the vector is DNA- or RNA-based. The recombinant expression vector may comprise restriction sites to facilitate cloning.

The recombinant expression vector can include one or more marker genes, which allow for selection of transformed or transfected host cells. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes.

The recombinant expression vector can comprise a native or nonnative promoter operably linked to the nucleotide sequence encoding the CAR (including functional portions and functional variants thereof), or to the nucleotide sequence which is complementary to or which hybridizes to the nucleotide sequence encoding the CAR. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter, or a promoter found in the long-terminal repeat of the murine stem cell virus.

The recombinant expression vectors can be designed for either transient expression, for stable expression, or for both. Also, the recombinant expression vectors can be made for constitutive expression or for inducible expression.

Further, the recombinant expression vectors can be made to include a suicide gene. As used herein, the term "suicide gene" refers to a gene that causes the cell expressing the suicide gene to die. The suicide gene can be a gene that confers sensitivity to an agent, e.g., a drug, upon the cell in which the gene is expressed, and causes the cell to die when the cell is contacted with or exposed to the agent. Suicide genes are known in the art (see, for example, Suicide Gene Therapy: Methods and Reviews, Springer, Caroline J. (Cancer Research UK Centre for Cancer Therapeutics at the Institute of Cancer Research, Sutton, Surrey, UK), Humana Press, 2004) and include, for example, the Herpes Simplex Virus (HSV) thymidine kinase (TK) gene, cytosine daminase, purine nucleoside phosphorylase, and nitroreductase.

An embodiment further provides a host cell comprising any of the recombinant expression vectors described herein. As used herein, the term "host cell" refers to any type of cell that can contain the inventive recombinant expression vector. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. Suitable host cells are known in the art and include, for instance, DH5a *E. coli* cells, Chinese hamster ovarian cells, monkey VERO cells, COS cells, HEK293 cells, and the like. For purposes of amplifying or replicating the recombinant expression vector, the host cell may be a prokaryotic cell, e.g., a DH5a cell. For purposes of producing a recombinant CAR, the host cell may be a mammalian cell. The host cell may be a human cell. While the host cell can be of any cell type, can originate from any type of tissue, and can be of any developmental stage, the host cell may be a peripheral blood lymphocyte (PBL) or a peripheral blood mononuclear cell (PBMC). The host cell may be a T cell.

For purposes herein, the T cell can be any T cell, such as a cultured T cell, e.g., a primary T cell, or a T cell from a cultured T cell line, e.g., Jurkat, SupTl, etc., or a T cell obtained from a mammal. If obtained from a mammal, the T cell can be obtained from numerous sources, including but not limited to blood, bone marrow, lymph node, the thymus, or other tissues or fluids. T cells can also be enriched for or purified. The T cell may be a human T cell. The T cell may be a T cell isolated from a human. The T cell can be any type of T cell and can be of any developmental stage, including but not limited to, $CD4^+/CD8^+$ double positive T cells, $CD4^+$ helper T cells, e.g., Th1 and Th2 cells, $CD8^+$ T cells (e.g., cytotoxic T cells), tumor infiltrating cells, memory T cells, memory stem cells, i.e. Tscm, naive T cells, and the like. The T cell may be a $CD8^+$ T cell or a $CD4^+$ T cell.

In an embodiment, the CARs as described herein can be used in suitable non-T cells. Such cells are those with an immune-effector function, such as, for example, NK cells, and T-like cells generated from pluripotent stem cells.

Also provided by an embodiment is a population of cells comprising at least one host cell described herein. The population of cells can be a heterogeneous population comprising the host cell comprising any of the recombinant expression vectors described, in addition to at least one other cell, e.g., a host cell (e.g., a T cell), which does not comprise any of the recombinant expression vectors, or a cell other than a T cell, e.g., a B cell, a macrophage, a neutrophil, an erythrocyte, a hepatocyte, an endothelial cell, an epithelial cell, a muscle cell, a brain cell, etc. Alternatively, the population of cells can be a substantially homogeneous population, in which the population comprises mainly host cells (e.g., consisting essentially of) comprising the recombinant expression vector. The population also can be a clonal population of cells, in which all cells of the population are clones of a single host cell comprising a recombinant expression vector, such that all cells of the population comprise the recombinant expression vector. In one embodiment of the invention, the population of cells is a clonal population comprising host cells comprising a recombinant expression vector as described herein.

CARs (including functional portions and variants thereof), nucleic acids, recombinant expression vectors, host cells (including populations thereof), and antibodies (including antigen binding portions thereof), can be isolated and/or purified. For example, a purified (or isolated) host cell preparation is one in which the host cell is more pure than cells in their natural environment within the body. Such host cells may be produced, for example, by standard purification techniques. In some embodiments, a preparation of a host cell is purified such that the host cell represents at least about 50%, for example at least about 70%, of the total cell content of the preparation. For example, the purity can be at least about 50%, can be greater than about 60%, about 70% or about 80%, or can be about 100%.

E. Methods of Treatment

It is contemplated that the CARs disclosed herein can be used in methods of treating or preventing a disease in a mammal. In this regard, an embodiment provides a method of treating or preventing cancer in a mammal, comprising administering to the mammal the CARs, the nucleic acids, the recombinant expression vectors, the host cells, the population of cells, the antibodies and/or the antigen binding portions thereof, and/or the pharmaceutical compositions in an amount effective to treat or prevent cancer in the mammal.

An embodiment further comprises lymphodepleting the mammal prior to administering the CARs disclosed herein. Examples of lymphodepletion include, but may not be limited to, nonmyeloablative lymphodepleting chemotherapy, myeloablative lymphodepleting chemotherapy, total body irradiation, etc.

For purposes of the methods, wherein host cells or populations of cells are administered, the cells can be cells that are allogeneic or autologous to the mammal. Preferably, the cells are autologous to the mammal. As used herein, allogeneic means any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically. As used herein, "autologous" means any material derived from the same individual to whom it is later to be re-introduced into the individual.

The mammal referred to herein can be any mammal. As used herein, the term "mammal" refers to any mammal, including, but not limited to, mammals of the order Rodentia, such as mice and hamsters, and mammals of the order Lagomorpha, such as rabbits. The mammals may be from the order Carnivora, including Felines (cats) and Canines (dogs). The mammals may be from the order Artiodactyla, including Bovines (cows) and Swine (pigs) or of the order Perissodactyla, including Equines (horses). The mammals may be of the order Primates, Ceboids, or Simoids (monkeys) or of the order Anthropoids (humans and apes). Preferably, the mammal is a human.

With respect to the methods, the cancer can be any cancer, including any of acute lymphocytic cancer, acute myeloid leukemia, alveolar rhabdomyosarcoma, bladder cancer (e.g., bladder carcinoma), bone cancer, brain cancer (e.g., medulloblastoma), breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vulva, chronic lymphocytic leukemia, chronic myeloid cancer, colon cancer, esophageal cancer, cervical cancer, fibrosarcoma, gastrointestinal carcinoid tumor, head and neck cancer (e.g., head and neck squamous cell carcinoma), Hodgkin lymphoma, hypopharynx cancer, kidney cancer, larynx cancer, leukemia, liquid tumors, liver cancer, lung cancer (e.g., non-small cell lung carcinoma and lung adenocarcinoma), lymphoma, mesothelioma, mastocytoma, melanoma, multiple myeloma, nasopharynx cancer, non-Hodgkin lymphoma, B-chronic lymphocytic leukemia, hairy cell leukemia, acute lymphocytic leukemia (ALL), and Burkitt's lymphoma, ovarian cancer, pancreatic cancer, peritoneum, omentum, and mesentery cancer, pharynx cancer, prostate cancer, rectal cancer, renal cancer, skin cancer, small intestine cancer, soft tissue cancer, solid tumors, synovial sarcoma, gastric cancer, testicular cancer, thyroid cancer, and ureter cancer.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a mammal.

Furthermore, the treatment or prevention provided by the method can include treatment or prevention of one or more conditions or symptoms of the disease, e.g., cancer, being treated or prevented. Also, for purposes herein, "prevention" can encompass delaying the onset of the disease, or a symptom or condition thereof.

Another embodiment provides a method of detecting the presence of cancer in a mammal, comprising: (a) contacting a sample comprising one or more cells from the mammal with the CARs, the nucleic acids, the recombinant expression vectors, the host cells, the population of cells, the antibodies, and/or the antigen binding portions thereof, or the pharmaceutical compositions, thereby forming a complex, (b) and detecting the complex, wherein detection of the complex is indicative of the presence of cancer in the mammal.

The sample may be obtained by any suitable method, e.g., biopsy or necropsy. A biopsy is the removal of tissue and/or cells from an individual. Such removal may be to collect tissue and/or cells from the individual in order to perform experimentation on the removed tissue and/or cells. This experimentation may include experiments to determine if the individual has and/or is suffering from a certain condition or disease-state. The condition or disease may be, e.g., cancer.

With respect to an embodiment of the method of detecting the presence of a proliferative disorder, e.g., cancer, in a mammal, the sample comprising cells of the mammal can be a sample comprising whole cells, lysates thereof, or a fraction of the whole cell lysates, e.g., a nuclear or cytoplasmic fraction, a whole protein fraction, or a nucleic acid fraction. If the sample comprises whole cells, the cells can be any cells of the mammal, e.g., the cells of any organ or tissue, including blood cells or endothelial cells.

The contacting can take place in vitro or in vivo with respect to the mammal. Preferably, the contacting is in vitro.

Also, detection of the complex can occur through any number of ways known in the art. For instance, the CARs disclosed herein, polypeptides, proteins, nucleic acids, recombinant expression vectors, host cells, populations of cells, or antibodies, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles) as disclosed supra.

Methods of testing a CAR for the ability to recognize target cells and for antigen specificity are known in the art. For instance, Clay et al., J. Immunol, 163: 507-513 (1999), teaches methods of measuring the release of cytokines (e.g., interferon-γ, granulocyte/monocyte colony stimulating factor (GM-CSF), tumor necrosis factor a (TNF-a) or interleukin 2 (IL-2)). In addition, CAR function can be evaluated by measurement of cellular cytotoxicity, as described in Zhao et al, J. Immunol, 174: 4415-4423 (2005).

Another embodiment provides for the use of the CARs, nucleic acids, recombinant expression vectors, host cells, populations of cells, antibodies, or antigen binding portions thereof, and/or pharmaceutical compositions of the invention, for the treatment or prevention of a proliferative disorder, e.g., cancer, in a mammal. The cancer may be any of the cancers described herein.

Any method of administration can be used for the disclosed therapeutic agents, including local and systemic administration. For example, topical, oral, intravascular such as intravenous, intramuscular, intraperitoneal, intranasal, intradermal, intrathecal and subcutaneous administration can be used. The particular mode of administration and the dosage regimen will be selected by the attending clinician, taking into account the particulars of the case (for example the subject, the disease, the disease state involved, and whether the treatment is prophylactic). In cases in which more than one agent or composition is being administered, one or more routes of administration may be used; for example, a chemotherapeutic agent may be administered orally and an antibody or antigen binding fragment or conjugate or composition may be administered intravenously. Methods of administration include injection for which the CAR, CAR T Cell, conjugates, antibodies, antigen binding fragments, or compositions are provided in a nontoxic pharmaceutically acceptable carrier such as water, saline, Ringer's solution, dextrose solution, 5% human serum albumin, fixed oils, ethyl oleate, or liposomes. In some embodiments, local administration of the disclosed compounds can be used, for instance by applying the antibody or antigen binding fragment to a region of tissue from which a tumor has been removed, or a region suspected of being prone to tumor development. In some embodiments, sustained intra-tumoral (or near-tumoral) release of the pharmaceutical preparation that includes a therapeutically effective amount of the antibody or antigen binding fragment may be beneficial. In other examples, the conjugate is applied as an eye drop topically to the cornea, or intravitreally into the eye.

The disclosed therapeutic agents can be formulated in unit dosage form suitable for individual administration of precise dosages. In addition, the disclosed therapeutic agents may be administered in a single dose or in a multiple dose schedule. A multiple dose schedule is one in which a primary course of treatment may be with more than one separate dose, for instance 1-10 doses, followed by other doses given at subsequent time intervals as needed to maintain or reinforce the action of the compositions. Treatment can involve daily or multi-daily doses of compound(s) over a period of a few days to months, or even years. Thus, the dosage regime will also, at least in part, be determined based on the particular needs of the subject to be treated and will be dependent upon the judgment of the administering practitioner.

Typical dosages of the antibodies or conjugates can range from about 0.01 to about 30 mg/kg, such as from about 0.1 to about 10 mg/kg.

In particular examples, the subject is administered a therapeutic composition that includes one or more of the conjugates, antibodies, compositions, CARs, CAR T cells or additional agents, on a multiple daily dosing schedule, such as at least two consecutive days, 10 consecutive days, and so forth, for example for a period of weeks, months, or years. In one example, the subject is administered the conjugates, antibodies, compositions or additional agents for a period of at least 30 days, such as at least 2 months, at least 4 months, at least 6 months, at least 12 months, at least 24 months, or at least 36 months.

In some embodiments, the disclosed methods include providing surgery, radiation therapy, and/or chemotherapeutics to the subject in combination with a disclosed antibody, antigen binding fragment, conjugate, CAR or T cell expressing a CAR (for example, sequentially, substantially simultaneously, or simultaneously). Methods and therapeutic dosages of such agents and treatments are known to those skilled in the art, and can be determined by a skilled clinician. Preparation and dosing schedules for the additional agent may be used according to manufacturer's instructions or as determined empirically by the skilled practitioner. Preparation and dosing schedules for such chemotherapy are also described in Chemotherapy Service, (1992) Ed., M. C. Perry, Williams & Wilkins, Baltimore, MD.

In some embodiments, the combination therapy can include administration of a therapeutically effective amount of an additional cancer inhibitor to a subject. Non-limiting examples of additional therapeutic agents that can be used with the combination therapy include microtubule binding agents, DNA intercalators or cross-linkers, DNA synthesis inhibitors, DNA and RNA transcription inhibitors, antibodies, enzymes, enzyme inhibitors, gene regulators, and angiogenesis inhibitors. These agents (which are administered at a therapeutically effective amount) and treatments can be used alone or in combination. For example, any suitable anti-cancer or anti-angiogenic agent can be administered in combination with the CARS, CAR-T cells, antibodies, antigen binding fragment, or conjugates disclosed herein. Methods and therapeutic dosages of such agents are known to those skilled in the art, and can be determined by a skilled clinician.

Additional chemotherapeutic agents include, but are not limited to alkylating agents, such as nitrogen mustards (for example, chlorambucil, chlormethine, cyclophosphamide, ifosfamide, and melphalan), nitrosoureas (for example, carmustine, fotemustine, lomustine, and streptozocin), platinum compounds (for example, carboplatin, cisplatin, oxaliplatin, and BBR3464), busulfan, dacarbazine, mechlorethamine, procarbazine, temozolomide, thiotepa, and uramustine; antimetabolites, such as folic acid (for example, methotrexate, pemetrexed, and raltitrexed), purine (for example, cladribine, clofarabine, fludarabine, mercaptopurine, and tioguanine), pyrimidine (for example, capecitabine), cytarabine, fluorouracil, and gemcitabine; plant alkaloids, such as *podophyllum* (for example, etoposide, and teniposide), taxane (for example, docetaxel and paclitaxel), *vinca* (for example, vinblastine, vincristine, vindesine, and vinorelbine); cytotoxic/antitumor antibiotics, such as anthracycline family members (for example, daunorubicin, doxorubicin, epirubicin, idarubicin, mitoxantrone, and valrubicin), bleomycin, rifampicin, hydroxyurea, and mitomycin; topoisomerase inhibitors, such as topotecan and irinotecan; monoclonal antibodies, such as alemtuzumab, bevacizumab, cetuximab, gemtuzumab, rituximab, panitumumab, pertuzumab, and trastuzumab; photosensitizers, such as aminolevulinic acid, methyl aminolevulinate, porfimer sodium, and verteporfin; and other agents, such as alitretinoin, altretamine, amsacrine, anagrelide, arsenic trioxide, asparaginase, axitinib, bexarotene, bevacizumab, bortezomib, celecoxib, denileukin diftitox, erlotinib, estramustine, gefitinib, hydroxycarbamide, imatinib, lapatinib, pazopanib, pentostatin, masoprocol, mitotane, pegaspargase, tamoxifen, sorafenib, sunitinib, vemurafinib, vandetanib, and tretinoin. Selection and therapeutic dosages of such agents are known to those skilled in the art, and can be determined by a skilled clinician.

The combination therapy may provide synergy and prove synergistic, that is, the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation, a synergistic effect may be attained when the compounds are administered or delivered sequentially, for example by different injections in separate syringes. In general, during alternation, an effective dosage of each active ingredient is administered sequentially, i.e. serially, whereas in combination therapy, effective dosages of two or more active ingredients are administered together.

In one embodiment, an effective amount of an antibody or antigen binding fragment that specifically binds to one or more of the antigens disclosed herein or a conjugate thereof is administered to a subject having a tumor following anti-cancer treatment. After a sufficient amount of time has elapsed to allow for the administered antibody or antigen binding fragment or conjugate to form an immune complex with the antigen expressed on the respective cancer cell, the immune complex is detected. The presence (or absence) of the immune complex indicates the effectiveness of the treatment. For example, an increase in the immune complex compared to a control taken prior to the treatment indicates that the treatment is not effective, whereas a decrease in the immune complex compared to a control taken prior to the treatment indicates that the treatment is effective.

F. Biopharmaceutical Compositions

Biopharmaceutical or biologics compositions (hereinafter, "compositions") are provided herein for use in gene therapy, immunotherapy and/or cell therapy that include one or more of the disclosed CARs, or T cells expressing a CAR, antibodies, antigen binding fragments, conjugates, CARs, or T cells expressing a CAR that specifically bind to one or more antigens disclosed herein, in a carrier (such as a pharmaceutically acceptable carrier). The compositions can be prepared in unit dosage forms for administration to a subject. The amount and timing of administration are at the discretion of the treating clinician to achieve the desired outcome. The compositions can be formulated for systemic (such as intravenous) or local (such as intra-tumor) administration. In one example, a disclosed CARs, or T cells expressing a CAR, antibody, antigen binding fragment, conjugate, is formulated for parenteral administration, such as intravenous administration. Compositions including a CAR, or T cell expressing a CAR, a conjugate, antibody or antigen binding fragment as disclosed herein are of use, for example, for the treatment and detection of a tumor, for example, and not by way of limitation, a neuroblastoma. In some examples, the compositions are useful for the treatment or detection of a carcinoma. The compositions including a CAR, or T cell expressing a CAR, a conjugate, antibody or antigen binding fragment as disclosed herein are also of use, for example, for the detection of pathological angiogenesis.

The compositions for administration can include a solution of the CAR, or T cell expressing a CAR, conjugate, antibody or antigen binding fragment dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents, adjuvant agents, and the like, for example, sodium acetate, sodium chloride, potassium chloride, calcium chloride, sodium lactate and the like. The concentration of a CAR, or T cell expressing a CAR, antibody or antigen binding fragment or conjugate in these formulations can vary widely, and will be selected primarily based on fluid volumes, viscosities, body weight and the like in accordance with the particular mode of administration selected and the subject's needs. Actual methods of preparing such dosage forms for use in in gene therapy, immunotherapy and/or cell therapy are known, or will be apparent, to those skilled in the art.

A typical composition for intravenous administration includes about 0.01 to about 30 mg/kg of antibody or antigen binding fragment or conjugate per subject per day (or the corresponding dose of a CAR, or T cell expressing a CAR, conjugate including the antibody or antigen binding fragment). Actual methods for preparing administrable compositions will be known or apparent to those skilled in the art and are described in more detail in such publications as *Remington's Pharmaceutical Science, 19th ed.*, Mack Publishing Company, Easton, PA (1995).

A CAR, or T cell expressing a CAR, antibodies, antigen binding fragments, or conjugates may be provided in lyophilized form and rehydrated with sterile water before administration, although they are also provided in sterile solutions of known concentration. The CARs, or T cells expressing a CAR, antibody or antigen binding fragment or conjugate solution is then added to an infusion bag containing 0.9% sodium chloride, USP, and in some cases administered at a dosage of from 0.5 to 15 mg/kg of body weight. Considerable experience is available in the art in the administration of antibody or antigen binding fragment and conjugate drugs; for example, antibody drugs have been marketed in the U.S. since the approval of RITUXAN® in 1997. A CAR, or T cell expressing a CAR, antibodies, antigen binding fragments and conjugates thereof can be administered by slow infusion, rather than in an intravenous push or bolus. In one example, a higher loading dose is administered, with subsequent, maintenance doses being administered at a lower level. For example, an initial loading dose of 4 mg/kg antibody or antigen binding fragment (or the corresponding dose of a conjugate including the antibody or antigen binding fragment) may be infused over a period of some 90 minutes, followed by weekly maintenance doses for 4-8 weeks of 2 mg/kg infused over a 30 minute period if the previous dose was well tolerated.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, PA, (1995). Particulate systems include microspheres, microparticles, microcapsules, nanocapsules, nanospheres, and nanoparticles. Microcapsules contain the therapeutic protein, such as a cytotoxin or a drug, as a central core. In microspheres, the therapeutic is dispersed throughout the particle. Particles, microspheres, and microcapsules smaller than about 1 m are generally referred to as nanoparticles, nanospheres, and nanocapsules, respectively. Capillaries have a diameter of approximately 5 m so that only nanoparticles are administered intravenously. Microparticles are typically around 100 m in diameter and are administered subcutaneously or intramuscularly. See, for example, Kreuter, J., *Colloidal Drug Delivery Systems*, J. Kreuter, ed., Marcel Dekker, Inc., New York, NY, pp. 219-342 (1994); and Tice & Tabibi, *Treatise on Controlled Drug Delivery*, A. Kydonieus, ed., Marcel Dekker, Inc. New York, NY, pp. 315-339, (1992).

Polymers can be used for ion-controlled release of the CARs, or T cells expressing a CAR, antibody or antigen binding fragment or conjugate compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, PA (1993)). Numerous additional systems for controlled delivery of therapeutic proteins are known (see U.S. Pat. Nos. 5,055,303; 5,188,837; 4,235,871; 4,501,728; 4,837,028; 4,957,735; 5,019,369; 5,055,303; 5,514,670; 5,413,797; 5,268,164; 5,004,697; 4,902,505; 5,506,206; 5,271,961; 5,254,342 and 5,534,496).

G. Kits

In one aspect, kits employing the CARs disclosed herein are also provided. For example, kits for treating a tumor in a subject, or making a CAR T cell that expresses one or more of the CARs disclosed herein. The kits will typically include a disclosed antibody, antigen binding fragment, conjugate, nucleic acid molecule, CAR or T cell expressing a CAR as disclosed herein. More than one of the disclosed antibodies, antigen binding fragments, conjugates, nucleic acid molecules, CARs or T cells expressing a CAR can be included in the kit.

The kit can include a container and a label or package insert on or associated with the container. Suitable containers include, for example, bottles, vials, syringes, etc. The containers may be formed from a variety of materials such as glass or plastic. The container typically holds a composition including one or more of the disclosed antibodies, antigen binding fragments, conjugates, nucleic acid molecules, CARs or T cells expressing a CAR. In several embodiments the container may have a sterile access port (for example the container may be an intravenous solution bag or a vial having a stopper pierceable by a hypodermic injection needle). A label or package insert indicates that the composition is used for treating the particular condition.

The label or package insert typically will further include instructions for use of a disclosed antibodies, antigen binding fragments, conjugates, nucleic acid molecules, CARs or T cells expressing a CAR, for example, in a method of treating or preventing a tumor or of making a CAR T cell. The package insert typically includes instructions customarily included in commercial packages of therapeutic products that contain information about the indications, usage, dosage, administration, contraindications and/or warnings concerning the use of such therapeutic products. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

EXAMPLES

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Example 1

Isolation of Human CD38-Specific Antibodies from a Fully Human Yeast Display ScFv Library Materials and Methods:

A large yeast display human naive single chain variable fragment (ScFv) antibody library was used to isolate anti-human CD38 antibodies described herein. The library was constructed using a collection of human antibody gene repertoires from more than 60 individuals. Three rounds of magnetic-activated cell sorting (MACS) were performed to enrich human ScFv binders to the recombinant human CD38 extracellular domain fused with human IgG1 Fc, designated as CD38-Fc. For the first round of yeast library panning, the yeast display ScFv library ($5\times10^{10}$ cells) was incubated with 5 μg/mL CD38-Fc in 15 ml PBSA (consisting of 0.1% Bovine Serum Albumin (BSA) in Dulbecco's phosphate-buffered saline (PBS) buffer), at room temperature on a rotator for 1.5 hours. After two times washing with 25 ml PBSA, the yeast library mix was incubated with 100 μL Protein G microbeads (Miltenyi Biotec) at room temperature on a rotator for 30 minutes. After one time washing, the library mix was resuspended in 50 ml of PBSA and loaded onto the MACS cell separation column (LS column). After three times washing with 10 ml PBSA. The yeast displayed ScFv binders to the column were then eluted two times with 2 ml PBSA. These eluted yeast cells were combined and then resuspended into 50 ml SDCAA medium (20 g D-glucose, 6.7 g BD Difco™ Yeast Nitrogen Base without Amino Acids, 5 g Bacto™ Casamino Acids, 5.4 g Na2·HPO4, and 8.56 g NaH2PO4·H2O in 1 L water) and amplified with shaking at 225 rpm at 30° C. for 20 hours. The amplified pool was then induced in SGCAA medium (consisting of the same composition of SDCAA medium, but containing galactose instead of glucose), with shaking at 225 rpm at 30° C. for another 16 hours and used for next round of panning. The same process was repeated two more times to enrich the CD38-Fc specific binders.

To further enrich the binders with higher affinity and better specificity, FACS based sorting was employed to isolate the strongest binders from the pool. The induced pool was incubated with 1 μg/ml of CD38-Fc at room temperature for 1 hour and then stained with Anti-c-Myc-Alexa 488 and Goat anti-Hu-Fc PE conjugates, the top 1% of the pool with the highest PE versus FITC signal was gated and sorted. The sorted pool was amplified in SDCAA medium and yeast plasmid DNA was extracted and transformed into bacterial for single clone DNA sequencing. 40 random clones were sequenced and 36 unique sequences were identified. Fourteen (14) CD38 ScFv clones designated as M3801, M3802, M3803, M3804, M3806, M3808, M3809, M3810, M3811, M3812, M3815, M3816 and M3817, respectively, were cloned into CAR constructs for CAR-T function screening, as set forth in Example 2, Table 1. M3815_P, a variant of the M3815 CD38 ScFv clone, which differs from M3815 in the sequence of the intrachain linker connecting the heavy and the light chains of the ScFv, was also cloned into CAR constructs for CAR-T function screening, as set forth in Example 2, Table 1. Additionally, M8DR H_L and M8DR L_H, which were used as positive controls for the novel human anti CD38 ScFv-based CAR constructs, and derived from the monoclonal antibody daratumumab, were cloned into CAR constructs for CAR-T function screening as set forth in Example 2, Table 1.

Example 2

Generation of CD38-Targeting CAR T Constructs Incorporating Fully Human Binder ScFv Sequences Derived from Yeast Display Library Few treatment options exist for AML, and treatment-associated toxicities and post-treatment disease relapse are common. Moreover, immunotherapies employing non-human sequences, such as mouse-derived antibodies, may result in therapy rejection or adverse reactions in patients. In order to develop a new CAR T treatment for AML, fifteen CD38-targeting CAR T constructs incorporating fully human ScFv targeting domains were designed and evaluated for anti-tumor activity.

Materials and Methods:

(a) Cell Lines

The MM cell lines MM1.S and RPMI-8226, as well as human embryonic kidney line 293T were purchased from the American Tissue Culture Collection (ATCC, Manassas, VA). Single-cell clones of luciferase-expressing cell lines were generated by stably transducing wild-type tumor lines with lentiviral vector encoding firefly luciferase (Lentigen). Whole blood was collected from healthy volunteers at Oklahoma Blood Institute (OBI) with donors' written consent. Processed buffy coats were purchased from OBI (Oklahoma City, OK). The CD4-positive and CD8-positive human T cells were purified from buffy coats via positive selection using a 1:1 mixture of CD4⁻ and CD8⁻ MicroBeads (Miltenyi Biotec, Bergisch Gladbach, Germany) according to manufacturer's protocol.

(b) Creation of Chimeric Antigen Receptor (CAR)—Expression Vectors

CAR antigen-binding domains, ScFv, sequences were derived from human anti-CD38 ScFv. CAR T constructs were generated by linking the binder sequence in frame to CD8a linking and transmembrane domains (aa 123-191, Ref sequence ID NP_001759.3), and then to 4-1BB (CD137, aa 214-255, UniProt sequence ID Q07011) signaling domain and CD3 zeta signaling domain (CD247, aa 52-163, Ref sequence ID: NP_000725.1). CAR positive control constructs LTG2525 and LTG2526, incorporating the control ScFv with heavy and light chains derived from the monoclonal antibody daratumumab, and termed here M8DR, in orientation VH-VL, or VL-VH, respectively, were constructed in a similar manner. CAR constructs sequences were cloned into a third generation lentiviral plasmid backbone (Lentigen Technology Inc., Gaithersburg, MD). Lentiviral vector (LV) containing supernatants were generated by transient transfection of HEK 293T cells and vector pelleted by centrifugation of lentiviral vector-containing supernatants, and stored at −80° C.

(c) Primary T Cell Purification and Transduction

Human primary T cells from healthy volunteers were purified from whole blood or buffy coats (purchased from commercial provider with donor's written consent) using immunomagnetic bead selection of $CD4^+$ and $CD8^+$ cells according to manufacturer's protocol (Miltenyi Biotec, Bergisch Gladbach, Germany). T cells were cultivated in TexMACS medium supplemented with 30 IU/ml IL-2 at a density of 0.3 to 2×106 cells/ml, activated with CD3/CD28 MACS® GMP T Cell TransAct reagent (Miltenyi Biotec) and transduced on day 2 with lentiviral vectors encoding CAR constructs in the presence of 10 μg/ml protamine sulfate (Sigma-Aldrich, St. Louis, MO) overnight, and media exchanged on day 3. Cultures were propagated in TexMACS medium supplemented with 30 IU/ml IL-2 until harvest on day 8-10.

(d) Immune Effector Assays (CTL and Cytokine)

To determine cell-mediated cytotoxicity (CTL assay), 5,000 target cells stably transduced with firefly luciferase were combined with CAR T cells at various effector to target ratios and incubated overnight. SteadyGlo reagent (Promega, Madison WI) was added to each well and the resulting luminescence quantified as counts per second (sample CPS). Target only wells (max CPS) and target only wells plus 1% Tween-20 (min CPS) were used to determine assay range. Percent specific lysis was calculated as: (1-(sample CPS-min CPS)/(max CPS-min CPS)). Supernatants from co-cultures at E:T ratio of 10:1 were removed and analyzed by ELISA (eBioscience, San Diego, CA) for IFNγ and TNFα concentration.

(e) Flow Cytometric Analysis of CAR Surface Expression

For cell staining, half a million CAR T transduced cells were harvested from culture, washed two times in cold AutoMACS buffer supplemented with 0.5% bovine serum albumin (Miltenyi Biotec), and CAR surface expression detected by staining with CD38-His peptide (Thermo Fisher Scientific, Waltham, Massachusetts), followed by a secondary anti-His-PE detection reagent (Miltenyi Biotec, Bergisch Gladbach, Germany). Anti-CD4 antibody conjugated to VioBlue fluorophore (Miltenyi Biotec) was used where indicated, as per vendors' protocol. Non-transduced cells were used as negative controls. Dead cells in all studies were excluded by 7AAD staining (BD Biosciences, San Jose, CA). Cells were washed twice and resuspended in 200 ul Staining Buffer before quantitative analysis by flow cytometry. Flow cytometric analysis was performed on a MACSQuant®10 Analyzer (Miltenyi Biotec), and data plots were generated using FlowJo software (Ashland, OR).

Results:

This Example describes the creation of a CAR T cells targeting the tumor antigen CD38 for the treatment if MM and other CD38$^+$ malignancies, and the killing of CD38-expressing tumor suppressor cells in tumor microenvironment. Each CAR was comprised of a human ScFv binder derived from a human yeast display library, a CD8 hinge and transmembrane domain, a 4-1BB co-stimulatory domain and a CD3z activation domain (FIG. 1).

Table 1 below details the CAR38 constructs that were developed, designated by LTG numbers, and the corresponding designations of ScFv sequences used in each construct. Comparative control CAR sequences LTG2525, and LTG2526 incorporate ScFvs derived from the Daratumumab antibody heavy and light chains, in orientation heavy-light, and light-heavy, respectively.

TABLE 1 anti CD38 CAR T Constructs LTG numbers and the corresponding ScFv designations

| CAR construct LTG# | CD38 ScFv binder |
|---|---|
| 2089 | M3801 |
| 2090 | M3802 |
| 2091 | M3803 |
| 2092 | M3804 |
| 2093 | M3806 |
| 2094 | M3808 |
| 2095 | M3809 |
| 2096 | M3810 |
| 2097 | M3811 |
| 2098 | M3812 |
| 2099 | M3815 |
| 2501 | M3815_P |
| 2502 | M3816 |
| 2503 | M3817 |
| 2525 | M8DR H_L |
| 2526 | M8DR L_H |

Schema of CD38 CAR design is shown in FIG. 1. Fully human ScFv binders targeting CD38 were linked in frame to CD8 hinge and transmembrane domain, 4-1BB costimulatory domain and CD3 zeta activation domain. CAR sequences were incorporated into a 3rd generation lentiviral vectors and applied to primary human T cells for transduction. The surface expression of anti-CD38 CARs incorporating single chain fragment variable (ScFv) sequences, is shown in FIG. 2. The expression level for each ScFv-containing CAR was determined by flow cytometric analysis of LV-transduced T cells from healthy donors in a two-step staining procedure: step 1: CD38-His tagged peptide; followed by step 2: anti-His PE reagent. A subset of ScFv-based anti-CD38 CAR constructs were highly expressed in human primary T cells as detected CD38-His, and as compared to non-transduced T cell controls (UTD), FIG. 2. All transduced constructs expressed CAR T cells at high rate (40%-95%, expressed as % CAR T$^+$ of live T cells), with the exception of constructs LTG2097, LTG2503, which had less than 20% CAR T positive T cells. Negative controls—untransduced T cells from same donor (UTD), and anti-His PE control (FMO PE) showed no appreciable CAR T expression, indicating the specificity of CAR T staining. As shown in FIGS. 3A-C, high cytolytic activity of the anti-CD38 CARs was demonstrated for the majority of constructs analyzed. The non-transduced T cells (UTD), were used a s negative controls for CAR cytolytic function. Human primary T cells were transduced with LV encoding CAR constructs (see Methods), then incubated for 18 hours with CD38$^+$ tumor lines MM1.S, RPMI-8226, or a CD38-negative control line HEK293. Each target line was stably transduced with firefly luciferase, to facilitate the detection of the surviving tumor cell fraction in a luminescence based in vitro killing assays. Effector CAR T cells and tumor cells were combined at effector to target (E:T) ratio of 5, 10, 20 in order to compare and contrast the potency of the different CAR constructs (FIGS. 3A-C). RPMI-8226 cells were the most susceptible cell line to CD38 CAR-mediated tumor killing, with most CAR constructs achieving over 80% tumor lysis at the lowest E:T ratio of 5 (FIG. 3A). All constructs that were tested, lysed RPMI-8226 effectively, whereas the negative control UTD group caused no appreciable tumor lysis (the highest observed cytolytic activity for UTD was 10% lysis at the highest E:T ratio of 20, with lower E:T ratios yielding no detectable tumor lysis). Therefore, the lysis of RPMI-8226 by CD38-targeting T cell constructs was antigen-specific. The constructs with the lowest level of cytolytic activity vs RPMI-8226 were LTG2090, LTG2098, and LTG2099, and they achieved <70%, <40% and <10% tumor killing at E:T ratio of 1:5, respectively (FIG. 3A). Notably, the lower cytolytic function of these CAR constructs did not correlate with their surface expression levels, which were relatively high: >45%, >75%, >65%, respectively, as shown in FIG. 2. Therefore, CAR constructs' function cannot be predicted solely based on CAR surface expression, and the selection of best CAR candidates is not trivial. The second CD38$^+$ tumor line tested, MM1.S, demonstrated a similar distribution of killing potency by the anti-CD38 CAR constructs tested, and due to lower susceptibility to killing as compared to RPMI-8228, the differences in killing potency of CAR constructs were more pronounced, and allowed for a more accurate comparison of CAR potency (FIG. 3B). In the MM1.S assay, as in RPMI-8226 assay, constructs LTG2090, LTG2098, and LTG2099 were the least potent of the set, thus confirming once again that the cytolytic activity of CD38-targeting CARs is tumor antigen specific, and that CAR to CAR function assessment can be generalized across CD38-positive cell lines. In addition, moderate cytolytic activity of CAR construct LTG2502 as compared to other CAR constructs tested, was revealed in the MM1S killing assay (FIG. 3B). Similarly to RPMI-8226, the negative assay control UTD had no discernable killing activity in MM1.S tumor line, demonstrating that the killing was CAR-dependent (FIG. 3B).

The 293T tumor line, which is devoid of CD38 expression, was tested as a negative/specificity control for CAR function (FIG. 3C). The background cytolysis level in this assay was determined based on the UTD negative control, and it did not exceed 10% (FIG. 3C). None of the CD38-targeting CAR T constructs have consistently exhibited lysis of 293T cells in excess of the background level of 10%, with the exception of CAR construct LTG2501 at E:T ratio of 10:1 and 20:1 (FIG. 3C). Therefore, CAR T constructs tested in this set are target specific, whereas construct LTG2501 may be less specific, and thus may mediate of-target toxicity. The discovery of this CAR characteristic required empirical testing and could not be predicted, thus again demonstrating the non-triviality of this invention.

The capacity of anti-CD38 CAR T cells for elaborating cytokines in response to antigen-expressing target cells was then evaluated (FIGS. 4A-B). IFN gamma and TNF alpha are pro-inflammatory cytokines that are known to be secreted at high rates in conjunction with T cell activation and cytolytic activity. Tumor lines positive for CD38 expression RPMI-8226 and MM1.S, or negative for CD38 expression, 293T, were co-incubated with CAR T cells incorporating CAR38 constructs, or negative untransduced T cells (UTD), at effector to target ratio of 10:1 overnight, and culture supernatants were analyzed by ELISA for IFN gamma (FIG. 4A) and TNF alpha (FIG. 4B). The patterns of elaborated cytokines by the tested CAR constructs were similar for IFN gamma and TNF alpha. CAR constructs with the highest supernatant levels of IFN gamma and TNF alpha were LTG2091, LTG2095, LTG2097, and the positive control constructs LTG2525 and LTG2526, incorporating the control ScFv derived from the monoclonal antibody daratumumab in orientation VH-VL, or VL-VH, respectively, demonstrating that the capability of CAR constructs to secrete cytokines is consistent between the two cytokines tested (FIG. 4A, 4B). The levels of elaborated cytokines in this subset of vectors were 2500-3500 μg/ml for IFNg, and 1500-2500 μg/ml for TNF alpha (FIG. 4A, 4B) when incubated with tumor lines RPMI-H226 and MM1.S. CAR construct LTG2092 produced TNF alpha at high levels when incubated alone, as well as when incubated with the target lines RPMI-8226 and MM1.S (FIG. 4B), thus demonstrating tonic signaling. Once again, the data demonstrates the non-triviality of CAR invention, and the necessity for empiric testing to identify best CAR candidates. Without being intended to limit to any particular mechanism of action, it is believed that possible reasons for the enhanced therapeutic function associated with the exemplary CD38 targeting CARs of the invention include, for example, and not by way of limitation, a) improved lateral movement within the plasma membrane allowing for more efficient signal transduction, b) superior location within plasma membrane microdomains, such as lipid rafts, and greater ability to interact with transmembrane signaling cascades associated with T cell activation, c) superior location within the plasma membrane by preferential movement away from dampening or down-modulatory interactions, such as less proximity to or interaction with phosphatases such as CD45, and d) superior assembly into T cell receptor signaling complexes (i.e. the immune synapse), or e) superior ability to engage with tumor antigen due to two distinct targeting domains present in each CAR molecule, or any combination thereof.

Each of the applications and patents cited in this text, as well as each document or reference cited in each of the applications and patents (including during the prosecution of each issued patent; "application cited documents"), and each of the PCT and foreign applications or patents corresponding to and/or claiming priority from any of these applications and patents, and each of the documents cited or referenced in each of the application cited documents, are hereby expressly incorporated herein by reference, and may be employed in the practice of the invention. More generally, documents or references are cited in this text, either in a Reference List before the claims, or in the text itself; and, each of these documents or references ("herein cited references"), as well as each document or reference cited in each of the herein cited references (including any manufacturer's specifications, instructions, etc.), is hereby expressly incorporated herein by reference.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. An isolated nucleic acid molecule encoding a chimeric antigen receptor (CAR) comprising an amino acid sequence selected from one of the amino acids sequences of SEQ ID NO: 6, SEQ ID NO: 8, SEQ ID NO: 10, SEQ ID NO: 22, and SEQ ID NO: 24.

2. A vector comprising the nucleic acid molecule of claim 1.

3. The vector of claim 2, wherein the vector is selected from the group consisting of a DNA vector, an RNA vector, a plasmid vector, a cosmid vector, a herpes virus vector, a measles virus vector, a lentivirus vector, an adenoviral vector, a retrovirus vector, or a combination thereof.

4. The vector of claim 2, further comprising a promoter.

5. The vector of claim 4, wherein the promoter is an inducible promoter, a constitutive promoter, a tissue specific promoter, a suicide promoter or any combination thereof.

6. An isolated cell comprising the vector of claim 2.

7. The cell of claim 6, wherein the cell is a T cell.

8. The cell of claim 7, wherein the T cell is a $CD8^+$ T cell.

9. The cell of claim 6, wherein the cell is a human cell.

10. A CAR encoded by the isolated nucleic acid molecule of claim 1.

11. A method of making a cell comprising transducing a T cell with the vector of claim 2, wherein the nucleic acid sequence is operably linked to a promoter within the vector.

12. A method of generating a population of RNA-engineered cells comprising introducing an in vitro transcribed RNA or a synthetic RNA into a cell in vitro, wherein the in vitro transcribed RNA or the synthetic RNA is transcribed by the nucleic acid molecule of claim 1, and wherein the nucleic acid sequence is operably linked to a promoter.

13. A process for producing a chimeric antigen receptor-expressing cell, the process comprising introducing the isolated nucleic acid of claim 1 into an isolated cell, wherein the isolated nucleic acid is operably linked to a promoter.

14. The process for producing a chimeric antigen receptor-expressing cell according to claim 13, wherein the cell is an isolated T cell or an isolated cell population containing a T cell.

15. A pharmaceutical composition comprising an anti-tumor effective amount of a population of isolated human T cells, wherein the T cells comprise a nucleic acid sequence that encodes a CAR comprising an amino acid sequence selected from one of the amino acids sequences of SEQ ID NO: 6, SEQ ID NO: 8, SEQ ID NO: 10, SEQ ID NO: 22, and SEQ ID NO: 24, and wherein the T cells are T cells of a human having a cancer.

16. The pharmaceutical composition of claim 15, wherein the T cells are T cells of a human having a hematological cancer.

17. The pharmaceutical composition of claim 16, wherein the hematological cancer is leukemia or lymphoma.

18. The pharmaceutical composition of claim 17, wherein the leukemia is acute myeloid leukemia (AML), blastic plasmacytoid dendritic cell neoplasm (BPDCN), chronic myelogenous leukemia (CML), chronic lymphocytic leukemia (CLL), acute lymphoblastic T cell leukemia (T-ALL), or acute lymphoblastic B cell leukemia (B-ALL).

19. The pharmaceutical composition of claim 17, wherein the lymphoma is mantle cell lymphoma, non-Hodgkin's lymphoma or Hodgkin's lymphoma.

20. The pharmaceutical composition of claim 16, wherein the hematological cancer is multiple myeloma.

21. The pharmaceutical composition of claim 15, wherein the human cancer is an oral and pharynx cancer, a digestive system cancer, a respiratory system cancer, a bone and joint cancer, a soft tissue cancer, a skin cancer, a pediatric cancer, a cancer of the central nervous system a cancer of the breast, a cancer of the genital system, a cancer of the urinary system, a cancer of the eye and orbit, a cancer of the endocrine system, and a cancer of the brain, or a combination thereof.

* * * * *

SEQUENCE LISTING

```
<160> NUMBER OF SEQ ID NOS: 116

<210> SEQ ID NO 1
<211> LENGTH: 738
<212> TYPE: DNA
<213> ORGANISM: Artificial Sequence
<220> FEATURE:
<223> OTHER INFORMATION: CD38 hScFv binder M3801

<400> SEQUENCE: 1

gaagtgcaat tggtccaaag cggtgcagaa gtcaagaaac ctggttcgag cgtgaaagtg      60

tcctgcaagg cctctggcgg caccttctca tcctacgcca ttagctgggt ccgccaagcc     120

ccgggccagg gacttgagtg gatgggcgga atcatcccta tcttcgggac cgccaattac     180

gcccagaagt tccagggccg cgtgaccatc accgcggaca agtccacatc aaccgcctat     240

atggagctct cgtcgctgag atcagaggac actgctgtct actactgtgc gagggcccca     300

tacgacgatg cattcgacat ctggggacag ggtaccatgg tcactgtgtc cagcgggggc     360
```

```
ggaggctccg ggggggggcgg atcgggggc ggcggatcca acttcatgct gacccagccg    420

cactcggtgt cagagagccc cggaaagact gtgaccatta gctgcacccg gtccagcgga    480

agcatcgcct ccaactacgt gcagtggtac cagcagcggc cgggctccgc gccgaccact    540

gtgatctacg aagataacca gcgcccctcc ggtgtccctg gacggttctc cggatccatt    600

gacacctcgt ccaactccgc ctcgctgacg atctccggac tggagactga agatgaagct    660

gtgtactact gccaatccta cgactccgga tttccctacg ccgtgttcgg tggcgggacc    720

cagctcaccg tgctggga                                                  738
```

```
<210> SEQ ID NO 2
<211> LENGTH: 246
<212> TYPE: PRT
<213> ORGANISM: Artificial Sequence
<220> FEATURE:
<223> OTHER INFORMATION: CD38 hScFv binder M3801

<400> SEQUENCE: 2

Glu Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ala Pro Tyr Asp Asp Ala Phe Asp Ile Trp Gly Gln Gly Thr
            100                 105                 110

Met Val Thr Val Ser Ser Gly Gly Gly Gly Ser Gly Gly Gly Gly Ser
        115                 120                 125

Gly Gly Gly Gly Ser Asn Phe Met Leu Thr Gln Pro His Ser Val Ser
    130                 135                 140

Glu Ser Pro Gly Lys Thr Val Thr Ile Ser Cys Thr Arg Ser Ser Gly
145                 150                 155                 160

Ser Ile Ala Ser Asn Tyr Val Gln Trp Tyr Gln Gln Arg Pro Gly Ser
                165                 170                 175

Ala Pro Thr Thr Val Ile Tyr Glu Asp Asn Gln Arg Pro Ser Gly Val
            180                 185                 190

Pro Gly Arg Phe Ser Gly Ser Ile Asp Thr Ser Ser Asn Ser Ala Ser
        195                 200                 205

Leu Thr Ile Ser Gly Leu Glu Thr Glu Asp Glu Ala Val Tyr Tyr Cys
    210                 215                 220

Gln Ser Tyr Asp Ser Gly Phe Pro Tyr Ala Val Phe Gly Gly Gly Thr
225                 230                 235                 240

Gln Leu Thr Val Leu Gly
                245
```

```
<210> SEQ ID NO 3
<211> LENGTH: 735
<212> TYPE: DNA
<213> ORGANISM: Artificial Sequence
<220> FEATURE:
<223> OTHER INFORMATION: CD38 hScFv binder M3802
```

```
<400> SEQUENCE: 3

gaagtgcaac tcgtcgaatc tggtggagga tccgtgcagc ctggtggaag cctgagactg     60

tcgtgtgccg cctccgagtt caccttctcc tcgtactgga tgcactgggt cagacaggcg    120

cccggaaagg gcctggaatg ggtggccgtg atctcatacg acggcgcgaa gaagtactac    180

gccgattccg tgaagggccg ctttaccatt tcccgggaca attcaaagaa caccctctac    240

cttcaaatga actccctgag ggccgaggat actgcagtct actactgcgc tcgggatgac    300

gggagcgggg gcttcgacta ctggggacag ggaaccctcg tgactgtgtc atccggtggc    360

ggcggctccg gaggcggcgg ttccgggggg gggggatccg acatcgtgat gacgcacact    420

cctctgtcgc tgtccgtgac ccccggccag cctgcctcaa tctcgtgcaa gagctcccag    480

tcgctgctgc atagcgatgg aaagacctac ctgtattggt accttcaaaa gccgggacag    540

ccgccgcagt tgctgatcta tgaagtcagc aaccgcttct cgggagtgcc cgaccgctac    600

tccggctcgg ggagcggaac cgacttcacc ctgaaaattt cccgggtcga ggcagaggac    660

gtgggagtgt actactgcat gcaaagcatt cagttgccac tgactttcgg tggaggaacc    720

aagctcgaaa tcaaa                                                     735


<210> SEQ ID NO 4
<211> LENGTH: 245
<212> TYPE: PRT
<213> ORGANISM: Artificial Sequence
<220> FEATURE:
<223> OTHER INFORMATION: CD38 hScFv binder M3802

<400> SEQUENCE: 4

Glu Val Gln Leu Val Glu Ser Gly Gly Gly Ser Val Gln Pro Gly Gly
1               5                   10                  15

Ser Leu Arg Leu Ser Cys Ala Ala Ser Glu Phe Thr Phe Ser Ser Tyr
            20                  25                  30

Trp Met His Trp Val Arg Gln Ala Pro Gly Lys Gly Leu Glu Trp Val
        35                  40                  45

Ala Val Ile Ser Tyr Asp Gly Ala Lys Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Asp Gly Ser Gly Gly Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Ile Val Met Thr His Thr Pro Leu Ser Leu
    130                 135                 140

Ser Val Thr Pro Gly Gln Pro Ala Ser Ile Ser Cys Lys Ser Ser Gln
145                 150                 155                 160

Ser Leu Leu His Ser Asp Gly Lys Thr Tyr Leu Tyr Trp Tyr Leu Gln
                165                 170                 175

Lys Pro Gly Gln Pro Pro Gln Leu Leu Ile Tyr Glu Val Ser Asn Arg
            180                 185                 190

Phe Ser Gly Val Pro Asp Arg Tyr Ser Gly Ser Gly Ser Gly Thr Asp
        195                 200                 205

Phe Thr Leu Lys Ile Ser Arg Val Glu Ala Glu Asp Val Gly Val Tyr
```

```
    210                 215                 220

Tyr Cys Met Gln Ser Ile Gln Leu Pro Leu Thr Phe Gly Gly Gly Thr
225                 230                 235                 240

Lys Leu Glu Ile Lys
                245


<210> SEQ ID NO 5
<211> LENGTH: 750
<212> TYPE: DNA
<213> ORGANISM: Artificial Sequence
<220> FEATURE:
<223> OTHER INFORMATION: CD38 hScFv binder M3803

<400> SEQUENCE: 5

gaagtgcaat tggtgcagag cggtggagga cttgtgaaac ctggtggatc cctgagactt      60

tcctgtgccg cttcgggctt caccttctcg gactactaca tgtcctggat tcgccaggcc     120

cctggaaagg gactggaatg ggtgtcatac atcagctcct ccggttccac catctactat     180

gccgattccg tgaagggcag attcaccatc tcgcgcgaca acgccaagaa cactctctat     240

ctgcaaatga actcactgcg ggctgaggac accgcggtct actactgcgc ccgggacctc     300

agcggaaagt ccagcggatg gtcccattac ttcgattact ggggacaggg aaccctggtc     360

accgtgtcca gcggcggggg gggctcgggt ggcggcggct ccggcggcgg cgggagcaac     420

ttcatgctga ctcagcccca ctccgtgtcc gagagcccgg gaaagaccgt gactatttcg     480

tgcacacggt cctccgggag cattgcgaac aactacgtgc agtggtacca gcagcggccc     540

gatagggccc caaccactgt gatctacgaa gatgaccagc ggccgtctgg agtcccggac     600

cgcttctcgg ggtccatcga ctcatcatcc aattccgcat cgctgacgat cagcggactg     660

aagatcgagg acgaagccga ttactactgc cagtcctacg acggcaccaa ctgggtcttt     720

gggggtggaa ccaagctgac tgtgctcgga                                      750


<210> SEQ ID NO 6
<211> LENGTH: 250
<212> TYPE: PRT
<213> ORGANISM: Artificial Sequence
<220> FEATURE:
<223> OTHER INFORMATION: CD38 hScFv binder M3803

<400> SEQUENCE: 6

Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Ser Gly Lys Ser Ser Gly Trp Ser His Tyr Phe Asp
            100                 105                 110

Tyr Trp Gly Gln Gly Thr Leu Val Thr Val Ser Ser Gly Gly Gly Gly
        115                 120                 125

Ser Gly Gly Gly Gly Ser Gly Gly Gly Gly Ser Asn Phe Met Leu Thr
```

```
    130                 135                 140

Gln Pro His Ser Val Ser Glu Ser Pro Gly Lys Thr Val Thr Ile Ser
145                 150                 155                 160

Cys Thr Arg Ser Ser Gly Ser Ile Ala Asn Asn Tyr Val Gln Trp Tyr
                165                 170                 175

Gln Gln Arg Pro Asp Arg Ala Pro Thr Thr Val Ile Tyr Glu Asp Asp
            180                 185                 190

Gln Arg Pro Ser Gly Val Pro Asp Arg Phe Ser Gly Ser Ile Asp Ser
        195                 200                 205

Ser Ser Asn Ser Ala Ser Leu Thr Ile Ser Gly Leu Lys Ile Glu Asp
    210                 215                 220

Glu Ala Asp Tyr Tyr Cys Gln Ser Tyr Asp Gly Thr Asn Trp Val Phe
225                 230                 235                 240

Gly Gly Gly Thr Lys Leu Thr Val Leu Gly
                245                 250


<210> SEQ ID NO 7
<211> LENGTH: 729
<212> TYPE: DNA
<213> ORGANISM: Artificial Sequence
<220> FEATURE:
<223> OTHER INFORMATION: CD38 hScFv binder M3804

<400> SEQUENCE: 7

gaagtgcaac ttgtcgaaag cggtggaggt cttgtccaac ctggtcgctc cctgaggctc      60

tcgtgtgccg cgagcggatt caccttctca tcgtacgcta tgtcctgggt cagacaggct     120

cctggaaagg gcctggaatg ggtggccgtg atctcctacg acggcagcaa caagtattac     180

gccgactcag tgaagggccg gttcaccatt tcccgggaca acagcaagaa caccctgtac     240

ttgcaaatga actccctgcg ggccgaggat accgcggtgt actactgcgc ccacctccgc     300

tttggatacg gaatggatgt ctggggacag ggaactaccg tgaccgtgtc gtccgggggg     360

gggggaagcg gcggcggggg atcgggtggc ggcggatccc agactgtggt cacccaagag     420

ccttcactga ccgtgtcccc gggtggcacc gtgacgctga cttgcgcgtc atctaccggg     480

gccgtgacct cggaccacta cccctgctgg ttccagcaga aacccggaca tccaccgaga     540

gccctggtgt actccactga caccatccac tcctggactc cggcccggtt ctccggaagc     600

ctcctgggcg ggaaggccgc actgacagtg tccggagtgc agcccgagga tgaagccgac     660

tactactgtc tgctctacta tgggggagca cgcgtgttcg gtggcggcac tcagctgacc     720

gtgctggga                                                             729


<210> SEQ ID NO 8
<211> LENGTH: 243
<212> TYPE: PRT
<213> ORGANISM: Artificial Sequence
<220> FEATURE:
<223> OTHER INFORMATION: CD38 hScFv binder M3804

<400> SEQUENCE: 8

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala His Leu Arg Phe Gly Tyr Gly Met Asp Val Trp Gly Gln Gly Thr
            100                 105                 110

Thr Val Thr Val Ser Ser Gly Gly Gly Gly Ser Gly Gly Gly Gly Ser
        115                 120                 125

Gly Gly Gly Gly Ser Gln Thr Val Val Thr Gln Glu Pro Ser Leu Thr
    130                 135                 140

Val Ser Pro Gly Gly Thr Val Thr Leu Thr Cys Ala Ser Ser Thr Gly
145                 150                 155                 160

Ala Val Thr Ser Asp His Tyr Pro Cys Trp Phe Gln Gln Lys Pro Gly
                165                 170                 175

His Pro Pro Arg Ala Leu Val Tyr Ser Thr Asp Thr Ile His Ser Trp
            180                 185                 190

Thr Pro Ala Arg Phe Ser Gly Ser Leu Leu Gly Gly Lys Ala Ala Leu
        195                 200                 205

Thr Val Ser Gly Val Gln Pro Glu Asp Glu Ala Asp Tyr Tyr Cys Leu
    210                 215                 220

Leu Tyr Tyr Gly Gly Ala Arg Val Phe Gly Gly Gly Thr Gln Leu Thr
225                 230                 235                 240

Val Leu Gly
```

<210> SEQ ID NO 9
<211> LENGTH: 735
<212> TYPE: DNA
<213> ORGANISM: Artificial Sequence
<220> FEATURE:
<223> OTHER INFORMATION: CD38 hScFv binder M3806

<400> SEQUENCE: 9

```
caagtgcaac tcgtccaatc cggagctgaa gtcaagaagc caggatcttc cgtgaaagtg     60

tcgtgcaagg cctccggggg aacattctcc tcatatgcga tcagctgggt ccgccaggct    120

ccgggacagg gcttggagtg gatgggtatc attaaccctt cgggcggctc aactagctac    180

gcccagaagt tccagggcag agtgaccatg accagggaca ccagcacttc gacggtgtac    240

atggaactgt cctcactgcg gtccgaggac accgccgtgt actactgcgc ccgggagtat    300

tcctcctccc gcgtggacgc cttcgatatc tggggacagg gtaccatggt cactgtgtcg    360

tccggcggcg gcggaagcgg gggtggcggg agcggtggcg gcggatccag ctacgaactc    420

acccagccgc cgtcagtgtc cgtgagcccg ggacagaccg caaccattac ttgttccggg    480

gatgacctgg gatccaaata cgtgtgctgg taccaacaga agcctggtca ctcgcccgtg    540

ctgatcatct acgacgactc agaccggccc agcggcatcc ccgagagatt ttccggatcc    600

aacagcggaa acaccgccac tctgactatt tcgcgcgtcg aggccggcga cgaagcggat    660

tactactgcc aagtctggga cagctcctcg gatcatgccg tgttcggggg cggaacccag    720

cttaccgtgc tgggg                                                     735
```

<210> SEQ ID NO 10
<211> LENGTH: 245
<212> TYPE: PRT
<213> ORGANISM: Artificial Sequence
<220> FEATURE:

<223> OTHER INFORMATION: CD38 hScFv binder M3806

<400> SEQUENCE: 10

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Tyr Ser Ser Ser Arg Val Asp Ala Phe Asp Ile Trp Gly
            100                 105                 110

Gln Gly Thr Met Val Thr Val Ser Ser Gly Gly Gly Gly Ser Gly Gly
        115                 120                 125

Gly Gly Ser Gly Gly Gly Gly Ser Ser Tyr Glu Leu Thr Gln Pro Pro
    130                 135                 140

Ser Val Ser Val Ser Pro Gly Gln Thr Ala Thr Ile Thr Cys Ser Gly
145                 150                 155                 160

Asp Asp Leu Gly Ser Lys Tyr Val Cys Trp Tyr Gln Gln Lys Pro Gly
                165                 170                 175

His Ser Pro Val Leu Ile Ile Tyr Asp Asp Ser Asp Arg Pro Ser Gly
            180                 185                 190

Ile Pro Glu Arg Phe Ser Gly Ser Asn Ser Gly Asn Thr Ala Thr Leu
        195                 200                 205

Thr Ile Ser Arg Val Glu Ala Gly Asp Glu Ala Asp Tyr Tyr Cys Gln
    210                 215                 220

Val Trp Asp Ser Ser Ser Asp His Ala Val Phe Gly Gly Gly Thr Gln
225                 230                 235                 240

Leu Thr Val Leu Gly
                245
```

<210> SEQ ID NO 11
<211> LENGTH: 717
<212> TYPE: DNA
<213> ORGANISM: Artificial Sequence
<220> FEATURE:
<223> OTHER INFORMATION: CD38 hScFv binder M3808

<400> SEQUENCE: 11

```
gaagtgcagt tggtggagag cggtggagga cttgtgcaac ctggtggatc cctgagattg     60

tcgtgtgccg cctccggttt caccttctcc tcgtactgga tgagctgggt ccgccaggca    120

cccgggaagg gactggaatg ggtggcggac attaaggatg acggctccga gcggtactac    180

gtggactccg tgaagggccg gttcactatc tcaagagaca atgccaagaa cagcctgtac    240

ctccaaatga actcgctgcg ggccgaggat accgcagtgt attactgcgc ccgcgacgtg    300

tgggctggga tggatgtctg gggccagggg accactgtca ctgtgtctag cgggggcggc    360

ggaagcggcg gcggcggatc cggtggtggc ggaagcgaca ttcagctgac ccagtcccca    420

tcattcctgt ccgcctccgt gggcgacagg gtcactatca cttgccaagc cagccaggac    480

atctccaact acctgaactg gtaccagcag aagcctggaa aagctccgaa gctcctcatc    540
```

```
tacgacgcct cgaacctcga aaccggagtg ccctcacggt tttccggatc gggatcgggg    600

accgatttct ccttcaccat ttcatccctg caacccgagg acatcgcgac ctactactgc    660

caacagacat actccccgcc gattacgttc ggacagggaa cccgcctgga aatcaag       717


<210> SEQ ID NO 12
<211> LENGTH: 239
<212> TYPE: PRT
<213> ORGANISM: Artificial Sequence
<220> FEATURE:
<223> OTHER INFORMATION: CD38 hScFv binder M3808

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Trp Met Ser Trp Val Arg Gln Ala Pro Gly Lys Gly Leu Glu Trp Val
        35                  40                  45

Ala Asp Ile Lys Asp Asp Gly Ser Glu Arg Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Val Trp Ala Gly Met Asp Val Trp Gly Gln Gly Thr Thr
            100                 105                 110

Val Thr Val Ser Ser Gly Gly Gly Gly Ser Gly Gly Gly Gly Ser Gly
        115                 120                 125

Gly Gly Gly Ser Asp Ile Gln Leu Thr Gln Ser Pro Ser Phe Leu Ser
    130                 135                 140

Ala Ser Val Gly Asp Arg Val Thr Ile Thr Cys Gln Ala Ser Gln Asp
145                 150                 155                 160

Ile Ser Asn Tyr Leu Asn Trp Tyr Gln Gln Lys Pro Gly Lys Ala Pro
                165                 170                 175

Lys Leu Leu Ile Tyr Asp Ala Ser Asn Leu Glu Thr Gly Val Pro Ser
            180                 185                 190

Arg Phe Ser Gly Ser Gly Ser Gly Thr Asp Phe Ser Phe Thr Ile Ser
        195                 200                 205

Ser Leu Gln Pro Glu Asp Ile Ala Thr Tyr Tyr Cys Gln Gln Thr Tyr
    210                 215                 220

Ser Pro Pro Ile Thr Phe Gly Gln Gly Thr Arg Leu Glu Ile Lys
225                 230                 235


<210> SEQ ID NO 13
<211> LENGTH: 66
<212> TYPE: DNA
<213> ORGANISM: Artificial Sequence
<220> FEATURE:
<223> OTHER INFORMATION: leader/signal peptide

<400> SEQUENCE: 13

atgctgctgc tggtgaccag cctgctgctg tgcgaactgc cgcatccggc gtttctgctg     60

attccg                                                                66


<210> SEQ ID NO 14
<211> LENGTH: 22
```

```
<212> TYPE: PRT
<213> ORGANISM: Artificial Sequence
<220> FEATURE:
<223> OTHER INFORMATION: leader/signal peptide

<400> SEQUENCE: 14

Met Leu Leu Leu Val Thr Ser Leu Leu Leu Cys Glu Leu Pro His Pro
1               5                   10                  15

Ala Phe Leu Leu Ile Pro
            20


<210> SEQ ID NO 15
<211> LENGTH: 723
<212> TYPE: DNA
<213> ORGANISM: Artificial Sequence
<220> FEATURE:
<223> OTHER INFORMATION: CD38 hScFv binder M3809

<400> SEQUENCE: 15

caagtccaac tcgtccagtc cggtgccgaa gtcaagaagc ctggctcatc cgtgaaagtg      60

tcctgcaaag catcgggcgg aaccttctcc tcctatgcca tttcctgggt ccgccaggca     120

ccgggccagg gtctggagtg gatgggcggg attatcccta tcttcggaac tgccaaccac     180

gcccaaaagt tccagggacg cgtgaccatt accgccgatg aatcaacctc aaccgcctac     240

atggaactgt ccagcttgag gtccgaggac accgccgtgt actactgcgc gttcatgatg     300

gtgccggagt actactttga ctactggggc cagggaaccc ttgtgaccgt gtcgtccggt     360

ggtggcggat ccgggggggg gggatctggg ggcggcggaa gcgatatcca gatgacccag     420

tcgccatcga gcctgtccgc ttccgtgggc gacagagtga cgatcacttg ccgggcttca     480

caaggcatca gaaatgacct gggctggtat cagcagaagc ccggagaagc gcccaagcgg     540

ctgatctacg cggccagcac cctgcaaaac ggagtgcctt cgcggttctc cgggagcggc     600

tccggaactg acttcactct gactattaac agcctccagc ccgaggattt cgccacatac     660

tactgtcagc agtacaacag ctacccgtac accttcggac agggaactaa gctcgaaatc     720

aag                                                                   723


<210> SEQ ID NO 16
<211> LENGTH: 241
<212> TYPE: PRT
<213> ORGANISM: Artificial Sequence
<220> FEATURE:
<223> OTHER INFORMATION: CD38 hScFv binder M3809

<400> SEQUENCE: 16

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn His Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Phe Met Met Val Pro Glu Tyr Tyr Phe Asp Tyr Trp Gly Gln Gly
            100                 105                 110
```

```
Thr Leu Val Thr Val Ser Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Arg Ala Ser
145                 150                 155                 160

Gln Gly Ile Arg Asn Asp Leu Gly Trp Tyr Gln Gln Lys Pro Gly Glu
                165                 170                 175

Ala Pro Lys Arg Leu Ile Tyr Ala Ala Ser Thr Leu Gln Asn Gly Val
            180                 185                 190

Pro Ser Arg Phe Ser Gly Ser Gly Ser Gly Thr Asp Phe Thr Leu Thr
        195                 200                 205

Ile Asn Ser Leu Gln Pro Glu Asp Phe Ala Thr Tyr Tyr Cys Gln Gln
    210                 215                 220

Tyr Asn Ser Tyr Pro Tyr Thr Phe Gly Gln Gly Thr Lys Leu Glu Ile
225                 230                 235                 240

Lys
```

<210> SEQ ID NO 17
<211> LENGTH: 732
<212> TYPE: DNA
<213> ORGANISM: Artificial Sequence
<220> FEATURE:
<223> OTHER INFORMATION: CD38 hScFv binder M3810

<400> SEQUENCE: 17

```
aaagtgcaac tccaagaaag cggccccgga cttgtcaaac cgtcccagac tctctccctg      60

acctgtgccg tcagcggtgg ctcaatttcg agcggtggct actactggtc ctggatcagg     120

cagcatccgg gaaagggctt ggagtggatt ggatacatct actactccgg gtccacctac     180

tacaatccct cgctgaagtc gagagtcacc atcagcgtgg acacctccaa gaaccagttt     240

agcctgaagc tgtcctcagt gaccgcagct gacaccgccg tgtactactg cgcccgcggc     300

ggagtgatgg gcggagactt cgactactgg ggacagggaa ccctggtcac tgtgtccagc     360

gggggggggg gatccggcgg cggcggttcc ggtggcggag ggtcccagtc agtgctgact     420

cagccacctt ccgtgtctgt gtcgcccgga caaaccgcca gcatcacgtg ctccggcgac     480

aacctcggtg atcactatgt gtgctggtac caacagcggc cggggcagtc accggtgctg     540

attatgtacg aggatactaa gcgcccttcc ggaatccctg accggttctc gggaagcaac     600

tccggaaaca ccgccaccct gaccatctcc ggaacccaga caatggatga agcggactac     660

tattgcgtgg cgtgggacga ttcgctgtcc ggctgggtgt tcggcggggg aactcagctg     720

actgtgctcg ga                                                         732
```

<210> SEQ ID NO 18
<211> LENGTH: 244
<212> TYPE: PRT
<213> ORGANISM: Artificial Sequence
<220> FEATURE:
<223> OTHER INFORMATION: CD38 hScFv binder M3810

<400> SEQUENCE: 18

```
Lys Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Ser Gly
            20                  25                  30
```

```
Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Gly Gly Val Met Gly Gly Asp Phe Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gln Ser Val Leu Thr Gln Pro Pro Ser
    130                 135                 140

Val Ser Val Ser Pro Gly Gln Thr Ala Ser Ile Thr Cys Ser Gly Asp
145                 150                 155                 160

Asn Leu Gly Asp His Tyr Val Cys Trp Tyr Gln Gln Arg Pro Gly Gln
                165                 170                 175

Ser Pro Val Leu Ile Met Tyr Glu Asp Thr Lys Arg Pro Ser Gly Ile
            180                 185                 190

Pro Asp Arg Phe Ser Gly Ser Asn Ser Gly Asn Thr Ala Thr Leu Thr
        195                 200                 205

Ile Ser Gly Thr Gln Thr Met Asp Glu Ala Asp Tyr Tyr Cys Val Ala
    210                 215                 220

Trp Asp Asp Ser Leu Ser Gly Trp Val Phe Gly Gly Gly Thr Gln Leu
225                 230                 235                 240

Thr Val Leu Gly
```

<210> SEQ ID NO 19
<211> LENGTH: 756
<212> TYPE: DNA
<213> ORGANISM: Artificial Sequence
<220> FEATURE:
<223> OTHER INFORMATION: CD38 hScFv binder M3811

<400> SEQUENCE: 19

```
caactccaac tccaagaatc tggaccaggc ctcgtgaagc cctcccaaac tctgtccctg     60

acctgtaccg tgtcgggtgg aagcatttcg agcggtggat actactggtc ctggatcagg    120

cagcatcctg gaaagggact ggagtggatt gggtacatct actactccgg ctcaacctac    180

tacaacccgt ccttgaaatc gcgcgtgacg atctccgtgg acacttcaaa gaaccagttc    240

agcctgaagc tttcctccgt gaccgcggcc gatacagcgg tgtactactg cgctcgggat    300

cagagcgtgg ccgaccctgg tggcggctac tactactacg gaatggatgt ctggggacag    360

ggaaccaccg tgactgtgtc cagcgggggc ggcggatccg gggggggggg atcgggcggc    420

ggcggttcgc agtccgtgct gacccagcca cctagcgtgt cagtggcacc gggacagacc    480

gcctccattt cctgcggggg aaatgacttc ggtagccgct ccgtgtcatg gtatcaccag    540

aagccgggac aggccccggt gctggtcatc tatgacgaca acgacagacc ctcgggcatc    600

cccgaacggt tttcgggaag cacctccgga gacactgcca ccctgaccat ctcccgggtc    660

gaggtcggcg atgaagccga ttactactgc caagtctggg acgacgactc cgaccactgg    720

gtgttcggcg gcggaactaa gctgactgtg ctgggg                              756
```

<210> SEQ ID NO 20

```
<211> LENGTH: 252
<212> TYPE: PRT
<213> ORGANISM: Artificial Sequence
<220> FEATURE:
<223> OTHER INFORMATION: CD38 hScFv binder M3811

<400> SEQUENCE: 20

Gln Leu Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Asp Gln Ser Val Ala Asp Pro Gly Gly Gly Tyr Tyr Tyr
            100                 105                 110

Tyr Gly Met Asp Val Trp Gly Gln Gly Thr Thr Val Thr Val Ser Ser
        115                 120                 125

Gly Gly Gly Gly Ser Gly Gly Gly Gly Ser Gly Gly Gly Gly Ser Gln
    130                 135                 140

Ser Val Leu Thr Gln Pro Pro Ser Val Ser Val Ala Pro Gly Gln Thr
145                 150                 155                 160

Ala Ser Ile Ser Cys Gly Gly Asn Asp Phe Gly Ser Arg Ser Val Ser
                165                 170                 175

Trp Tyr His Gln Lys Pro Gly Gln Ala Pro Val Leu Val Ile Tyr Asp
            180                 185                 190

Asp Asn Asp Arg Pro Ser Gly Ile Pro Glu Arg Phe Ser Gly Ser Thr
        195                 200                 205

Ser Gly Asp Thr Ala Thr Leu Thr Ile Ser Arg Val Glu Val Gly Asp
    210                 215                 220

Glu Ala Asp Tyr Tyr Cys Gln Val Trp Asp Asp Asp Ser Asp His Trp
225                 230                 235                 240

Val Phe Gly Gly Gly Thr Lys Leu Thr Val Leu Gly
                245                 250


<210> SEQ ID NO 21
<211> LENGTH: 747
<212> TYPE: DNA
<213> ORGANISM: Artificial Sequence
<220> FEATURE:
<223> OTHER INFORMATION: CD38 hScFv binder M3812

<400> SEQUENCE: 21

caagtgcaac tccaacaatc gggccccgga ctcgtgaaac cgtcccagac tctgtccctt      60

acttgcgtga tttccgggga ctccgtgagc tcaaactcgg cggcctggaa ctggattaga     120

cagtcccctt cccggggtct ggaatggctg ggccggactt actaccggtc gaagtggcac     180

aacgattacg cagtcagcgt cgagagccgc atcatcgtga acccggacac ctcaaagaac     240

cagttcagcc tgcaactgaa ttccgtgacc cccgaggaca ccgctgtgta ctactgcgcc     300

cgcgaccccg gatacttcta tggactggac gtctggggac aggggaccat ggtcaccgtg     360

tcgagcggcg gcggcggatc cggtggcggg ggatccggcg gtggcggatc caacttcatg     420
```

```
ttgactcagc cgcattcggt gtcggagtcc cctggaaaga cagtcaccat cccatgtacc    480

cggagcagcg gaactatcgc cgactactac gtgcagtggt accagcagcg ccctgattcc    540

tcaccgatca ttgtgatcta tgacgacaac cagaggccct ccggggtgcc ggatagattc    600

agcggatcca ttgactcctc gtccaactct gcctcactga cgatctccgg gctcaagacc    660

gaagatgaag cggcctacta ctgccagtca tacgactcca ccaaccactg ggtgtttggt    720

ggcggaacta agctgaccgt gctggga                                        747
```

<210> SEQ ID NO 22
<211> LENGTH: 249
<212> TYPE: PRT
<213> ORGANISM: Artificial Sequence
<220> FEATURE:
<223> OTHER INFORMATION: CD38 hScFv binder M3812

<400> SEQUENCE: 22

```
Gln Val Gln Leu Gln Gln Ser Gly Pro Gly Leu Val Lys Pro Ser Gln
1               5                   10                  15

Thr Leu Ser Leu Thr Cys Val Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp His Asn Asp Tyr Ala
    50                  55                  60

Val Ser Val Glu Ser Arg Ile Ile Val Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Asp Pro Gly Tyr Phe Tyr Gly Leu Asp Val Trp
            100                 105                 110

Gly Gln Gly Thr Met Val Thr Val Ser Ser Gly Gly Gly Gly Ser Gly
        115                 120                 125

Gly Gly Gly Ser Gly Gly Gly Gly Ser Asn Phe Met Leu Thr Gln Pro
    130                 135                 140

His Ser Val Ser Glu Ser Pro Gly Lys Thr Val Thr Ile Pro Cys Thr
145                 150                 155                 160

Arg Ser Ser Gly Thr Ile Ala Asp Tyr Tyr Val Gln Trp Tyr Gln Gln
                165                 170                 175

Arg Pro Asp Ser Ser Pro Ile Ile Val Ile Tyr Asp Asp Asn Gln Arg
            180                 185                 190

Pro Ser Gly Val Pro Asp Arg Phe Ser Gly Ser Ile Asp Ser Ser Ser
        195                 200                 205

Asn Ser Ala Ser Leu Thr Ile Ser Gly Leu Lys Thr Glu Asp Glu Ala
    210                 215                 220

Ala Tyr Tyr Cys Gln Ser Tyr Asp Ser Thr Asn His Trp Val Phe Gly
225                 230                 235                 240

Gly Gly Thr Lys Leu Thr Val Leu Gly
                245
```

<210> SEQ ID NO 23
<211> LENGTH: 723
<212> TYPE: DNA
<213> ORGANISM: Artificial Sequence
<220> FEATURE:
<223> OTHER INFORMATION: CD38 hScFv binder M3815

<400> SEQUENCE: 23

```
caagtcacac tcaaagaatc cggaccggtg ctcgtgaagc ctactgaaac cttgaccctg      60
acatgcacct tttccgggtt ctccctgagc acctcgggag tcggagtggc gtggattagg     120
cagccgccag gaaaagacct cgagtggctc gcccttatct actgggacga tgacaagcgc     180
tactcaccct cactggagag cagactgacg atcaccaagg atacctcgaa gaaccaagtg     240
gccctgacta tgtccgacat ggaccctgtg gacaccgcga cttactactg cgcccggggc     300
gattactggg gacggctgga ctactgggga cagggaactc tggtcaccgt gtccagcggc     360
ggcggtggtt caggggggtgg cggcagcggg gggggcggat cggatatcca gcttacccag     420
tcgccgtcct ccctctctgc atcgattggc gaccgcgtga ctattacgtg tcaggcctcc     480
gaggacatca acaactacct gaactggtac cagcagaagc ccggaaaggc ccccaaagctg     540
ctgatctacg acgctagcaa cttggaaacc ggagtgccgt cccggttctc cggatccggg     600
agcggtaccg acttcacctt caccatcaac tccctgcaac ccgaggatat tgccacctat     660
tactgccaac agttcgacaa tatgcctctg actttcgggg gcggcactaa gctcgaaatc     720
aag                                                                   723
```

<210> SEQ ID NO 24
<211> LENGTH: 241
<212> TYPE: PRT
<213> ORGANISM: Artificial Sequence
<220> FEATURE:
<223> OTHER INFORMATION: CD38 hScFv binder M3815

<400> SEQUENCE: 24

```
Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Val Gly Val Ala Trp Ile Arg Gln Pro Pro Gly Lys Asp Leu Glu
        35                  40                  45

Trp Leu Ala Leu Ile Tyr Trp Asp Asp Asp Lys Arg Tyr Ser Pro Ser
    50                  55                  60

Leu Glu Ser Arg Leu Thr Ile Thr Lys Asp Thr Ser Lys Asn Gln Val
65                  70                  75                  80

Ala Leu Thr Met Ser Asp Met Asp Pro Val Asp Thr Ala Thr Tyr Tyr
                85                  90                  95

Cys Ala Arg Gly Asp Tyr Trp Gly Arg Leu Asp Tyr Trp Gly Gln Gly
            100                 105                 110

Thr Leu Val Thr Val Ser Ser Gly Gly Gly Gly Ser Gly Gly Gly Gly
        115                 120                 125

Ser Gly Gly Gly Gly Ser Asp Ile Gln Leu Thr Gln Ser Pro Ser Ser
    130                 135                 140

Leu Ser Ala Ser Ile Gly Asp Arg Val Thr Ile Thr Cys Gln Ala Ser
145                 150                 155                 160

Glu Asp Ile Asn Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Asn Ser Leu Gln Pro Glu Asp Ile Ala Thr Tyr Tyr Cys Gln Gln
    210                 215                 220
```

```
Phe Asp Asn Met Pro Leu Thr Phe Gly Gly Gly Thr Lys Leu Glu Ile
225                 230                 235                 240

Lys


<210> SEQ ID NO 25
<211> LENGTH: 723
<212> TYPE: DNA
<213> ORGANISM: Artificial Sequence
<220> FEATURE:
<223> OTHER INFORMATION: CD38 hScFv binder M3815_P

<400> SEQUENCE: 25

caagtcactc tgaaagaatc cggtcccgtg ctcgtcaaac ccaccgaaac cctgaccctg      60

acctgtactt tctccggatt ttccctctca acctccggcg tgggcgtggc ctggattcgg     120

cagcctcccg gaaaggattt ggagtggctg gccctgatct actgggatga cgataagcgc     180

tactccccat ccctcgagtc ccggctgact atcactaagg acacctccaa gaatcaagtc     240

gcccttacta tgtcggacat ggaccctgtg gacaccgcta cgtactactg cgctcgggga     300

gactattggg ggcgcctgga ctactgggga cagggaaccc tcgtgaccgt gtcgtctggg     360

ggcggcggac cgggtggcgg agcgtccggg ggcggtggat cggacatcca gctgacacag     420

agccccagca gcctgagcgc ctcgattggc gacagagtga ccattacgtg ccaggcatcc     480

gaggacatca acaactacct gaactggtac cagcagaagc ctgggaaggc ccccaaagctg    540

ctgatctacg acgcctccaa cctggaaacc ggagtgccgt caaggttcag cggctcggga     600

tcaggaaccg atttcacttt caccatcaac agcttgcagc cggaagatat cgcgacctac     660

tactgccaac agttcgacaa catgccgctg actttcggtg gcgggaccaa gcttgagatt     720

aag                                                                   723


<210> SEQ ID NO 26
<211> LENGTH: 241
<212> TYPE: PRT
<213> ORGANISM: Artificial Sequence
<220> FEATURE:
<223> OTHER INFORMATION: CD38 hScFv binder M3815_P

<400> SEQUENCE: 26

Gln Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Gly Val Gly Val Ala Trp Ile Arg Gln Pro Pro Gly Lys Asp Leu Glu
        35                  40                  45

Trp Leu Ala Leu Ile Tyr Trp Asp Asp Asp Lys Arg Tyr Ser Pro Ser
    50                  55                  60

Leu Glu Ser Arg Leu Thr Ile Thr Lys Asp Thr Ser Lys Asn Gln Val
65                  70                  75                  80

Ala Leu Thr Met Ser Asp Met Asp Pro Val Asp Thr Ala Thr Tyr Tyr
                85                  90                  95

Cys Ala Arg Gly Asp Tyr Trp Gly Arg Leu Asp Tyr Trp Gly Gln Gly
            100                 105                 110

Thr Leu Val Thr Val Ser Ser Gly Gly Gly Gly Pro Gly Gly Gly Ala
        115                 120                 125

Ser Gly Gly Gly Gly Ser Asp Ile Gln Leu Thr Gln Ser Pro Ser Ser
    130                 135                 140
```

```
Leu Ser Ala Ser Ile Gly Asp Arg Val Thr Ile Thr Cys Gln Ala Ser
145                 150                 155                 160

Glu Asp Ile Asn Asn Tyr Leu Asn Trp Tyr Gln Gln Lys Pro Gly Lys
                165                 170                 175

Ala Pro Lys Leu Leu Ile Tyr Asp Ala Ser Asn Leu Glu Thr Gly Val
            180                 185                 190

Pro Ser Arg Phe Ser Gly Ser Gly Ser Gly Thr Asp Phe Thr Phe Thr
        195                 200                 205

Ile Asn Ser Leu Gln Pro Glu Asp Ile Ala Thr Tyr Tyr Cys Gln Gln
    210                 215                 220

Phe Asp Asn Met Pro Leu Thr Phe Gly Gly Gly Thr Lys Leu Glu Ile
225                 230                 235                 240

Lys


<210> SEQ ID NO 27
<211> LENGTH: 72
<212> TYPE: DNA
<213> ORGANISM: Artificial Sequence
<220> FEATURE:
<223> OTHER INFORMATION: CD8 transmembrane domain

<400> SEQUENCE: 27

atctacatct gggcgccctt ggccgggact tgtggggtcc ttctcctgtc actggttatc     60

accctttact gc                                                         72


<210> SEQ ID NO 28
<211> LENGTH: 22
<212> TYPE: PRT
<213> ORGANISM: Artificial Sequence
<220> FEATURE:
<223> OTHER INFORMATION: CD8 transmembrane domain

<400> SEQUENCE: 28

Ile Trp Ala Pro Leu Ala Gly Thr Cys Gly Val Leu Leu Leu Ser Leu
1               5                   10                  15

Val Ile Thr Leu Tyr Cys
            20


<210> SEQ ID NO 29
<211> LENGTH: 135
<212> TYPE: DNA
<213> ORGANISM: Artificial Sequence
<220> FEATURE:
<223> OTHER INFORMATION: CD8 hinge domain

<400> SEQUENCE: 29

accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgat                                                     135


<210> SEQ ID NO 30
<211> LENGTH: 47
<212> TYPE: PRT
<213> ORGANISM: Artificial Sequence
<220> FEATURE:
<223> OTHER INFORMATION: CD8 hinge domain

<400> SEQUENCE: 30

Thr Thr Thr Pro Ala Pro Arg Pro Pro Thr Pro Ala Pro Thr Ile Ala
1               5                   10                  15
```

```
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr
        35                  40                  45


<210> SEQ ID NO 31
<211> LENGTH: 42
<212> TYPE: PRT
<213> ORGANISM: Artificial Sequence
<220> FEATURE:
<223> OTHER INFORMATION: hinge region of CD8.alpha

<400> SEQUENCE: 31

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 32
<211> LENGTH: 106
<212> TYPE: PRT
<213> ORGANISM: Artificial Sequence
<220> FEATURE:
<223> OTHER INFORMATION: Human IgG CL

<400> SEQUENCE: 32

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105


<210> SEQ ID NO 33
<211> LENGTH: 126
<212> TYPE: DNA
<213> ORGANISM: Artificial Sequence
<220> FEATURE:
<223> OTHER INFORMATION: signaling domain

<400> SEQUENCE: 33

aaacggggca gaaagaaact cctgtatata ttcaaacaac catttatgag accagtacaa      60

actactcaag aggaagatgg ctgtagctgc cgatttccag aagaagaaga aggaggatgt     120

gaactg                                                                126


<210> SEQ ID NO 34
<211> LENGTH: 42
<212> TYPE: PRT
<213> ORGANISM: Artificial Sequence
<220> FEATURE:
<223> OTHER INFORMATION: signaling domain
```

<400> SEQUENCE: 34

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 35
<211> LENGTH: 336
<212> TYPE: DNA
<213> ORGANISM: Artificial Sequence
<220> FEATURE:
<223> OTHER INFORMATION: signaling domain

<400> SEQUENCE: 35

```
agagtgaagt tcagcaggag cgcagacgcc cccgcgtaca agcagggcca gaaccagctc     60

tataacgagc tcaatctagg acgaagagag gagtacgatg ttttggacaa gagacgtggc    120

cgggaccctg agatgggggg aaagccgaga aggaagaacc ctcaggaagg cctgtacaat    180

gaactgcaga aagataagat ggcggaggcc tacagtgaga ttgggatgaa aggcgagcgc    240

cggaggggca aggggcacga tggcctttac cagggtctca gtacagccac caaggacacc    300

tacgacgccc ttcacatgca ggccctgccc cctcgc                              336
```

<210> SEQ ID NO 36
<211> LENGTH: 112
<212> TYPE: PRT
<213> ORGANISM: Artificial Sequence
<220> FEATURE:
<223> OTHER INFORMATION: CD3zeta

<400> SEQUENCE: 36

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 37
<211> LENGTH: 726
<212> TYPE: DNA
<213> ORGANISM: Artificial Sequence
<220> FEATURE:
<223> OTHER INFORMATION: ScFv CD 19

<400> SEQUENCE: 37

```
gacatccaga tgacacagac tacatcctcc ctgtctgcct ctctgggaga cagagtcacc     60

atcagttgca gggcaagtca ggacattagt aaatatttaa attggtatca gcagaaacca    120
```

-continued

```
gatggaactg ttaaactcct gatctaccat acatcaagat tacactcagg agtcccatca    180

aggttcagtg gcagtgggtc tggaacagat tattctctca ccattagcaa cctggagcaa    240

gaagatattg ccacttactt ttgccaacag ggtaatacgc ttccgtacac gttcggaggg    300

gggaccaagc tggagatcac aggtggcggt ggctcgggcg gtggtgggtc gggtggcggc    360

ggatctgagg tgaaactgca ggagtcagga cctggcctgg tggcgccctc acagagcctg    420

tccgtcacat gcactgtctc aggggtctca ttacccgact atggtgtaag ctggattcgc    480

cagcctccac gaaagggtct ggagtggctg ggagtaatat ggggtagtga aaccacatac    540

tataattcag ctctcaaatc cagactgacc atcatcaagg acaactccaa gagccaagtt    600

ttcttaaaaa tgaacagtct gcaaactgat gacacagcca tttactactg tgccaaacat    660

tattactacg gtggtagcta tgctatggac tactggggcc aaggaacctc agtcaccgtc    720

tcctca                                                               726
```

```
<210> SEQ ID NO 38
<211> LENGTH: 242
<212> TYPE: PRT
<213> ORGANISM: Artificial Sequence
<220> FEATURE:
<223> OTHER INFORMATION: ScFv CD 19

<400> SEQUENCE: 38

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Ser Lys Tyr
            20                  25                  30

Leu Asn Trp Tyr Gln Gln Lys Pro Asp Gly Thr Val Lys Leu Leu Ile
        35                  40                  45

Tyr His Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Tyr
                85                  90                  95

Thr Phe Gly Gly Gly Thr Lys Leu Glu Ile Thr Gly Gly Gly Gly Ser
            100                 105                 110

Gly Gly Gly Gly Ser Gly Gly Gly Gly Ser Glu Val Lys Leu Gln Glu
        115                 120                 125

Ser Gly Pro Gly Leu Val Ala Pro Ser Gln Ser Leu Ser Val Thr Cys
    130                 135                 140

Thr Val Ser Gly Val Ser Leu Pro Asp Tyr Gly Val Ser Trp Ile Arg
145                 150                 155                 160

Gln Pro Pro Arg Lys Gly Leu Glu Trp Leu Gly Val Ile Trp Gly Ser
                165                 170                 175

Glu Thr Thr Tyr Tyr Asn Ser Ala Leu Lys Ser Arg Leu Thr Ile Ile
            180                 185                 190

Lys Asp Asn Ser Lys Ser Gln Val Phe Leu Lys Met Asn Ser Leu Gln
        195                 200                 205

Thr Asp Asp Thr Ala Ile Tyr Tyr Cys Ala Lys His Tyr Tyr Tyr Gly
    210                 215                 220

Gly Ser Tyr Ala Met Asp Tyr Trp Gly Gln Gly Thr Ser Val Thr Val
225                 230                 235                 240

Ser Ser
```

<210> SEQ ID NO 39
<211> LENGTH: 66
<212> TYPE: DNA
<213> ORGANISM: Artificial Sequence
<220> FEATURE:
<223> OTHER INFORMATION: leader peptide

<400> SEQUENCE: 39
atgctgctgc tggtgaccag cctgctgctg tgcgaactgc cgcatccggc gtttctgctg 60
attccg 66

<210> SEQ ID NO 40
<211> LENGTH: 22
<212> TYPE: PRT
<213> ORGANISM: Artificial Sequence
<220> FEATURE:
<223> OTHER INFORMATION: leader peptide

<400> SEQUENCE: 40

Met Leu Leu Leu Val Thr Ser Leu Leu Leu Cys Glu Leu Pro His Pro
1 5 10 15

Ala Phe Leu Leu Ile Pro
20

<210> SEQ ID NO 41
<211> LENGTH: 85
<212> TYPE: DNA
<213> ORGANISM: Artificial Sequence
<220> FEATURE:
<223> OTHER INFORMATION: leader peptide

<400> SEQUENCE: 41
ggctctgaaa gtgctgttgg aacaagaaaa gaccttcttc accttgctcg tgttgctggg 60
gtacctgtcc tgcaaagtca cctgt 85

<210> SEQ ID NO 42
<211> LENGTH: 29
<212> TYPE: PRT
<213> ORGANISM: Artificial Sequence
<220> FEATURE:
<223> OTHER INFORMATION: leader peptide

<400> SEQUENCE: 42

Met Ala Leu Lys Val Leu Leu Glu Gln Glu Lys Thr Phe Phe Thr Leu
1 5 10 15

Leu Val Leu Leu Gly Tyr Leu Ser Cys Lys Val Thr Cys
20 25

<210> SEQ ID NO 43
<211> LENGTH: 63
<212> TYPE: DNA
<213> ORGANISM: Artificial Sequence
<220> FEATURE:
<223> OTHER INFORMATION: leader peptide

<400> SEQUENCE: 43
atggcgctgc cggtgaccgc gctgctgctg ccgctggcgc tgctgctgca tgcggcgcgc 60
ccg 63

<210> SEQ ID NO 44
<211> LENGTH: 21
<212> TYPE: PRT
<213> ORGANISM: Artificial Sequence
<220> FEATURE:
<223> OTHER INFORMATION: leader peptide

<400> SEQUENCE: 44

Met Ala Leu Pro Val Thr Ala Leu Leu Leu Pro Leu Ala Leu Leu Leu
1 5 10 15

His Ala Ala Arg Pro
20

<210> SEQ ID NO 45
<211> LENGTH: 123
<212> TYPE: DNA
<213> ORGANISM: Artificial Sequence
<220> FEATURE:
<223> OTHER INFORMATION: CD28 co-stimulatory domain

<400> SEQUENCE: 45
cggtcgaaga ggtccagact cttgcactcc gactacatga acatgactcc tagaaggccc 60
ggacccacta gaaagcacta ccagccgtac gcccctcctc gggatttcgc cgcataccgg 120
tcc 123

<210> SEQ ID NO 46
<211> LENGTH: 41
<212> TYPE: PRT
<213> ORGANISM: Artificial Sequence
<220> FEATURE:
<223> OTHER INFORMATION: CD28 co-stimulatory domain

<400> SEQUENCE: 46

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 47
<211> LENGTH: 336
<212> TYPE: DNA
<213> ORGANISM: Artificial Sequence
<220> FEATURE:
<223> OTHER INFORMATION: CD3 zeta activation domain

<400> SEQUENCE: 47
agagtgaagt tcagccgctc agccgatgca ccggcctacc agcagggaca gaaccagctc 60
tacaacgagc tcaacctggg tcggcgggaa gaatatgacg tgctggacaa acggcgcggc 120
agagatccgg agatgggggg aaagccgagg aggaagaacc ctcaagaggg cctgtacaac 180
gaactgcaga aggacaagat ggcggaagcc tactccgaga tcggcatgaa gggagaacgc 240
cggagaggga agggtcatga cggactgtac cagggcctgt caactgccac taaggacact 300
tacgatgcgc tccatatgca agctttgccc ccgcgg 336

<210> SEQ ID NO 48
<211> LENGTH: 112
<212> TYPE: PRT
<213> ORGANISM: Artificial Sequence
<220> FEATURE:
<223> OTHER INFORMATION: CD3 zeta activation domain

<400> SEQUENCE: 48

Arg Val Lys Phe Ser Arg Ser Ala Asp Ala Pro Ala Tyr Gln Gln Gly

```
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110


<210> SEQ ID NO 49
<211> LENGTH: 201
<212> TYPE: DNA
<213> ORGANISM: Artificial Sequence
<220> FEATURE:
<223> OTHER INFORMATION: hinge and transmembrane domain

<400> SEQUENCE: 49

gcggccgcgg tcggattcca agacatggaa tgcgtgccct gcggcgaccc gccacctcct     60

tacgagccgc actgcgcatc gaaggtcaac ctcgtgaaga tcgcgagcac cgcgtcctca    120

ccccgggata ctgctctggc cgccgtgatt tgttccgcct tggccaccgt gcttctggcc    180

ctgctgatcc tctgtgtgat c                                              201


<210> SEQ ID NO 50
<211> LENGTH: 67
<212> TYPE: PRT
<213> ORGANISM: Artificial Sequence
<220> FEATURE:
<223> OTHER INFORMATION: hinge and transmembrane domain

<400> SEQUENCE: 50

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu Ala Ala
        35                  40                  45

Val Ile Cys Ser Ala Leu Ala Thr Val Leu Leu Ala Leu Leu Ile Leu
    50                  55                  60

Cys Val Ile
65


<210> SEQ ID NO 51
<211> LENGTH: 63
<212> TYPE: DNA
<213> ORGANISM: Artificial Sequence
<220> FEATURE:
<223> OTHER INFORMATION: transmembrane domain

<400> SEQUENCE: 51

gccgccgtga tttgttccgc cttggccacc gtgcttctgg ccctgctgat cctctgtgtg     60

atc                                                                   63


<210> SEQ ID NO 52
```

<211> LENGTH: 21
<212> TYPE: PRT
<213> ORGANISM: Artificial Sequence
<220> FEATURE:
<223> OTHER INFORMATION: transmembrane domain

<400> SEQUENCE: 52

Ala Ala Val Ile Cys Ser Ala Leu Ala Thr Val Leu Leu Ala Leu Leu
1               5                   10                  15

Ile Leu Cys Val Ile
            20

<210> SEQ ID NO 53
<211> LENGTH: 138
<212> TYPE: DNA
<213> ORGANISM: Artificial Sequence
<220> FEATURE:
<223> OTHER INFORMATION: hinge domain

<400> SEQUENCE: 53
gcggccgcgg tcggattcca agacatggaa tgcgtgccct gcggcgaccc gccacctcct     60
tacgagccgc actgcgcatc gaaggtcaac ctcgtgaaga tcgcgagcac cgcgtcctca    120
ccccgggata ctgctctg                                                  138

<210> SEQ ID NO 54
<211> LENGTH: 46
<212> TYPE: PRT
<213> ORGANISM: Artificial Sequence
<220> FEATURE:
<223> OTHER INFORMATION: hinge domain

<400> SEQUENCE: 54

Ala Ala Ala Val Gly Phe Gln Asp Met Glu Cys Val Pro Cys Gly Asp
1               5                   10                  15

Pro Pro Pro Pro Tyr Glu Pro His Cys Ala Ser Lys Val Asn Leu Val
            20                  25                  30

Lys Ile Ala Ser Thr Ala Ser Ser Pro Arg Asp Thr Ala Leu
        35                  40                  45

<210> SEQ ID NO 55
<211> LENGTH: 80
<212> TYPE: DNA
<213> ORGANISM: Artificial Sequence
<220> FEATURE:
<223> OTHER INFORMATION: hinge domain

<400> SEQUENCE: 55
tacgagcctc actgcgccag caaagtcaac ttggtgaaga tcgcgagcac tgcctcgtcc     60
cctcgggaca ctgctctggc                                                 80

<210> SEQ ID NO 56
<211> LENGTH: 26
<212> TYPE: PRT
<213> ORGANISM: Artificial Sequence
<220> FEATURE:
<223> OTHER INFORMATION: hinge domain

<400> SEQUENCE: 56

Tyr Glu Pro His Cys Ala Ser Lys Val Asn Leu Val Lys Ile Ala Ser
1               5                   10                  15

Thr Ala Ser Ser Pro Arg Asp Thr Ala Leu
            20                  25

<210> SEQ ID NO 57
<211> LENGTH: 222
<212> TYPE: DNA
<213> ORGANISM: Artificial Sequence
<220> FEATURE:
<223> OTHER INFORMATION: hinge domain fused to transmembrane domain

<400> SEQUENCE: 57
gcggccgcgc ccgcccctcg gcccccgact cctgccccga cgatcgcttc ccaacctctc 60
tcgctgcgcc cggaagcatg ccggcccgcc gccggtggcg ctgtccacac tcgcggactg 120
gactttgata ccgcactggc ggccgtgatc tgtagcgccc tggccaccgt gctgctggcg 180
ctgctcatcc tttgcgtgat ctactgcaag cggcagccta gg 222

<210> SEQ ID NO 58
<211> LENGTH: 74
<212> TYPE: PRT
<213> ORGANISM: Artificial Sequence
<220> FEATURE:
<223> OTHER INFORMATION: hinge domain fused to transmembrane domain

<400> SEQUENCE: 58

Ala Ala Ala Pro Ala Pro Arg Pro Pro Thr Pro Ala Pro Thr Ile Ala
1 5 10 15

Ser Gln Pro Leu Ser Leu Arg Pro Glu Ala Cys Arg Pro Ala Ala Gly
20 25 30

Gly Ala Val His Thr Arg Gly Leu Asp Phe Asp Thr Ala Leu Ala Ala
35 40 45

Val Ile Cys Ser Ala Leu Ala Thr Val Leu Leu Ala Leu Leu Ile Leu
50 55 60

Cys Val Ile Tyr Cys Lys Arg Gln Pro Arg
65 70

<210> SEQ ID NO 59
<211> LENGTH: 123
<212> TYPE: DNA
<213> ORGANISM: Artificial Sequence
<220> FEATURE:
<223> OTHER INFORMATION: co-stimulatory domain

<400> SEQUENCE: 59
cggtcgaaga ggtccagact cttgcactcc gactacatga acatgactcc tagaaggccc 60
ggacccacta gaaagcacta ccagccgtac gcccctcctc gggatttcgc cgcataccgg 120
tcc 123

<210> SEQ ID NO 60
<211> LENGTH: 41
<212> TYPE: PRT
<213> ORGANISM: Artificial Sequence
<220> FEATURE:
<223> OTHER INFORMATION: CD28 co-stimulatory domain

<400> SEQUENCE: 60

Arg Ser Lys Arg Ser Arg Leu Leu His Ser Asp Tyr Met Asn Met Thr
1 5 10 15

Pro Arg Arg Pro Gly Pro Thr Arg Lys His Tyr Gln Pro Tyr Ala Pro
20 25 30

Pro Arg Asp Phe Ala Ala Tyr Arg Ser
35 40

<210> SEQ ID NO 61
<211> LENGTH: 336
<212> TYPE: DNA
<213> ORGANISM: Artificial Sequence
<220> FEATURE:
<223> OTHER INFORMATION: CD3 zeta version 2

<400> SEQUENCE: 61

```
cgcgtgaaat ttagccgcag cgcggatgcg ccggcgtatc agcagggcca gaaccagctg     60

tataacgaac tgaacctggg ccgccgcgaa gaatatgatg tgctggataa acgccgcggc    120

cgcgatccgg aaatgggcgg caaaccgcgc cgcaaaaacc cgcaggaagg cctgtataac    180

gaactgcaga aagataaaat ggcggaagcg tatagcgaaa ttggcatgaa aggcgaacgc    240

cgccgcggca aaggccatga tggcctgtat cagggcctga gcaccgcgac caaagatacc    300

tatgatgcgc tgcatatgca ggcgctgccg ccgcgc                              336
```

<210> SEQ ID NO 62
<211> LENGTH: 112
<212> TYPE: PRT
<213> ORGANISM: Artificial Sequence
<220> FEATURE:
<223> OTHER INFORMATION: CD3 zeta version 2

<400> SEQUENCE: 62

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 63
<211> LENGTH: 93
<212> TYPE: DNA
<213> ORGANISM: Artificial Sequence
<220> FEATURE:
<223> OTHER INFORMATION: Furin P2A Furin

<400> SEQUENCE: 63

```
cgcgcgaaac gcagcggcag cggcgcgacc aactttagcc tgctgaaaca ggcgggcgat     60

gtggaagaaa acccgggccc gcgagcaaag agg                                  93
```

<210> SEQ ID NO 64
<211> LENGTH: 31
<212> TYPE: PRT
<213> ORGANISM: Artificial Sequence
<220> FEATURE:
<223> OTHER INFORMATION: Furin P2A Furin

<400> SEQUENCE: 64

```
Arg Ala Lys Arg Ser Gly Ser Gly Ala Thr Asn Phe Ser Leu Leu Lys
1               5                   10                  15
```

```
Gln Ala Gly Asp Val Glu Glu Asn Pro Gly Pro Arg Ala Lys Arg
            20                  25                  30


<210> SEQ ID NO 65
<211> LENGTH: 78
<212> TYPE: DNA
<213> ORGANISM: Artificial Sequence
<220> FEATURE:
<223> OTHER INFORMATION: Furin T2A

<400> SEQUENCE: 65

agagctaaac gctctgggtc tggtgaagga cgaggtagcc ttcttacgtg cggagacgtg     60

gaggaaaacc caggaccc                                                   78


<210> SEQ ID NO 66
<211> LENGTH: 26
<212> TYPE: PRT
<213> ORGANISM: Artificial Sequence
<220> FEATURE:
<223> OTHER INFORMATION: Furin T2A

<400> SEQUENCE: 66

Arg Ala Lys Arg Ser Gly Ser Gly Glu Gly Arg Gly Ser Leu Leu Thr
1               5                   10                  15

Cys Gly Asp Val Glu Glu Asn Pro Gly Pro
            20                  25


<210> SEQ ID NO 67
<211> LENGTH: 1005
<212> TYPE: DNA
<213> ORGANISM: Artificial Sequence
<220> FEATURE:
<223> OTHER INFORMATION: truncated EGFR (tEGFR) tag

<400> SEQUENCE: 67

aggaaggttt gcaatggaat cggtataggg gagtttaagg attcacttag cataaacgct     60

actaatatta aacacttcaa aaactgtacg agtataagtg gagatcttca cattttgccg    120

gttgcattcc gaggcgattc attcacccac acgccaccgc ttgacccaca agaattggat    180

attcttaaaa ccgttaaaga aataacgggg tttttgctca ttcaagcgtg gccagaaaat    240

cgcactgacc tccatgcttt cgagaacctg gagattataa gaggacgaac taagcagcat    300

ggtcaattct cccttgctgt ggtcagcctg aacatcacca gtcttggttt gcggtccctc    360

aaggaaattt cagatggaga tgtcatcata agcggcaaca agaatttgtg ctatgcaaat    420

accataaact ggaaaaaact gtttggcact tccggccaga aaaccaagat tatttcaaat    480

cggggtgaga acagctgcaa agccaccggc caggtttgtc atgccttgtg ctctccggaa    540

ggctgttggg ggccagaacc cagggactgc gtcagttgca gaaacgtctc aagaggccgc    600

gaatgcgttg acaagtgtaa cctccttgag ggtgagccac gagagtttgt tgagaacagc    660

gagtgtatac aatgtcaccc tgaatgtttg ccccaggcta tgaatataac ctgcacaggc    720

cgcgggcctg ataactgcat ccagtgtgct cattacatag atggacctca ctgtgtgaaa    780

acctgcccgg ccggagttat gggagaaaac aacactctgg tgtggaaata cgctgatgca    840

ggccacgtgt gccacctttg tcacccgaat tgtacatatg ggtgtaccgg tcctggactt    900

gaaggttgcc ctaccaatgg ccctaaaata cccagtatcg caactggcat ggtaggcgct    960

cttctcttgc tcttggtagt tgctctcggc ataggtcttt ttatg                   1005


<210> SEQ ID NO 68
```

```
<211> LENGTH: 335
<212> TYPE: PRT
<213> ORGANISM: Artificial Sequence
<220> FEATURE:
<223> OTHER INFORMATION: truncated EGFR (tEGFR) tag

<400> SEQUENCE: 68

Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300

Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 69
<211> LENGTH: 735
<212> TYPE: DNA
<213> ORGANISM: Artificial Sequence
<220> FEATURE:
<223> OTHER INFORMATION: CD38 hScFv binder M3816
```

<400> SEQUENCE: 69

```
caagtgcaac tccaagaatc cggtcctggc ctcgtcaaac cttccgaaac actgtccctg     60

acctgtaccg tgtccggagg gtcgattagc tcgtcgtcat actactgggg atggatcaga    120

cagccgccgg gaaagggact cgagtggatc gggtccatct actactcggg tagcacttac    180

tacaacccgt cgctgaagtc ccgcgtgact atttccgtgg acacctccaa gaaccagttc    240

agcctgaagc tgagctccgt gaccgctgcc gataccgcag tgtactactg cgcgcgccgg    300

ggaagcatcc gcgcctttga catctgggga cagggaacta tggtcacggt gtccagcggc    360

ggtggcggat ctggcggcgg cggatccggg gggggggaa gccagtcagt gctgactcag    420

ccgccttcgg tgtccgaggc gcccggccag agggtcacca tttcctgctc tggatcgtcc    480

agcaacattg gcaacaacgc cgtcaactgg taccagcagc tgcccgggga agcccccaag    540

ctgttgatct actacgacga gtatctgcca agcggagtgt cagacagatt ctccgcgtcg    600

aagtccggca cctccgcctc acttgcaatc tccggcctgc ggtccgagga cgaagccgat    660

tactattgcg ccgcctggga cgataatctg tccggttggg tgttcggcgg tggaacccag    720

cttaccgtgc tcgga                                                      735
```

<210> SEQ ID NO 70
<211> LENGTH: 245
<212> TYPE: PRT
<213> ORGANISM: Artificial Sequence
<220> FEATURE:
<223> OTHER INFORMATION: CD38 hScFv binder M3816

<400> SEQUENCE: 70

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Arg Gly Ser Ile Arg Ala Phe Asp Ile Trp Gly Gln Gly
            100                 105                 110

Thr Met Val Thr Val Ser Ser Gly Gly Gly Gly Ser Gly Gly Gly Gly
        115                 120                 125

Ser Gly Gly Gly Gly Ser Gln Ser Val Leu Thr Gln Pro Pro Ser Val
    130                 135                 140

Ser Glu Ala Pro Gly Gln Arg Val Thr Ile Ser Cys Ser Gly Ser Ser
145                 150                 155                 160

Ser Asn Ile Gly Asn Asn Ala Val Asn Trp Tyr Gln Gln Leu Pro Gly
                165                 170                 175

Glu Ala Pro Lys Leu Leu Ile Tyr Tyr Asp Glu Tyr Leu Pro Ser Gly
            180                 185                 190

Val Ser Asp Arg Phe Ser Ala Ser Lys Ser Gly Thr Ser Ala Ser Leu
        195                 200                 205

Ala Ile Ser Gly Leu Arg Ser Glu Asp Glu Ala Asp Tyr Tyr Cys Ala
    210                 215                 220
```

```
Ala Trp Asp Asp Asn Leu Ser Gly Trp Val Phe Gly Gly Gly Thr Gln
225                 230                 235                 240

Leu Thr Val Leu Gly
                245


<210> SEQ ID NO 71
<211> LENGTH: 735
<212> TYPE: DNA
<213> ORGANISM: Artificial Sequence
<220> FEATURE:
<223> OTHER INFORMATION: CD38 hScFv binder M3817

<400> SEQUENCE: 71

caagtgcaac tccaagaatc cggtcctggt ctggtcaaac cctccgaaac tctgtccctg      60

acgtgcaccg tgtcgggata ctccatttcc tccggatact actggggttg gatccgccag     120

cctccgggaa aaggcctgga atgggtcgga accatcggga aggacggatc cactttctat     180

tccccgtcgc tgaagtcacg gatcaccatt agccaggaca cctccaagaa ccagttcagc     240

ctgaagctga actccgtgaa cgccgcggac actgccgtct actactgtgc gaagcacaag     300

tggtccttcg actccgggaa cgattacttc gaccactggg gccaggggac cctcgtgacc     360

gtgtcgtccg gcggcggggg atccggtggc gggggaagcg gcggcggcgg atcagacatt     420

cagctgaccc agtctccctc atccctgtcg gctagcgtgg gcgatagagt gaccatcaca     480

tgccaggcat cgcaggacat ttcgaactat ctgaactggt accagcagaa gcctggaaag     540

gccccgaagc ttttgatcta cgacgccagc aacctggaga ctggagtgcc cagccggttc     600

agcggatcgg gatccggtac cgatttcacc tttaccatct cctcactgca accagaggat     660

atcgccacct actactgcca gcagtaccag aatctcccgc tcactttcgg acaagggact     720

aggcttgaga tcaag                                                      735


<210> SEQ ID NO 72
<211> LENGTH: 245
<212> TYPE: PRT
<213> ORGANISM: Artificial Sequence
<220> FEATURE:
<223> OTHER INFORMATION: CD38 hScFv binder M3817

<400> SEQUENCE: 72

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Val Gly Thr Ile Gly Lys Asp Gly Ser Thr Phe Tyr Ser Pro Ser Leu
    50                  55                  60

Lys Ser Arg Ile Thr Ile Ser Gln Asp Thr Ser Lys Asn Gln Phe Ser
65                  70                  75                  80

Leu Lys Leu Asn Ser Val Asn Ala Ala Asp Thr Ala Val Tyr Tyr Cys
                85                  90                  95

Ala Lys His Lys Trp Ser Phe Asp Ser Gly Asn Asp Tyr Phe Asp His
            100                 105                 110

Trp Gly Gln Gly Thr Leu Val Thr Val Ser Ser Gly Gly Gly Gly Ser
        115                 120                 125

Gly Gly Gly Gly Ser Gly Gly Gly Gly Ser Asp Ile Gln Leu Thr Gln
    130                 135                 140
```

```
Ser Pro Ser Ser Leu Ser Ala Ser Val Gly Asp Arg Val Thr Ile Thr
145                 150                 155                 160

Cys Gln Ala Ser Gln Asp Ile Ser Asn Tyr Leu Asn Trp Tyr Gln Gln
                165                 170                 175

Lys Pro Gly Lys Ala Pro Lys Leu Leu Ile Tyr Asp Ala Ser Asn Leu
            180                 185                 190

Glu Thr Gly Val Pro Ser Arg Phe Ser Gly Ser Gly Ser Gly Thr Asp
        195                 200                 205

Phe Thr Phe Thr Ile Ser Ser Leu Gln Pro Glu Asp Ile Ala Thr Tyr
    210                 215                 220

Tyr Cys Gln Gln Tyr Gln Asn Leu Pro Leu Thr Phe Gly Gln Gly Thr
225                 230                 235                 240

Arg Leu Glu Ile Lys
                245


<210> SEQ ID NO 73
<211> LENGTH: 738
<212> TYPE: DNA
<213> ORGANISM: Artificial Sequence
<220> FEATURE:
<223> OTHER INFORMATION: CD38 hScFv binder  M8DR H_L

<400> SEQUENCE: 73

gaggtacagt tgctggagag tggaggtggt ctggtacagc cgggagggtc cttgcggctg     60

tcatgcgcag ttagcggatt tactttcaac tccttcgcca tgtcctgggt taggcaggcc    120

cctggaaagg gtctcgaatg ggtctctgcc atcagtggga gtggaggtgg cacttactat    180

gctgacagcg tcaaagggcg cttcactatt agtcgagaca actcaaagaa tactctgtac    240

cttcaaatga actccctccg agccgaagac actgccgtat acttttgtgc taaagacaaa    300

atcctctggt tcggcgagcc tgtgttcgac tactggggac agggtacgct cgtgaccgtg    360

tcatctgcta gcggtggtgg cggctcaggt ggtggtggct ctggtggagg tggtagtgag    420

atagtactga cacagagccc ggcaactctt tctctctcac ctggtgaaag agcaaccctc    480

agttgcaggg cttcccagtc cgtatcttct tatctcgcct ggtaccaaca gaaaccgggg    540

caagcaccac gactcttgat ctatgatgcc tctaaccgcg caacagggat tccggcccga    600

tttagcggca gcggtagcgg cacggacttt acactgacga tttcttccct tgagccggaa    660

gactttgctg tgtattattg tcaacaacgg tctaattggc cgccgacgtt tggacagggc    720

acaaaggttg aaataaag                                                  738


<210> SEQ ID NO 74
<211> LENGTH: 246
<212> TYPE: PRT
<213> ORGANISM: Artificial Sequence
<220> FEATURE:
<223> OTHER INFORMATION: CD38 hScFv binder M8DR H_L

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Val Ser Gly Phe Thr Phe Asn Ser Phe
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Gly Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Phe Cys
                85                  90                  95

Ala Lys Asp Lys Ile Leu Trp Phe Gly Glu Pro Val Phe Asp Tyr Trp
            100                 105                 110

Gly Gln Gly Thr Leu Val Thr Val Ser Ser Ala Ser Gly Gly Gly Gly
        115                 120                 125

Ser Gly Gly Gly Gly Ser Gly Gly Gly Gly Ser Glu Ile Val Leu Thr
    130                 135                 140

Gln Ser Pro Ala Thr Leu Ser Leu Ser Pro Gly Glu Arg Ala Thr Leu
145                 150                 155                 160

Ser Cys Arg Ala Ser Gln Ser Val Ser Ser Tyr Leu Ala Trp Tyr Gln
                165                 170                 175

Gln Lys Pro Gly Gln Ala Pro Arg Leu Leu Ile Tyr Asp Ala Ser Asn
            180                 185                 190

Arg Ala Thr Gly Ile Pro Ala Arg Phe Ser Gly Ser Gly Ser Gly Thr
        195                 200                 205

Asp Phe Thr Leu Thr Ile Ser Ser Leu Glu Pro Glu Asp Phe Ala Val
    210                 215                 220

Tyr Tyr Cys Gln Gln Arg Ser Asn Trp Pro Pro Thr Phe Gly Gln Gly
225                 230                 235                 240

Thr Lys Val Glu Ile Lys
                245
```

<210> SEQ ID NO 75
<211> LENGTH: 732
<212> TYPE: DNA
<213> ORGANISM: Artificial Sequence
<220> FEATURE:
<223> OTHER INFORMATION: CD38 hScFv binder M8DR L_H

<400> SEQUENCE: 75

```
gaaattgttt tgactcagag tcctgcgaca ttgagcttga gtccgggtga acgggctact      60

cttagttgcc gcgcctcaca gtccgtatct tcatacctcg cctggtatca acagaagccg     120

gggcaggccc ctcgcctgct tatatatgat gccagcaata gagctactgg aatacctgcc     180

cgattttctg ggtctggaag tgggacggat ttcacactga caatatcttc tcttgagccg     240

gaagactttg ccgtctatta ctgccaacag cgctctaact ggccgcccac gtttggtcag     300

ggaacaaagg tagagataaa ggggggcggt ggctccggtg gggagggag cggaggaggt      360

ggttctgaag tccagcttct cgaatccggt gggggtctgg ttcaacctgg aggtagtctc     420

cgcttgtcct gtgctgtctc agggttcaca tttaactctt ttgctatgtc ttgggttcgg     480

caagctcctg gcaagggcct ggagtgggtg tccgctatta gtggctccgg aggcggcacg     540

tactatgcag atagtgtgaa gggcaggttt actatttccc gggataactc taagaacacc     600

ctgtacttgc agatgaatag tttgcgagcc gaagacactg cagtgtattt ttgcgccaag     660

gataaaatac tctggtttgg cgagccggta tttgactatt gggggcaagg cacacttgtc     720

acagtatcca gc                                                         732
```

<210> SEQ ID NO 76
<211> LENGTH: 244
<212> TYPE: PRT
<213> ORGANISM: Artificial Sequence
<220> FEATURE:

<223> OTHER INFORMATION: CD38 hScFv binder M8DR L_H

<400> SEQUENCE: 76

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Gly Ser Glu Val Gln Leu Leu Glu
        115                 120                 125

Ser Gly Gly Gly Leu Val Gln Pro Gly Gly Ser Leu Arg Leu Ser Cys
    130                 135                 140

Ala Val Ser Gly Phe Thr Phe Asn Ser Phe Ala Met Ser Trp Val Arg
145                 150                 155                 160

Gln Ala Pro Gly Lys Gly Leu Glu Trp Val Ser Ala Ile Ser Gly Ser
                165                 170                 175

Gly Gly Gly Thr Tyr Tyr Ala Asp Ser Val Lys Gly Arg Phe Thr Ile
            180                 185                 190

Ser Arg Asp Asn Ser Lys Asn Thr Leu Tyr Leu Gln Met Asn Ser Leu
        195                 200                 205

Arg Ala Glu Asp Thr Ala Val Tyr Phe Cys Ala Lys Asp Lys Ile Leu
    210                 215                 220

Trp Phe Gly Glu Pro Val Phe Asp Tyr Trp Gly Gln Gly Thr Leu Val
225                 230                 235                 240

Thr Val Ser Ser
```

<210> SEQ ID NO 77
<211> LENGTH: 1482
<212> TYPE: DNA
<213> ORGANISM: Artificial Sequence
<220> FEATURE:
<223> OTHER INFORMATION: LTG 2089

<400> SEQUENCE: 77

```
atgctgctgc tggtgaccag cctgctgctg tgcgaactgc cgcatccggc gtttctgctg     60

attccggaag tgcaattggt ccaaagcggt gcagaagtca agaaacctgg ttcgagcgtg    120

aaagtgtcct gcaaggcctc tggcggcacc ttctcatcct acgccattag ctgggtccgc    180

caagccccgg gccagggact tgagtggatg ggcggaatca tccctatctt cgggaccgcc    240

aattacgccc agaagttcca gggccgcgtg accatcaccg cggacaagtc cacatcaacc    300

gcctatatgg agctctcgtc gctgagatca gaggacactg ctgtctacta ctgtgcgagg    360

gccccatacg acgatgcatt cgacatctgg ggacagggta ccatggtcac tgtgtccagc    420

gggggcggag gctccggggg gggcggatcg gggggcggcg gatccaactt catgctgacc    480

cagccgcact cggtgtcaga gagccccgga aagactgtga ccattagctg cacccggtcc    540
```

```
agcggaagca tcgcctccaa ctacgtgcag tggtaccagc agcggccggg ctccgcgccg     600

accactgtga tctacgaaga taaccagcgc ccctccggtg tccctggacg gttctccgga     660

tccattgaca cctcgtccaa ctccgcctcg ctgacgatct ccggactgga gactgaagat     720

gaagctgtgt actactgcca atcctacgac tccggatttc cctacgccgt gttcggtggc     780

gggacccagc tcaccgtgct gggagcggcc gcaactacca cccctgcccc tcggccgccg     840

actccggccc caaccatcgc aagccaaccc ctctccttgc gccccgaagc ttgccgcccg     900

gccgcgggtg gagccgtgca tacccggggg ctggactttg cctgcgatat ctacatttgg     960

gccccgctgg ccggcacttg cggcgtgctc ctgctgtcgc tggtcatcac cctttactgc    1020

aagaggggcc ggaagaagct gctttacatc ttcaagcagc cgttcatgcg gcccgtgcag    1080

acgactcagg aagaggacgg atgctcgtgc agattccctg aggaggaaga gggggggatgc    1140

gaactgcgcg tcaagttctc acggtccgcc gacgcccccg catatcaaca gggccagaat    1200

cagctctaca acgagctgaa cctgggaagg agagaggagt acgacgtgct ggacaagcga    1260

cgcggacgcg acccggagat ggggggggaaa ccacggcgga aaaaccctca ggaaggactg    1320

tacaacgaac tccagaaaga caagatggcg gaagcctact cagaaatcgg gatgaaggga    1380

gagcggagga ggggaaaggg tcacgacggg ctgtaccagg gactgagcac cgccactaag    1440

gatacctacg atgccttgca tatgcaagca ctcccacccc gg                       1482
```

```
<210> SEQ ID NO 78
<211> LENGTH: 494
<212> TYPE: PRT
<213> ORGANISM: Artificial Sequence
<220> FEATURE:
<223> OTHER INFORMATION: LTG 2089

<400> SEQUENCE: 78

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn Tyr Ala Gln Lys Phe Gln Gly Arg Val Thr Ile Thr Ala Asp Lys
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Arg Ala Pro Tyr Asp Asp Ala Phe Asp
        115                 120                 125

Ile Trp Gly Gln Gly Thr Met Val Thr Val Ser Ser Gly Gly Gly Gly
    130                 135                 140

Ser Gly Gly Gly Gly Ser Gly Gly Gly Gly Ser Asn Phe Met Leu Thr
145                 150                 155                 160

Gln Pro His Ser Val Ser Glu Ser Pro Gly Lys Thr Val Thr Ile Ser
                165                 170                 175

Cys Thr Arg Ser Ser Gly Ser Ile Ala Ser Asn Tyr Val Gln Trp Tyr
            180                 185                 190

Gln Gln Arg Pro Gly Ser Ala Pro Thr Thr Val Ile Tyr Glu Asp Asn
```

```
        195                 200                 205

Gln Arg Pro Ser Gly Val Pro Gly Arg Phe Ser Gly Ser Ile Asp Thr
    210                 215                 220

Ser Ser Asn Ser Ala Ser Leu Thr Ile Ser Gly Leu Glu Thr Glu Asp
225                 230                 235                 240

Glu Ala Val Tyr Tyr Cys Gln Ser Tyr Asp Ser Gly Phe Pro Tyr Ala
                245                 250                 255

Val Phe Gly Gly Gly Thr Gln Leu Thr Val Leu Gly Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 79
<211> LENGTH: 36
<212> TYPE: DNA
<213> ORGANISM: Artificial Sequence
<220> FEATURE:
<223> OTHER INFORMATION: human IgG4 hinge

<400> SEQUENCE: 79

```
gagagcaaat acgggccgcc atgtcccccg tgtccg                              36
```

<210> SEQ ID NO 80
<211> LENGTH: 12
<212> TYPE: PRT
<213> ORGANISM: Artificial Sequence
<220> FEATURE:
<223> OTHER INFORMATION: human IgG4 hinge

<400> SEQUENCE: 80

```
Glu Ser Lys Tyr Gly Pro Pro Cys Pro Pro Cys Pro
```

```
1               5                   10


<210> SEQ ID NO 81
<211> LENGTH: 327
<212> TYPE: DNA
<213> ORGANISM: Artificial Sequence
<220> FEATURE:
<223> OTHER INFORMATION: human IgG4 CH2 domain

<400> SEQUENCE: 81

gcaccaccag ttgctggccc tagtgtcttc ttgttccctc ccaagcccaa agacaccttg     60

atgatttcca gaactcctga ggttacctgc gttgtcgtag atgtttctca ggaggaccca    120

gaggtccaat ttaactggta cgttgatggg gtggaagttc acaatgcgaa gacaaagccg    180

cgggaagaac aatttcagtc cacttaccgg gttgtcagcg ttctgacggt attgcatcaa    240

gactggctta atggaaagga atataagtgt aaggtgtcca acaaaggttt gccgagcagt    300

attgagaaga ccatatcaaa ggcgaag                                        327


<210> SEQ ID NO 82
<211> LENGTH: 109
<212> TYPE: PRT
<213> ORGANISM: Artificial Sequence
<220> FEATURE:
<223> OTHER INFORMATION: human IgG4 CH2 domain

<400> SEQUENCE: 82

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105


<210> SEQ ID NO 83
<211> LENGTH: 321
<212> TYPE: DNA
<213> ORGANISM: Artificial Sequence
<220> FEATURE:
<223> OTHER INFORMATION: human IgG4 CH3 domain

<400> SEQUENCE: 83

gggcagccgc gcgagccaca agtttacact ttgccgccat ctcaagagga aatgactaaa     60

aaccaggtat ccttgacatg cctcgtaaaa ggattttatc catctgatat tgctgtggaa    120

tgggagtcta acgggcagcc ggaaaataat tacaaaacta caccacctgt gctcgattca    180

gatggaagtt tcttccttta cagtagactt acggtggaca aatctaggtg gcaggaaggg    240

aatgtgttta gttgtagtgt aatgcacgag gcacttcata accactatac acagaagtca    300

ctgagtttga gtcttggcaa a                                              321


<210> SEQ ID NO 84
```

<211> LENGTH: 107
<212> TYPE: PRT
<213> ORGANISM: Artificial Sequence
<220> FEATURE:
<223> OTHER INFORMATION: human IgG4 CH3 domain

<400> SEQUENCE: 84

```
Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105
```

<210> SEQ ID NO 85
<211> LENGTH: 684
<212> TYPE: DNA
<213> ORGANISM: Artificial Sequence
<220> FEATURE:
<223> OTHER INFORMATION: human IgG4 hinge CH2 CH3 domain

<400> SEQUENCE: 85

```
gagagcaaat acgggccgcc atgtcccccg tgtccggcac caccagttgc tggccctagt     60

gtcttcttgt tccctcccaa gcccaaagac accttgatga tttccagaac tcctgaggtt    120

acctgcgttg tcgtagatgt ttctcaggag gacccagagg tccaatttaa ctggtacgtt    180

gatggggtgg aagttcacaa tgcgaagaca aagccgcggg aagaacaatt tcagtccact    240

taccgggttg tcagcgttct gacggtattg catcaagact ggcttaatgg aaaggaatat    300

aagtgtaagg tgtccaacaa aggtttgccg agcagtattg agaagaccat atcaaaggcg    360

aaggggcagc cgcgcgagcc acaagtttac actttgccgc catctcaaga ggaaatgact    420

aaaaaccagg tatccttgac atgcctcgta aaaggatttt atccatctga tattgctgtg    480

gaatgggagt ctaacgggca gccggaaaat aattacaaaa ctacaccacc tgtgctcgat    540

tcagatggaa gtttcttcct ttacagtaga cttacggtgg acaaatctag gtggcaggaa    600

gggaatgtgt ttagttgtag tgtaatgcac gaggcacttc ataaccacta tacacagaag    660

tcactgagtt tgagtcttgg caaa                                            684
```

<210> SEQ ID NO 86
<211> LENGTH: 228
<212> TYPE: PRT
<213> ORGANISM: Artificial Sequence
<220> FEATURE:
<223> OTHER INFORMATION: human IgG4 hinge CH2 CH3 domain

<400> SEQUENCE: 86

```
Glu Ser Lys Tyr Gly Pro Pro Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30
```

-continued

```
Met Ile Ser Arg Thr Pro Glu Val Thr Cys Val Val Val Asp Val Ser
        35                  40                  45

Gln Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Gln Ser Thr
65                  70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Gly Leu Pro Ser Ser
            100                 105                 110

Ile Glu Lys Thr Ile Ser Lys Ala Lys Gly Gln Pro Arg Glu Pro Gln
        115                 120                 125

Val Tyr Thr Leu Pro Pro Ser Gln Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Arg Leu Thr
            180                 185                 190

Val Asp Lys Ser Arg Trp Gln Glu Gly Asn Val Phe Ser Cys Ser Val
        195                 200                 205

Met His Glu Ala Leu His Asn His Tyr Thr Gln Lys Ser Leu Ser Leu
    210                 215                 220

Ser Leu Gly Lys
225
```

```
<210> SEQ ID NO 87
<211> LENGTH: 1479
<212> TYPE: DNA
<213> ORGANISM: Artificial Sequence
<220> FEATURE:
<223> OTHER INFORMATION: LTG 2090

<400> SEQUENCE: 87

atgctgctgc tggtgaccag cctgctgctg tgcgaactgc cgcatccggc gtttctgctg      60

attccggaag tgcaactcgt cgaatctggt ggaggatccg tgcagcctgg tggaagcctg     120

agactgtcgt gtgccgcctc cgagttcacc ttctcctcgt actggatgca ctgggtcaga     180

caggcgcccg gaaagggcct ggaatgggtg gccgtgatct catacgacgg cgcgaagaag     240

tactacgccg attccgtgaa gggccgcttt accatttccc gggacaattc aaagaacacc     300

ctctaccttc aaatgaactc cctgagggcc gaggatactg cagtctacta ctgcgctcgg     360

gatgacggga gcgggggctt cgactactgg ggacagggaa ccctcgtgac tgtgtcatcc     420

ggtggcggcg gctccggagg cggcggttcc gggggggggg gatccgacat cgtgatgacg     480

cacactcctc tgtcgctgtc cgtgaccccc ggccagcctg cctcaatctc gtgcaagagc     540

tcccagtcgc tgctgcatag cgatggaaag acctacctgt attggtacct tcaaaagccg     600

ggacagccgc cgcagttgct gatctatgaa gtcagcaacc gcttctcggg agtgcccgac     660

cgctactccg gctcggggag cggaaccgac ttcaccctga aaatttcccg ggtcgaggca     720

gaggacgtgg gagtgtacta ctgcatgcaa agcattcagt tgccactgac tttcggtgga     780

ggaaccaagc tcgaaatcaa agcggccgca actaccaccc ctgcccctcg gccgccgact     840

ccggccccaa ccatcgcaag ccaacccctc tccttgcgcc ccgaagcttg ccgcccggcc     900
```

```
gcgggtggag ccgtgcatac ccgggggctg gactttgcct gcgatatcta catttgggcc    960

ccgctggccg gcacttgcgg cgtgctcctg ctgtcgctgg tcatcaccct ttactgcaag   1020

aggggccgga agaagctgct ttacatcttc aagcagccgt tcatgcggcc cgtgcagacg   1080

actcaggaag aggacggatg ctcgtgcaga ttccctgagg aggaagaggg gggatgcgaa   1140

ctgcgcgtca agttctcacg gtccgccgac gcccccgcat atcaacaggg ccagaatcag   1200

ctctacaacg agctgaacct gggaaggaga gaggagtacg acgtgctgga caagcgacgc   1260

ggacgcgacc cggagatggg ggggaaacca cggcggaaaa accctcagga aggactgtac   1320

aacgaactcc agaaagacaa gatggcggaa gcctactcag aaatcgggat gaagggagag   1380

cggaggaggg gaaagggtca cgacgggctg taccagggac tgagcaccgc cactaaggat   1440

acctacgatg ccttgcatat gcaagcactc ccaccccgg                          1479
```

```
<210> SEQ ID NO 88
<211> LENGTH: 493
<212> TYPE: PRT
<213> ORGANISM: Artificial Sequence
<220> FEATURE:
<223> OTHER INFORMATION: LTG 2090

<400> SEQUENCE: 88

Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Ser Val Gln Pro Gly Gly Ser Leu Arg Leu Ser Cys Ala Ala Ser Glu
        35                  40                  45

Phe Thr Phe Ser Ser Tyr Trp Met His Trp Val Arg Gln Ala Pro Gly
    50                  55                  60

Lys Gly Leu Glu Trp Val Ala Val Ile Ser Tyr Asp Gly Ala Lys Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala Arg Asp Asp Gly Ser Gly Gly Phe Asp
        115                 120                 125

Tyr Trp Gly Gln Gly Thr Leu Val Thr Val Ser Ser Gly Gly Gly Gly
    130                 135                 140

Ser Gly Gly Gly Gly Ser Gly Gly Gly Gly Ser Asp Ile Val Met Thr
145                 150                 155                 160

His Thr Pro Leu Ser Leu Ser Val Thr Pro Gly Gln Pro Ala Ser Ile
                165                 170                 175

Ser Cys Lys Ser Ser Gln Ser Leu Leu His Ser Asp Gly Lys Thr Tyr
            180                 185                 190

Leu Tyr Trp Tyr Leu Gln Lys Pro Gly Gln Pro Pro Gln Leu Leu Ile
        195                 200                 205

Tyr Glu Val Ser Asn Arg Phe Ser Gly Val Pro Asp Arg Tyr Ser Gly
    210                 215                 220

Ser Gly Ser Gly Thr Asp Phe Thr Leu Lys Ile Ser Arg Val Glu Ala
225                 230                 235                 240

Glu Asp Val Gly Val Tyr Tyr Cys Met Gln Ser Ile Gln Leu Pro Leu
                245                 250                 255

Thr Phe Gly Gly Gly Thr Lys Leu Glu Ile Lys Ala Ala Ala Thr Thr
```

```
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490


<210> SEQ ID NO 89
<211> LENGTH: 1494
<212> TYPE: DNA
<213> ORGANISM: Artificial Sequence
<220> FEATURE:
<223> OTHER INFORMATION: LTG 2091

<400> SEQUENCE: 89

atgctgctgc tggtgaccag cctgctgctg tgcgaactgc cgcatccggc gtttctgctg      60

attccggaag tgcaattggt gcagagcggt ggaggacttg tgaaacctgg tggatccctg     120

agactttcct gtgccgcttc gggcttcacc ttctcggact actacatgtc ctggattcgc     180

caggcccctg gaaagggact ggaatgggtg tcatacatca gctcctccgg ttccaccatc     240

tactatgccg attccgtgaa gggcagattc accatctcgc gcgacaacgc caagaacact     300

ctctatctgc aaatgaactc actgcgggct gaggacaccg cggtctacta ctgcgcccgg     360

gacctcagcg gaaagtccag cggatggtcc cattacttcg attactgggg acagggaacc     420

ctggtcaccg tgtccagcgg cggggggggc tcgggtggcg gcggctccgg cggcggcggg     480

agcaacttca tgctgactca gccccactcc gtgtccgaga gcccgggaaa gaccgtgact     540

atttcgtgca cacggtcctc cgggagcatt gcgaacaact acgtgcagtg gtaccagcag     600

cggcccgata gggccccaac cactgtgatc tacgaagatg accagcggcc gtctggagtc     660

ccggaccgct tctcggggtc catcgactca tcatccaatt ccgcatcgct gacgatcagc     720

ggactgaaga tcgaggacga agccgattac tactgccagt cctacgacgg caccaactgg     780
```

```
gtctttgggg gtggaaccaa gctgactgtg ctcggagcgg ccgcaactac cacccctgcc    840
cctcggccgc cgactccggc cccaaccatc gcaagccaac ccctctcctt gcgccccgaa    900
gcttgccgcc cggccgcggg tggagccgtg catacccggg ggctggactt tgcctgcgat    960
atctacattt gggccccgct ggccggcact tgcggcgtgc tcctgctgtc gctggtcatc   1020
accctttact gcaagagggg ccggaagaag ctgctttaca tcttcaagca gccgttcatg   1080
cggcccgtgc agacgactca ggaagaggac ggatgctcgt gcagattccc tgaggaggaa   1140
gagggggggat gcgaactgcg cgtcaagttc tcacggtccg ccgacgcccc cgcatatcaa   1200
cagggccaga atcagctcta caacgagctg aacctgggaa ggagagagga gtacgacgtg   1260
ctggacaagc gacgcggacg cgacccggag atggggggga aaccacggcg gaaaaaccct   1320
caggaaggac tgtacaacga actccagaaa gacaagatgg cggaagccta ctcagaaatc   1380
gggatgaagg gagagcggag gaggggaaag ggtcacgacg ggctgtacca gggactgagc   1440
accgccacta aggataccta cgatgccttg catatgcaag cactcccacc ccgg         1494
```

```
<210> SEQ ID NO 90
<211> LENGTH: 498
<212> TYPE: PRT
<213> ORGANISM: Artificial Sequence
<220> FEATURE:
<223> OTHER INFORMATION: LTG 2091

<400> SEQUENCE: 90

Met Leu Leu Leu Val Thr Ser Leu Leu Leu Cys Glu Leu Pro His Pro
1               5                   10                  15

Ala Phe Leu Leu Ile Pro Glu Val Gln Leu Val Gln Ser Gly Gly Gly
            20                  25                  30

Leu Val Lys Pro Gly Gly Ser Leu Arg Leu Ser Cys Ala Ala Ser Gly
        35                  40                  45

Phe Thr Phe Ser Asp Tyr Tyr Met Ser Trp Ile Arg Gln Ala Pro Gly
    50                  55                  60

Lys Gly Leu Glu Trp Val Ser Tyr Ile Ser Ser Ser Gly Ser Thr Ile
65                  70                  75                  80

Tyr Tyr Ala Asp Ser Val Lys Gly Arg Phe Thr Ile Ser Arg Asp Asn
                85                  90                  95

Ala Lys Asn Thr Leu Tyr Leu Gln Met Asn Ser Leu Arg Ala Glu Asp
            100                 105                 110

Thr Ala Val Tyr Tyr Cys Ala Arg Asp Leu Ser Gly Lys Ser Ser Gly
        115                 120                 125

Trp Ser His Tyr Phe Asp Tyr Trp Gly Gln Gly Thr Leu Val Thr Val
    130                 135                 140

Ser Ser Gly Gly Gly Gly Ser Gly Gly Gly Gly Ser Gly Gly Gly Gly
145                 150                 155                 160

Ser Asn Phe Met Leu Thr Gln Pro His Ser Val Ser Glu Ser Pro Gly
                165                 170                 175

Lys Thr Val Thr Ile Ser Cys Thr Arg Ser Ser Gly Ser Ile Ala Asn
            180                 185                 190

Asn Tyr Val Gln Trp Tyr Gln Gln Arg Pro Asp Arg Ala Pro Thr Thr
        195                 200                 205

Val Ile Tyr Glu Asp Asp Gln Arg Pro Ser Gly Val Pro Asp Arg Phe
    210                 215                 220

Ser Gly Ser Ile Asp Ser Ser Ser Asn Ser Ala Ser Leu Thr Ile Ser
225                 230                 235                 240
```

```
Gly Leu Lys Ile Glu Asp Glu Ala Asp Tyr Tyr Cys Gln Ser Tyr Asp
                245                 250                 255

Gly Thr Asn Trp Val Phe Gly Gly Gly Thr Lys Leu Thr Val Leu Gly
            260                 265                 270

Ala Ala Ala Thr Thr Thr Pro Ala Pro Arg Pro Pro Thr Pro Ala Pro
        275                 280                 285

Thr Ile Ala Ser Gln Pro Leu Ser Leu Arg Pro Glu Ala Cys Arg Pro
    290                 295                 300

Ala Ala Gly Gly Ala Val His Thr Arg Gly Leu Asp Phe Ala Cys Asp
305                 310                 315                 320

Ile Tyr Ile Trp Ala Pro Leu Ala Gly Thr Cys Gly Val Leu Leu Leu
                325                 330                 335

Ser Leu Val Ile Thr Leu Tyr Cys Lys Arg Gly Arg Lys Lys Leu Leu
            340                 345                 350

Tyr Ile Phe Lys Gln Pro Phe Met Arg Pro Val Gln Thr Thr Gln Glu
        355                 360                 365

Glu Asp Gly Cys Ser Cys Arg Phe Pro Glu Glu Glu Glu Gly Gly Cys
    370                 375                 380

Glu Leu Arg Val Lys Phe Ser Arg Ser Ala Asp Ala Pro Ala Tyr Gln
385                 390                 395                 400

Gln Gly Gln Asn Gln Leu Tyr Asn Glu Leu Asn Leu Gly Arg Arg Glu
                405                 410                 415

Glu Tyr Asp Val Leu Asp Lys Arg Arg Gly Arg Asp Pro Glu Met Gly
            420                 425                 430

Gly Lys Pro Arg Arg Lys Asn Pro Gln Glu Gly Leu Tyr Asn Glu Leu
        435                 440                 445

Gln Lys Asp Lys Met Ala Glu Ala Tyr Ser Glu Ile Gly Met Lys Gly
    450                 455                 460

Glu Arg Arg Arg Gly Lys Gly His Asp Gly Leu Tyr Gln Gly Leu Ser
465                 470                 475                 480

Thr Ala Thr Lys Asp Thr Tyr Asp Ala Leu His Met Gln Ala Leu Pro
                485                 490                 495

Pro Arg
```

<210> SEQ ID NO 91
<211> LENGTH: 1473
<212> TYPE: DNA
<213> ORGANISM: Artificial Sequence
<220> FEATURE:
<223> OTHER INFORMATION: LTG 2092

<400> SEQUENCE: 91

```
atgctgctgc tggtgaccag cctgctgctg tgcgaactgc cgcatccggc gtttctgctg     60

attccggaag tgcaacttgt cgaaagcggt ggaggtcttg tccaacctgg tcgctccctg    120

aggctctcgt gtgccgcgag cggattcacc ttctcatcgt acgctatgtc ctgggtcaga    180

caggctcctg gaaagggcct ggaatgggtg gccgtgatct cctacgacgg cagcaacaag    240

tattacgccg actcagtgaa gggccggttc accatttccc gggacaacag caagaacacc    300

ctgtacttgc aaatgaactc cctgcgggcc gaggataccg cggtgtacta ctgcgcccac    360

ctccgctttg gatacggaat ggatgtctgg ggacagggaa ctaccgtgac cgtgtcgtcc    420

gggggggggg gaagcggcgg cgggggatcg ggtggcggcg gatcccagac tgtggtcacc    480

caagagcctt cactgaccgt gtccccgggt ggcaccgtga cgctgacttg cgcgtcatct    540
```

```
accggggccg tgacctcgga ccactacccc tgctggttcc agcagaaacc cggacatcca    600

ccgagagccc tggtgtactc cactgacacc atccactcct ggactccggc ccggttctcc    660

ggaagcctcc tgggcgggaa ggccgcactg acagtgtccg gagtgcagcc cgaggatgaa    720

gccgactact actgtctgct ctactatggg ggagcacgcg tgttcggtgg cggcactcag    780

ctgaccgtgc tgggagcggc cgcaactacc acccctgccc ctcggccgcc gactccggcc    840

ccaaccatcg caagccaacc cctctccttg cgccccgaag cttgccgccc ggccgcgggt    900

ggagccgtgc atacccgggg gctggacttt gcctgcgata tctacatttg ggccccgctg    960

gccggcactt gcggcgtgct cctgctgtcg ctggtcatca ccctttactg caagaggggc   1020

cggaagaagc tgctttacat cttcaagcag ccgttcatgc ggcccgtgca gacgactcag   1080

gaagaggacg gatgctcgtg cagattccct gaggaggaag aggggggatg cgaactgcgc   1140

gtcaagttct cacggtccgc cgacgccccc gcatatcaac agggccagaa tcagctctac   1200

aacgagctga acctgggaag gagagaggag tacgacgtgc tggacaagcg acgcggacgc   1260

gacccggaga tggggggaa accacggcgg aaaaaccctc aggaaggact gtacaacgaa   1320

ctccagaaag acaagatggc ggaagcctac tcagaaatcg ggatgaaggg agagcggagg   1380

aggggaaagg gtcacgacgg gctgtaccag ggactgagca ccgccactaa ggatacctac   1440

gatgccttgc atatgcaagc actcccaccc cgg                                1473
```

<210> SEQ ID NO 92
<211> LENGTH: 491
<212> TYPE: PRT
<213> ORGANISM: Artificial Sequence
<220> FEATURE:
<223> OTHER INFORMATION: LTG 2092 (hScFv aCD38 CD8 TM 4-1BB CD3 zeta)

<400> SEQUENCE: 92

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Arg Ser Leu Arg Leu Ser Cys Ala Ala Ser Gly
        35                  40                  45

Phe Thr Phe Ser Ser Tyr Ala Met Ser Trp Val Arg Gln Ala Pro Gly
    50                  55                  60

Lys Gly Leu Glu Trp Val Ala Val Ile Ser Tyr Asp Gly Ser Asn Lys
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Tyr Cys Ala His Leu Arg Phe Gly Tyr Gly Met Asp
        115                 120                 125

Val Trp Gly Gln Gly Thr Thr Val Thr Val Ser Ser Gly Gly Gly Gly
    130                 135                 140

Ser Gly Gly Gly Gly Ser Gly Gly Gly Gly Ser Gln Thr Val Val Thr
145                 150                 155                 160

Gln Glu Pro Ser Leu Thr Val Ser Pro Gly Gly Thr Val Thr Leu Thr
                165                 170                 175

Cys Ala Ser Ser Thr Gly Ala Val Thr Ser Asp His Tyr Pro Cys Trp
            180                 185                 190

Phe Gln Gln Lys Pro Gly His Pro Pro Arg Ala Leu Val Tyr Ser Thr
```

```
        195                 200                 205

Asp Thr Ile His Ser Trp Thr Pro Ala Arg Phe Ser Gly Ser Leu Leu
    210                 215                 220

Gly Gly Lys Ala Ala Leu Thr Val Ser Gly Val Gln Pro Glu Asp Glu
225                 230                 235                 240

Ala Asp Tyr Tyr Cys Leu Leu Tyr Tyr Gly Gly Ala Arg Val Phe Gly
                245                 250                 255

Gly Gly Thr Gln Leu Thr Val Leu Gly Ala Ala Ala Thr Thr Thr Pro
            260                 265                 270

Ala Pro Arg Pro Pro Thr Pro Ala Pro Thr Ile Ala Ser Gln Pro Leu
        275                 280                 285

Ser Leu Arg Pro Glu Ala Cys Arg Pro Ala Ala Gly Gly Ala Val His
    290                 295                 300

Thr Arg Gly Leu Asp Phe Ala Cys Asp Ile Tyr Ile Trp Ala Pro Leu
305                 310                 315                 320

Ala Gly Thr Cys Gly Val Leu Leu Leu Ser Leu Val Ile Thr Leu Tyr
                325                 330                 335

Cys Lys Arg Gly Arg Lys Lys Leu Leu Tyr Ile Phe Lys Gln Pro Phe
            340                 345                 350

Met Arg Pro Val Gln Thr Thr Gln Glu Glu Asp Gly Cys Ser Cys Arg
        355                 360                 365

Phe Pro Glu Glu Glu Glu Gly Gly Cys Glu Leu Arg Val Lys Phe Ser
    370                 375                 380

Arg Ser Ala Asp Ala Pro Ala Tyr Gln Gln Gly Gln Asn Gln Leu Tyr
385                 390                 395                 400

Asn Glu Leu Asn Leu Gly Arg Arg Glu Glu Tyr Asp Val Leu Asp Lys
                405                 410                 415

Arg Arg Gly Arg Asp Pro Glu Met Gly Gly Lys Pro Arg Arg Lys Asn
            420                 425                 430

Pro Gln Glu Gly Leu Tyr Asn Glu Leu Gln Lys Asp Lys Met Ala Glu
        435                 440                 445

Ala Tyr Ser Glu Ile Gly Met Lys Gly Glu Arg Arg Arg Gly Lys Gly
    450                 455                 460

His Asp Gly Leu Tyr Gln Gly Leu Ser Thr Ala Thr Lys Asp Thr Tyr
465                 470                 475                 480

Asp Ala Leu His Met Gln Ala Leu Pro Pro Arg
                485                 490


<210> SEQ ID NO 93
<211> LENGTH: 1479
<212> TYPE: DNA
<213> ORGANISM: Artificial Sequence
<220> FEATURE:
<223> OTHER INFORMATION: LTG 2093 (hScFv aCD38 CD8 TM 4-1BB CD3 zeta)

<400> SEQUENCE: 93

atgctgctgc tggtgaccag cctgctgctg tgcgaactgc cgcatccggc gtttctgctg      60

attccgcaag tgcaactcgt ccaatccgga gctgaagtca agaagccagg atcttccgtg     120

aaagtgtcgt gcaaggcctc cgggggaaca ttctcctcat atgcgatcag ctgggtccgc     180

caggctccgg gacagggctt ggagtggatg ggtatcatta acccttcggg cggctcaact     240

agctacgccc agaagttcca gggcagagtg accatgacca gggacaccag cacttcgacg     300

gtgtacatgg aactgtcctc actgcggtcc gaggacaccg ccgtgtacta ctgcgcccgg     360

gagtattcct cctcccgcgt ggacgccttc gatatctggg gacagggtac catggtcact     420
```

```
gtgtcgtccg gcggcggcgg aagcgggggt ggcgggagcg gtggcggcgg atccagctac    480

gaactcaccc agccgccgtc agtgtccgtg agcccgggac agaccgcaac cattacttgt    540

tccggggatg acctgggatc caaatacgtg tgctggtacc aacagaagcc tggtcactcg    600

cccgtgctga tcatctacga cgactcagac cggcccagcg gcatccccga gagattttcc    660

ggatccaaca gcggaaacac cgccactctg actatttcgc gcgtcgaggc cggcgacgaa    720

gcggattact actgccaagt ctgggacagc tcctcggatc atgccgtgtt cgggggcgga    780

acccagctta ccgtgctggg ggcggccgca actaccaccc ctgcccctcg gccgccgact    840

ccggccccaa ccatcgcaag ccaacccctc tccttgcgcc ccgaagcttg ccgcccggcc    900

gcgggtggag ccgtgcatac ccgggggctg gactttgcct gcgatatcta catttgggcc    960

ccgctggccg gcacttgcgg cgtgctcctg ctgtcgctgg tcatcaccct ttactgcaag   1020

aggggccgga agaagctgct ttacatcttc aagcagccgt tcatgcggcc cgtgcagacg   1080

actcaggaag aggacggatg ctcgtgcaga ttccctgagg aggaagaggg gggatgcgaa   1140

ctgcgcgtca agttctcacg gtccgccgac gcccccgcat atcaacaggg ccagaatcag   1200

ctctacaacg agctgaacct gggaaggaga gaggagtacg acgtgctgga caagcgacgc   1260

ggacgcgacc cggagatggg ggggaaacca cggcggaaaa accctcagga aggactgtac   1320

aacgaactcc agaaagacaa gatggcggaa gcctactcag aaatcgggat gaagggagag   1380

cggaggaggg gaaagggtca cgacgggctg taccagggac tgagcaccgc cactaaggat   1440

acctacgatg ccttgcatat gcaagcactc ccaccccgg                          1479
```

```
<210> SEQ ID NO 94
<211> LENGTH: 493
<212> TYPE: PRT
<213> ORGANISM: Artificial Sequence
<220> FEATURE:
<223> OTHER INFORMATION: LTG 2093 (hScFv aCD38 CD8 TM 4-1BB CD3 zeta)

<400> SEQUENCE: 94

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Ile Ile Asn Pro Ser Gly Gly Ser Thr
65                  70                  75                  80

Ser Tyr Ala Gln Lys Phe Gln Gly Arg Val Thr Met Thr Arg Asp Thr
                85                  90                  95

Ser Thr Ser Thr Val Tyr Met Glu Leu Ser Ser Leu Arg Ser Glu Asp
            100                 105                 110

Thr Ala Val Tyr Tyr Cys Ala Arg Glu Tyr Ser Ser Ser Arg Val Asp
        115                 120                 125

Ala Phe Asp Ile Trp Gly Gln Gly Thr Met Val Thr Val Ser Ser Gly
    130                 135                 140

Gly Gly Gly Ser Gly Gly Gly Gly Ser Gly Gly Gly Gly Ser Ser Tyr
145                 150                 155                 160

Glu Leu Thr Gln Pro Pro Ser Val Ser Val Ser Pro Gly Gln Thr Ala
                165                 170                 175
```

```
Thr Ile Thr Cys Ser Gly Asp Asp Leu Gly Ser Lys Tyr Val Cys Trp
            180                 185                 190

Tyr Gln Gln Lys Pro Gly His Ser Pro Val Leu Ile Ile Tyr Asp Asp
        195                 200                 205

Ser Asp Arg Pro Ser Gly Ile Pro Glu Arg Phe Ser Gly Ser Asn Ser
    210                 215                 220

Gly Asn Thr Ala Thr Leu Thr Ile Ser Arg Val Glu Ala Gly Asp Glu
225                 230                 235                 240

Ala Asp Tyr Tyr Cys Gln Val Trp Asp Ser Ser Ser Asp His Ala Val
                245                 250                 255

Phe Gly Gly Gly Thr Gln Leu Thr Val Leu Gly Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 95
<211> LENGTH: 1461
<212> TYPE: DNA
<213> ORGANISM: Artificial Sequence
<220> FEATURE:
<223> OTHER INFORMATION: LTG 2094 (hScFv aCD38 CD8 TM 4-1BB CD3 zeta)

<400> SEQUENCE: 95

```
atgctgctgc tggtgaccag cctgctgctg tgcgaactgc cgcatccggc gtttctgctg      60

attccggaag tgcagttggt ggagagcggt ggaggacttg tgcaacctgg tggatccctg     120

agattgtcgt gtgccgcctc cggtttcacc ttctcctcgt actggatgag ctgggtccgc     180

caggcacccg ggaagggact ggaatgggtg gcggacatta aggatgacgg ctccgagcgg     240
```

```
tactacgtgg actccgtgaa gggccggttc actatctcaa gagacaatgc caagaacagc    300

ctgtacctcc aaatgaactc gctgcgggcc gaggataccg cagtgtatta ctgcgcccgc    360

gacgtgtggg ctgggatgga tgtctggggc caggggacca ctgtcactgt gtctagcggg    420

ggcggcggaa gcggcggcgg cggatccggt ggtggcggaa gcgacattca gctgacccag    480

tccccatcat tcctgtccgc ctccgtgggc gacagggtca ctatcacttg ccaagccagc    540

caggacatct ccaactacct gaactggtac cagcagaagc ctggaaaagc tccgaagctc    600

ctcatctacg acgcctcgaa cctcgaaacc ggagtgccct cacggttttc cggatcggga    660

tcggggaccg atttctcctt caccatttca tccctgcaac ccgaggacat cgcgacctac    720

tactgccaac agacatactc cccgccgatt acgttcggac agggaacccg cctggaaatc    780

aaggcggccg caactaccac ccctgcccct cggccgccga ctccggcccc aaccatcgca    840

agccaacccc tctccttgcg ccccgaagct tgccgcccgg ccgcgggtgg agccgtgcat    900

acccgggggc tggactttgc ctgcgatatc tacatttggg ccccgctggc cggcacttgc    960

ggcgtgctcc tgctgtcgct ggtcatcacc ctttactgca agaggggccg gaagaagctg   1020

ctttacatct tcaagcagcc gttcatgcgg cccgtgcaga cgactcagga agaggacgga   1080

tgctcgtgca gattccctga ggaggaagag gggggatgcg aactgcgcgt caagttctca   1140

cggtccgccg acgcccccgc atatcaacag ggccagaatc agctctacaa cgagctgaac   1200

ctgggaagga gagaggagta cgacgtgctg gacaagcgac gcggacgcga cccggagatg   1260

ggggggaaac cacggcggaa aaaccctcag gaaggactgt acaacgaact ccagaaagac   1320

aagatggcgg aagcctactc agaaatcggg atgaagggag agcggaggag gggaaagggt   1380

cacgacgggc tgtaccaggg actgagcacc gccactaagg atacctacga tgccttgcat   1440

atgcaagcac tcccaccccg g                                              1461
```

<210> SEQ ID NO 96
<211> LENGTH: 487
<212> TYPE: PRT
<213> ORGANISM: Artificial Sequence
<220> FEATURE:
<223> OTHER INFORMATION: LTG 2094 (hScFv aCD38 CD8 TM 4-1BB CD3 zeta)

<400> SEQUENCE: 96

```
Met Leu Leu Leu Val Thr Ser Leu Leu Leu Cys Glu Leu Pro His Pro
1               5                   10                  15

Ala Phe Leu Leu Ile Pro Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Phe Thr Phe Ser Ser Tyr Trp Met Ser Trp Val Arg Gln Ala Pro Gly
    50                  55                  60

Lys Gly Leu Glu Trp Val Ala Asp Ile Lys Asp Asp Gly Ser Glu Arg
65                  70                  75                  80

Tyr Tyr Val Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Asp Val Trp Ala Gly Met Asp Val
        115                 120                 125

Trp Gly Gln Gly Thr Thr Val Thr Val Ser Ser Gly Gly Gly Gly Ser
    130                 135                 140
```

```
Gly Gly Gly Gly Ser Gly Gly Gly Gly Ser Asp Ile Gln Leu Thr Gln
145                 150                 155                 160

Ser Pro Ser Phe Leu Ser Ala Ser Val Gly Asp Arg Val Thr Ile Thr
                165                 170                 175

Cys Gln Ala Ser Gln Asp Ile Ser Asn Tyr Leu Asn Trp Tyr Gln Gln
            180                 185                 190

Lys Pro Gly Lys Ala Pro Lys Leu Leu Ile Tyr Asp Ala Ser Asn Leu
        195                 200                 205

Glu Thr Gly Val Pro Ser Arg Phe Ser Gly Ser Gly Ser Gly Thr Asp
    210                 215                 220

Phe Ser Phe Thr Ile Ser Ser Leu Gln Pro Glu Asp Ile Ala Thr Tyr
225                 230                 235                 240

Tyr Cys Gln Gln Thr Tyr Ser Pro Pro Ile Thr Phe Gly Gln Gly Thr
                245                 250                 255

Arg Leu Glu Ile Lys Ala Ala Ala Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
        435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 97
<211> LENGTH: 1467
<212> TYPE: DNA
<213> ORGANISM: Artificial Sequence
<220> FEATURE:
<223> OTHER INFORMATION: LTG 2095 (hScFv aCD38 CD8 TM 4-1BB CD3 zeta)

<400> SEQUENCE: 97

```
atgctgctgc tggtgaccag cctgctgctg tgcgaactgc cgcatccggc gtttctgctg     60

attccgcaag tccaactcgt ccagtccggt gccgaagtca agaagcctgg ctcatccgtg    120
```

```
aaagtgtcct gcaaagcatc gggcggaacc ttctcctcct atgccatttc ctgggtccgc    180

caggcaccgg gccagggtct ggagtggatg ggcgggatta tccctatctt cggaactgcc    240

aaccacgccc aaaagttcca gggacgcgtg accattaccg ccgatgaatc aacctcaacc    300

gcctacatgg aactgtccag cttgaggtcc gaggacaccg ccgtgtacta ctgcgcgttc    360

atgatggtgc cggagtacta ctttgactac tggggccagg gaacccttgt gaccgtgtcg    420

tccggtggtg gcggatccgg gggggggga tctgggggcg gcggaagcga tatccagatg    480

acccagtcgc catcgagcct gtccgcttcc gtgggcgaca gagtgacgat cacttgccgg    540

gcttcacaag gcatcagaaa tgacctgggc tggtatcagc agaagcccgg agaagcgccc    600

aagcggctga tctacgcggc cagcaccctg caaaacggag tgccttcgcg gttctccggg    660

agcggctccg gaactgactt cactctgact attaacagcc tccagcccga ggatttcgcc    720

acatactact gtcagcagta caacagctac ccgtacacct tcggacaggg aactaagctc    780

gaaatcaagg cggccgcaac taccacccct gcccctcggc cgccgactcc ggccccaacc    840

atcgcaagcc aacccctctc cttgcgcccc gaagcttgcc gcccggccgc gggtggagcc    900

gtgcataccc gggggctgga ctttgcctgc gatatctaca tttgggcccc gctggccggc    960

acttgcggcg tgctcctgct gtcgctggtc atcacccttt actgcaagag gggccggaag   1020

aagctgcttt acatcttcaa gcagccgttc atgcggcccg tgcagacgac tcaggaagag   1080

gacggatgct cgtgcagatt ccctgaggag gaagaggggg gatgcgaact gcgcgtcaag   1140

ttctcacggt ccgccgacgc ccccgcatat caacagggcc agaatcagct ctacaacgag   1200

ctgaacctgg gaaggagaga ggagtacgac gtgctggaca agcgacgcgg acgcgacccg   1260

gagatggggg ggaaaccacg gcggaaaaac cctcaggaag gactgtacaa cgaactccag   1320

aaagacaaga tggcggaagc ctactcagaa atcgggatga agggagagcg gaggaggga   1380

aagggtcacg acgggctgta ccagggactg agcaccgcca ctaaggatac ctacgatgcc   1440

ttgcatatgc aagcactccc accccgg                                       1467
```

```
<210> SEQ ID NO 98
<211> LENGTH: 489
<212> TYPE: PRT
<213> ORGANISM: Artificial Sequence
<220> FEATURE:
<223> OTHER INFORMATION: LTG 2095 (hScFv aCD38 CD8 TM 4-1BB CD3 zeta)

<400> SEQUENCE: 98

Met Leu Leu Leu Val Thr Ser Leu Leu Leu Cys Glu Leu Pro His Pro
1               5                   10                  15

Ala Phe Leu Leu Ile Pro Gln Val Gln Leu Val Gln Ser Gly Ala Glu
            20                  25                  30

Val Lys Lys Pro Gly Ser Ser Val Lys Val Ser Cys Lys Ala Ser Gly
        35                  40                  45

Gly Thr Phe Ser Ser Tyr Ala Ile Ser Trp Val Arg Gln Ala Pro Gly
    50                  55                  60

Gln Gly Leu Glu Trp Met Gly Gly Ile Ile Pro Ile Phe Gly Thr Ala
65                  70                  75                  80

Asn His Ala Gln Lys Phe Gln Gly Arg Val Thr Ile Thr Ala Asp Glu
                85                  90                  95

Ser Thr Ser Thr Ala Tyr Met Glu Leu Ser Ser Leu Arg Ser Glu Asp
            100                 105                 110

Thr Ala Val Tyr Tyr Cys Ala Phe Met Met Val Pro Glu Tyr Tyr Phe
```

```
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Met
145                 150                 155                 160

Thr Gln Ser Pro Ser Ser Leu Ser Ala Ser Val Gly Asp Arg Val Thr
                165                 170                 175

Ile Thr Cys Arg Ala Ser Gln Gly Ile Arg Asn Asp Leu Gly Trp Tyr
            180                 185                 190

Gln Gln Lys Pro Gly Glu Ala Pro Lys Arg Leu Ile Tyr Ala Ala Ser
        195                 200                 205

Thr Leu Gln Asn Gly Val Pro Ser Arg Phe Ser Gly Ser Gly Ser Gly
    210                 215                 220

Thr Asp Phe Thr Leu Thr Ile Asn Ser Leu Gln Pro Glu Asp Phe Ala
225                 230                 235                 240

Thr Tyr Tyr Cys Gln Gln Tyr Asn Ser Tyr Pro Tyr Thr Phe Gly Gln
                245                 250                 255

Gly Thr Lys Leu Glu Ile Lys Ala Ala Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485
```

<210> SEQ ID NO 99
<211> LENGTH: 1476
<212> TYPE: DNA
<213> ORGANISM: Artificial Sequence
<220> FEATURE:
<223> OTHER INFORMATION: LTG 2096 (hScFv aCD38 CD8 TM 4-1BB CD3 zeta)

<400> SEQUENCE: 99

```
atgctgctgc tggtgaccag cctgctgctg tgcgaactgc cgcatccggc gtttctgctg     60
attccgaaag tgcaactcca agaaagcggc cccggacttg tcaaaccgtc ccagactctc    120
tccctgacct gtgccgtcag cggtggctca atttcgagcg gtggctacta ctggtcctgg    180
atcaggcagc atccgggaaa gggcttggag tggattggat acatctacta ctccgggtcc    240
acctactaca atccctcgct gaagtcgaga gtcaccatca gcgtggacac ctccaagaac    300
cagtttagcc tgaagctgtc ctcagtgacc gcagctgaca ccgccgtgta ctactgcgcc    360
cgcggcggag tgatgggcgg agacttcgac tactggggac agggaaccct ggtcactgtg    420
tccagcgggg gggggggatc cggcggcggc ggttccggtg gcggagggtc ccagtcagtg    480
ctgactcagc caccttccgt gtctgtgtcg cccggacaaa ccgccagcat cacgtgctcc    540
ggcgacaacc tcggtgatca ctatgtgtgc tggtaccaac agcggccggg gcagtcaccg    600
gtgctgatta tgtacgagga tactaagcgc ccttccggaa tccctgaccg gttctcggga    660
agcaactccg gaaacaccgc caccctgacc atctccggaa cccagacaat ggatgaagcg    720
gactactatt gcgtggcgtg ggacgattcg ctgtccggct gggtgttcgg cgggggaact    780
cagctgactg tgctcggagc ggccgcaact accacccctg cccctcggcc gccgactccg    840
gccccaacca tcgcaagcca acccctctcc ttgcgccccg aagcttgccg cccggccgcg    900
ggtggagccg tgcatacccg ggggctggac tttgcctgcg atatctacat ttgggccccg    960
ctggccggca cttgcggcgt gctcctgctg tcgctggtca tcacccttta ctgcaagagg   1020
ggccggaaga agctgcttta catcttcaag cagccgttca tgcggcccgt gcagacgact   1080
caggaagagg acggatgctc gtgcagattc cctgaggagg aagagggggg atgcgaactg   1140
cgcgtcaagt tctcacggtc cgccgacgcc cccgcatatc aacagggcca gaatcagctc   1200
tacaacgagc tgaacctggg aaggagagag gagtacgacg tgctggacaa gcgacgcgga   1260
cgcgacccgg agatgggggg gaaaccacgg cggaaaaacc ctcaggaagg actgtacaac   1320
gaactccaga aagacaagat ggcggaagcc tactcagaaa tcgggatgaa gggagagcgg   1380
aggaggggaa agggtcacga cgggctgtac cagggactga gcaccgccac taaggatacc   1440
tacgatgcct tgcatatgca agcactccca ccccgg                              1476
```

<210> SEQ ID NO 100
<211> LENGTH: 492
<212> TYPE: PRT
<213> ORGANISM: Artificial Sequence
<220> FEATURE:
<223> OTHER INFORMATION: LTG 2096 (hScFv aCD38 CD8 TM 4-1BB CD3 zeta)

<400> SEQUENCE: 100

```
Met Leu Leu Leu Val Thr Ser Leu Leu Leu Cys Glu Leu Pro His Pro
1               5                   10                  15

Ala Phe Leu Leu Ile Pro Lys Val Gln Leu Gln Glu Ser Gly Pro Gly
            20                  25                  30

Leu Val Lys Pro Ser Gln Thr Leu Ser Leu Thr Cys Ala Val Ser Gly
        35                  40                  45

Gly Ser Ile Ser Ser Gly Gly Tyr Tyr Trp Ser Trp Ile Arg Gln His
    50                  55                  60

Pro Gly Lys Gly Leu Glu Trp Ile Gly Tyr Ile Tyr Tyr Ser Gly Ser
65                  70                  75                  80

Thr Tyr Tyr Asn Pro Ser Leu Lys Ser Arg Val Thr Ile Ser Val Asp
                85                  90                  95
```

```
Thr Ser Lys Asn Gln Phe Ser Leu Lys Leu Ser Ser Val Thr Ala Ala
            100                 105                 110

Asp Thr Ala Val Tyr Tyr Cys Ala Arg Gly Gly Val Met Gly Gly Asp
        115                 120                 125

Phe Asp Tyr Trp Gly Gln Gly Thr Leu Val Thr Val Ser Ser Gly Gly
    130                 135                 140

Gly Gly Ser Gly Gly Gly Gly Ser Gly Gly Gly Gly Ser Gln Ser Val
145                 150                 155                 160

Leu Thr Gln Pro Pro Ser Val Ser Val Ser Pro Gly Gln Thr Ala Ser
                165                 170                 175

Ile Thr Cys Ser Gly Asp Asn Leu Gly Asp His Tyr Val Cys Trp Tyr
            180                 185                 190

Gln Gln Arg Pro Gly Gln Ser Pro Val Leu Ile Met Tyr Glu Asp Thr
        195                 200                 205

Lys Arg Pro Ser Gly Ile Pro Asp Arg Phe Ser Gly Ser Asn Ser Gly
    210                 215                 220

Asn Thr Ala Thr Leu Thr Ile Ser Gly Thr Gln Thr Met Asp Glu Ala
225                 230                 235                 240

Asp Tyr Tyr Cys Val Ala Trp Asp Asp Ser Leu Ser Gly Trp Val Phe
                245                 250                 255

Gly Gly Gly Thr Gln Leu Thr Val Leu Gly Ala Ala Ala Thr Thr Thr
            260                 265                 270

Pro Ala Pro Arg Pro Pro Thr Pro Ala Pro Thr Ile Ala Ser Gln Pro
        275                 280                 285

Leu Ser Leu Arg Pro Glu Ala Cys Arg Pro Ala Ala Gly Gly Ala Val
    290                 295                 300

His Thr Arg Gly Leu Asp Phe Ala Cys Asp Ile Tyr Ile Trp Ala Pro
305                 310                 315                 320

Leu Ala Gly Thr Cys Gly Val Leu Leu Leu Ser Leu Val Ile Thr Leu
                325                 330                 335

Tyr Cys Lys Arg Gly Arg Lys Lys Leu Leu Tyr Ile Phe Lys Gln Pro
            340                 345                 350

Phe Met Arg Pro Val Gln Thr Thr Gln Glu Glu Asp Gly Cys Ser Cys
        355                 360                 365

Arg Phe Pro Glu Glu Glu Glu Gly Gly Cys Glu Leu Arg Val Lys Phe
    370                 375                 380

Ser Arg Ser Ala Asp Ala Pro Ala Tyr Gln Gln Gly Gln Asn Gln Leu
385                 390                 395                 400

Tyr Asn Glu Leu Asn Leu Gly Arg Arg Glu Glu Tyr Asp Val Leu Asp
                405                 410                 415

Lys Arg Arg Gly Arg Asp Pro Glu Met Gly Gly Lys Pro Arg Arg Lys
            420                 425                 430

Asn Pro Gln Glu Gly Leu Tyr Asn Glu Leu Gln Lys Asp Lys Met Ala
        435                 440                 445

Glu Ala Tyr Ser Glu Ile Gly Met Lys Gly Glu Arg Arg Arg Gly Lys
    450                 455                 460

Gly His Asp Gly Leu Tyr Gln Gly Leu Ser Thr Ala Thr Lys Asp Thr
465                 470                 475                 480

Tyr Asp Ala Leu His Met Gln Ala Leu Pro Pro Arg
                485                 490
```

<210> SEQ ID NO 101
<211> LENGTH: 1500

<212> TYPE: DNA
<213> ORGANISM: Artificial Sequence
<220> FEATURE:
<223> OTHER INFORMATION: LTG 2097 (hScFv aCD38 CD8 TM 4-1BB CD3 zeta)

<400> SEQUENCE: 101

```
atgctgctgc tggtgaccag cctgctgctg tgcgaactgc cgcatccggc gtttctgctg     60
attccgcaac tccaactcca agaatctgga ccaggcctcg tgaagccctc ccaaactctg    120
tccctgacct gtaccgtgtc gggtggaagc atttcgagcg gtggatacta ctggtcctgg    180
atcaggcagc atcctggaaa gggactggag tggattgggt acatctacta ctccggctca    240
acctactaca acccgtcctt gaaatcgcgc gtgacgatct ccgtggacac ttcaaagaac    300
cagttcagcc tgaagctttc ctccgtgacc gcggccgata cagcggtgta ctactgcgct    360
cgggatcaga gcgtggccga ccctggtggc ggctactact actacggaat ggatgtctgg    420
ggacagggaa ccaccgtgac tgtgtccagc gggggcggcg gatccggggg gggggatcg    480
ggcggcggcg gttcgcagtc cgtgctgacc cagccaccta gcgtgtcagt ggcaccggga    540
cagaccgcct ccatttcctg cgggggaaat gacttcggta gccgctccgt gtcatggtat    600
caccagaagc cgggacaggc cccggtgctg gtcatctatg acgacaacga cagaccctcg    660
ggcatccccg aacggttttc gggaagcacc tccggagaca ctgccaccct gaccatctcc    720
cgggtcgagg tcggcgatga agccgattac tactgccaag tctgggacga cgactccgac    780
cactgggtgt tcggcggcgg aactaagctg actgtgctgg gggcggccgc aactaccacc    840
cctgcccctc ggccgccgac tccggcccca accatcgcaa gccaacccct ctccttgcgc    900
cccgaagctt gccgcccggc cgcgggtgga gccgtgcata cccgggggct ggactttgcc    960
tgcgatatct acatttgggc cccgctggcc ggcacttgcg gcgtgctcct gctgtcgctg   1020
gtcatcaccc tttactgcaa gaggggccgg aagaagctgc tttacatctt caagcagccg   1080
ttcatgcggc ccgtgcagac gactcaggaa gaggacggat gctcgtgcag attccctgag   1140
gaggaagagg ggggatgcga actgcgcgtc aagttctcac ggtccgccga cgcccccgca   1200
tatcaacagg gccagaatca gctctacaac gagctgaacc tgggaaggag agaggagtac   1260
gacgtgctgg acaagcgacg cggacgcgac ccggagatgg gggggaaacc acggcggaaa   1320
aaccctcagg aaggactgta caacgaactc cagaaagaca agatggcgga agcctactca   1380
gaaatcggga tgaagggaga gcggaggagg ggaaagggtc acgacgggct gtaccaggga   1440
ctgagcaccg ccactaagga tacctacgat gccttgcata tgcaagcact cccaccccgg   1500
```

<210> SEQ ID NO 102
<211> LENGTH: 500
<212> TYPE: PRT
<213> ORGANISM: Artificial Sequence
<220> FEATURE:
<223> OTHER INFORMATION: LTG 2097 (hScFv aCD38 CD8 TM 4-1BB CD3 zeta)

<400> SEQUENCE: 102

```
Met Leu Leu Leu Val Thr Ser Leu Leu Leu Cys Glu Leu Pro His Pro
1               5                   10                  15

Ala Phe Leu Leu Ile Pro Gln Leu Gln Leu Gln Glu Ser Gly Pro Gly
            20                  25                  30

Leu Val Lys Pro Ser Gln Thr Leu Ser Leu Thr Cys Thr Val Ser Gly
        35                  40                  45

Gly Ser Ile Ser Ser Gly Gly Tyr Tyr Trp Ser Trp Ile Arg Gln His
    50                  55                  60
```

```
Pro Gly Lys Gly Leu Glu Trp Ile Gly Tyr Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Asp Gln Ser Val Ala Asp Pro
        115                 120                 125

Gly Gly Gly Tyr Tyr Tyr Tyr Gly Met Asp Val Trp Gly Gln Gly Thr
    130                 135                 140

Thr Val Thr Val Ser Ser Gly Gly Gly Gly Ser Gly Gly Gly Gly Ser
145                 150                 155                 160

Gly Gly Gly Gly Ser Gln Ser Val Leu Thr Gln Pro Pro Ser Val Ser
                165                 170                 175

Val Ala Pro Gly Gln Thr Ala Ser Ile Ser Cys Gly Gly Asn Asp Phe
            180                 185                 190

Gly Ser Arg Ser Val Ser Trp Tyr His Gln Lys Pro Gly Gln Ala Pro
        195                 200                 205

Val Leu Val Ile Tyr Asp Asp Asn Asp Arg Pro Ser Gly Ile Pro Glu
    210                 215                 220

Arg Phe Ser Gly Ser Thr Ser Gly Asp Thr Ala Thr Leu Thr Ile Ser
225                 230                 235                 240

Arg Val Glu Val Gly Asp Glu Ala Asp Tyr Tyr Cys Gln Val Trp Asp
                245                 250                 255

Asp Asp Ser Asp His Trp Val Phe Gly Gly Gly Thr Lys Leu Thr Val
            260                 265                 270

Leu Gly Ala Ala Ala Thr Thr Thr Pro Ala Pro Arg Pro Pro Thr Pro
        275                 280                 285

Ala Pro Thr Ile Ala Ser Gln Pro Leu Ser Leu Arg Pro Glu Ala Cys
    290                 295                 300

Arg Pro Ala Ala Gly Gly Ala Val His Thr Arg Gly Leu Asp Phe Ala
305                 310                 315                 320

Cys Asp Ile Tyr Ile Trp Ala Pro Leu Ala Gly Thr Cys Gly Val Leu
                325                 330                 335

Leu Leu Ser Leu Val Ile Thr Leu Tyr Cys Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
```

```
                485                 490                 495

Leu Pro Pro Arg
            500


<210> SEQ ID NO 103
<211> LENGTH: 1491
<212> TYPE: DNA
<213> ORGANISM: Artificial Sequence
<220> FEATURE:
<223> OTHER INFORMATION: LTG 2098 (hScFv aCD38 CD8 TM 4-1BB CD3 zeta)

<400> SEQUENCE: 103

atgctgctgc tggtgaccag cctgctgctg tgcgaactgc cgcatccggc gtttctgctg      60

attccgcaag tgcaactcca acaatcgggc cccggactcg tgaaaccgtc ccagactctg     120

tcccttactt gcgtgatttc cggggactcc gtgagctcaa actcggcggc ctggaactgg     180

attagacagt ccccttcccg gggtctggaa tggctgggcc ggacttacta ccggtcgaag     240

tggcacaacg attacgcagt cagcgtcgag agccgcatca tcgtgaaccc ggacacctca     300

aagaaccagt tcagcctgca actgaattcc gtgacccccg aggacaccgc tgtgtactac     360

tgcgcccgcg accccggata cttctatgga ctggacgtct ggggacaggg gaccatggtc     420

accgtgtcga gcggcggcgg cggatccggt ggcgggggat ccggcggtgg cggatccaac     480

ttcatgttga ctcagccgca ttcggtgtcg gagtcccctg gaaagacagt caccatccca     540

tgtacccgga gcagcggaac tatcgccgac tactacgtgc agtggtacca gcagcgccct     600

gattcctcac cgatcattgt gatctatgac gacaaccaga ggccctccgg ggtgccggat     660

agattcagcg gatccattga ctcctcgtcc aactctgcct cactgacgat ctccgggctc     720

aagaccgaag atgaagcggc ctactactgc cagtcatacg actccaccaa ccactgggtg     780

tttggtggcg gaactaagct gaccgtgctg ggagcggccg caactaccac ccctgcccct     840

cggccgccga ctccggcccc aaccatcgca agccaacccc tctccttgcg ccccgaagct     900

tgccgcccgg ccgcgggtgg agccgtgcat acccgggggc tggactttgc ctgcgatatc     960

tacatttggg ccccgctggc cggcacttgc ggcgtgctcc tgctgtcgct ggtcatcacc    1020

ctttactgca agaggggccg gaagaagctg ctttacatct tcaagcagcc gttcatgcgg    1080

cccgtgcaga cgactcagga agaggacgga tgctcgtgca gattccctga ggaggaagag    1140

gggggatgcg aactgcgcgt caagttctca cggtccgccg acgcccccgc atatcaacag    1200

ggccagaatc agctctacaa cgagctgaac ctgggaagga gagaggagta cgacgtgctg    1260

gacaagcgac gcggacgcga cccggagatg ggggggaaac cacggcggaa aaaccctcag    1320

gaaggactgt acaacgaact ccagaaagac aagatggcgg aagcctactc agaaatcggg    1380

atgaagggag agcggaggag gggaaagggt cacgacgggc tgtaccaggg actgagcacc    1440

gccactaagg atacctacga tgccttgcat atgcaagcac tcccaccccg g             1491


<210> SEQ ID NO 104
<211> LENGTH: 497
<212> TYPE: PRT
<213> ORGANISM: Artificial Sequence
<220> FEATURE:
<223> OTHER INFORMATION: LTG 2098 (hScFv aCD38 CD8 TM 4-1BB CD3 zeta)

<400> SEQUENCE: 104

Met Leu Leu Leu Val Thr Ser Leu Leu Leu Cys Glu Leu Pro His Pro
1               5                   10                  15

Ala Phe Leu Leu Ile Pro Gln Val Gln Leu Gln Gln Ser Gly Pro Gly
```

```
            20                  25                  30

Leu Val Lys Pro Ser Gln Thr Leu Ser Leu Thr Cys Val Ile Ser Gly
        35                  40                  45

Asp Ser Val Ser Ser Asn Ser Ala Ala Trp Asn Trp Ile Arg Gln Ser
    50                  55                  60

Pro Ser Arg Gly Leu Glu Trp Leu Gly Arg Thr Tyr Tyr Arg Ser Lys
65                  70                  75                  80

Trp His Asn Asp Tyr Ala Val Ser Val Glu Ser Arg Ile Ile Val Asn
                85                  90                  95

Pro Asp Thr Ser Lys Asn Gln Phe Ser Leu Gln Leu Asn Ser Val Thr
            100                 105                 110

Pro Glu Asp Thr Ala Val Tyr Tyr Cys Ala Arg Asp Pro Gly Tyr Phe
        115                 120                 125

Tyr Gly Leu Asp Val Trp Gly Gln Gly Thr Met Val Thr Val Ser Ser
    130                 135                 140

Gly Gly Gly Gly Ser Gly Gly Gly Gly Ser Gly Gly Gly Gly Ser Asn
145                 150                 155                 160

Phe Met Leu Thr Gln Pro His Ser Val Ser Glu Ser Pro Gly Lys Thr
                165                 170                 175

Val Thr Ile Pro Cys Thr Arg Ser Ser Gly Thr Ile Ala Asp Tyr Tyr
            180                 185                 190

Val Gln Trp Tyr Gln Gln Arg Pro Asp Ser Ser Pro Ile Ile Val Ile
        195                 200                 205

Tyr Asp Asp Asn Gln Arg Pro Ser Gly Val Pro Asp Arg Phe Ser Gly
    210                 215                 220

Ser Ile Asp Ser Ser Ser Asn Ser Ala Ser Leu Thr Ile Ser Gly Leu
225                 230                 235                 240

Lys Thr Glu Asp Glu Ala Ala Tyr Tyr Cys Gln Ser Tyr Asp Ser Thr
                245                 250                 255

Asn His Trp Val Phe Gly Gly Gly Thr Lys Leu Thr Val Leu Gly Ala
            260                 265                 270

Ala Ala Thr Thr Thr Pro Ala Pro Arg Pro Pro Thr Pro Ala Pro Thr
        275                 280                 285

Ile Ala Ser Gln Pro Leu Ser Leu Arg Pro Glu Ala Cys Arg Pro Ala
    290                 295                 300

Ala Gly Gly Ala Val His Thr Arg Gly Leu Asp Phe Ala Cys Asp Ile
305                 310                 315                 320

Tyr Ile Trp Ala Pro Leu Ala Gly Thr Cys Gly Val Leu Leu Leu Ser
                325                 330                 335

Leu Val Ile Thr Leu Tyr Cys Lys Arg Gly Arg Lys Lys Leu Leu Tyr
            340                 345                 350

Ile Phe Lys Gln Pro Phe Met Arg Pro Val Gln Thr Thr Gln Glu Glu
        355                 360                 365

Asp Gly Cys Ser Cys Arg Phe Pro Glu Glu Glu Glu Gly Gly Cys Glu
    370                 375                 380

Leu Arg Val Lys Phe Ser Arg Ser Ala Asp Ala Pro Ala Tyr Gln Gln
385                 390                 395                 400

Gly Gln Asn Gln Leu Tyr Asn Glu Leu Asn Leu Gly Arg Arg Glu Glu
                405                 410                 415

Tyr Asp Val Leu Asp Lys Arg Arg Gly Arg Asp Pro Glu Met Gly Gly
            420                 425                 430

Lys Pro Arg Arg Lys Asn Pro Gln Glu Gly Leu Tyr Asn Glu Leu Gln
        435                 440                 445
```

```
Lys Asp Lys Met Ala Glu Ala Tyr Ser Glu Ile Gly Met Lys Gly Glu
    450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg


<210> SEQ ID NO 105
<211> LENGTH: 1467
<212> TYPE: DNA
<213> ORGANISM: Artificial Sequence
<220> FEATURE:
<223> OTHER INFORMATION: LTG 2099 (hScFv aCD38 CD8 TM 4-1BB CD3 zeta)

<400> SEQUENCE: 105

atgctgctgc tggtgaccag cctgctgctg tgcgaactgc cgcatccggc gtttctgctg     60

attccgcaag tcacactcaa agaatccgga ccggtgctcg tgaagcctac tgaaaccttg    120

accctgacat gcaccttttc cgggttctcc ctgagcacct cgggagtcgg agtggcgtgg    180

attaggcagc cgccaggaaa agacctcgag tggctcgccc ttatctactg ggacgatgac    240

aagcgctact caccctcact ggagagcaga ctgacgatca ccaaggatac ctcgaagaac    300

caagtggccc tgactatgtc cgacatggac cctgtggaca ccgcgactta ctactgcgcc    360

cggggcgatt actggggacg gctggactac tggggacagg gaactctggt caccgtgtcc    420

agcggcggcg gtggttcagg gggtggcggc agcggggggg gcggatcgga tatccagctt    480

acccagtcgc cgtcctccct ctctgcatcg attggcgacc gcgtgactat tacgtgtcag    540

gcctccgagg acatcaacaa ctacctgaac tggtaccagc agaagcccgg aaaggcccca    600

aagctgctga tctacgacgc tagcaacttg gaaaccggag tgccgtcccg gttctccgga    660

tccgggagcg gtaccgactt caccttcacc atcaactccc tgcaacccga ggatattgcc    720

acctattact gccaacagtt cgacaatatg cctctgactt tcgggggcgg cactaagctc    780

gaaatcaagg cggccgcaac taccacccct gcccctcggc cgccgactcc ggccccaacc    840

atcgcaagcc aacccctctc cttgcgcccc gaagcttgcc gcccggccgc gggtggagcc    900

gtgcataccc gggggctgga ctttgcctgc gatatctaca tttgggcccc gctggccggc    960

acttgcggcg tgctcctgct gtcgctggtc atcacccttt actgcaagag gggccggaag   1020

aagctgcttt acatcttcaa gcagccgttc atgcggcccg tgcagacgac tcaggaagag   1080

gacggatgct cgtgcagatt ccctgaggag gaagaggggg gatgcgaact gcgcgtcaag   1140

ttctcacggt ccgccgacgc ccccgcatat caacagggcc agaatcagct ctacaacgag   1200

ctgaacctgg gaaggagaga ggagtacgac gtgctggaca agcgacgcgg acgcgacccg   1260

gagatggggg ggaaaccacg gcggaaaaac cctcaggaag gactgtacaa cgaactccag   1320

aaagacaaga tggcggaagc ctactcagaa atcgggatga agggagagcg gaggaggga   1380

aagggtcacg acgggctgta ccagggactg agcaccgcca ctaaggatac ctacgatgcc   1440

ttgcatatgc aagcactccc accccgg                                        1467


<210> SEQ ID NO 106
<211> LENGTH: 489
<212> TYPE: PRT
<213> ORGANISM: Artificial Sequence
<220> FEATURE:
<223> OTHER INFORMATION: LTG 2099 (hScFv aCD38 CD8 TM 4-1BB CD3 zeta)
```

<400> SEQUENCE: 106

```
Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Val
            20                  25                  30

Leu Val Lys Pro Thr Glu Thr Leu Thr Leu Thr Cys Thr Phe Ser Gly
        35                  40                  45

Phe Ser Leu Ser Thr Ser Gly Val Gly Val Ala Trp Ile Arg Gln Pro
    50                  55                  60

Pro Gly Lys Asp Leu Glu Trp Leu Ala Leu Ile Tyr Trp Asp Asp Asp
65                  70                  75                  80

Lys Arg Tyr Ser Pro Ser Leu Glu Ser Arg Leu Thr Ile Thr Lys Asp
                85                  90                  95

Thr Ser Lys Asn Gln Val Ala Leu Thr Met Ser Asp Met Asp Pro Val
            100                 105                 110

Asp Thr Ala Thr Tyr Tyr Cys Ala Arg Gly Asp Tyr Trp Gly Arg Leu
        115                 120                 125

Asp Tyr Trp Gly Gln Gly Thr Leu Val Thr Val Ser Ser Gly Gly Gly
    130                 135                 140

Gly Ser Gly Gly Gly Gly Ser Gly Gly Gly Gly Ser Asp Ile Gln Leu
145                 150                 155                 160

Thr Gln Ser Pro Ser Ser Leu Ser Ala Ser Ile Gly Asp Arg Val Thr
                165                 170                 175

Ile Thr Cys Gln Ala Ser Glu Asp Ile Asn Asn Tyr Leu Asn Trp Tyr
            180                 185                 190

Gln Gln Lys Pro Gly Lys Ala Pro Lys Leu Leu Ile Tyr Asp Ala Ser
        195                 200                 205

Asn Leu Glu Thr Gly Val Pro Ser Arg Phe Ser Gly Ser Gly Ser Gly
    210                 215                 220

Thr Asp Phe Thr Phe Thr Ile Asn Ser Leu Gln Pro Glu Asp Ile Ala
225                 230                 235                 240

Thr Tyr Tyr Cys Gln Gln Phe Asp Asn Met Pro Leu Thr Phe Gly Gly
                245                 250                 255

Gly Thr Lys Leu Glu Ile Lys Ala Ala Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380

Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
```

```
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485


<210> SEQ ID NO 107
<211> LENGTH: 1467
<212> TYPE: DNA
<213> ORGANISM: Artificial Sequence
<220> FEATURE:
<223> OTHER INFORMATION: LTG 2501 (hScFv aCD38 CD8 TM 4-1BB CD3 zeta)

<400> SEQUENCE: 107

atgctgctgc tggtgaccag cctgctgctg tgcgaactgc cgcatccggc gtttctgctg     60

attccgcaag tcactctgaa agaatccggt cccgtgctcg tcaaacccac cgaaaccctg    120

accctgacct gtactttctc cggattttcc ctctcaacct ccggcgtggg cgtggcctgg    180

attcggcagc ctcccggaaa ggatttggag tggctggccc tgatctactg ggatgacgat    240

aagcgctact ccccatccct cgagtcccgg ctgactatca ctaaggacac ctccaagaat    300

caagtcgccc ttactatgtc ggacatggac cctgtggaca ccgctacgta ctactgcgct    360

cggggagact attgggggcg cctggactac tggggacagg gaaccctcgt gaccgtgtcg    420

tctgggggcg gcggaccggg tggcggagcg tccgggggcg gtggatcgga catccagctg    480

acacagagcc ccagcagcct gagcgcctcg attggcgaca gagtgaccat tacgtgccag    540

gcatccgagg acatcaacaa ctacctgaac tggtaccagc agaagcctgg gaaggcccca    600

aagctgctga tctacgacgc ctccaacctg gaaaccggag tgccgtcaag gttcagcggc    660

tcgggatcag gaaccgattt cactttcacc atcaacagct tgcagccgga agatatcgcg    720

acctactact gccaacagtt cgacaacatg ccgctgactt tcggtggcgg gaccaagctt    780

gagattaagg cggccgcaac taccacccct gcccctcggc cgccgactcc ggccccaacc    840

atcgcaagcc aacccctctc cttgcgcccc gaagcttgcc gcccggccgc gggtggagcc    900

gtgcataccc gggggctgga ctttgcctgc gatatctaca tttgggcccc gctggccggc    960

acttgcggcg tgctcctgct gtcgctggtc atcacccttt actgcaagag gggccggaag   1020

aagctgcttt acatcttcaa gcagccgttc atgcggcccg tgcagacgac tcaggaagag   1080

gacggatgct cgtgcagatt ccctgaggag gaagaggggg gatgcgaact gcgcgtcaag   1140

ttctcacggt ccgccgacgc ccccgcatat caacagggcc agaatcagct ctacaacgag   1200

ctgaacctgg gaaggagaga ggagtacgac gtgctggaca agcgacgcgg acgcgacccg   1260

gagatggggg ggaaaccacg gcggaaaaac cctcaggaag gactgtacaa cgaactccag   1320

aaagacaaga tggcggaagc ctactcagaa atcgggatga agggagagcg gaggagggga   1380

aagggtcacg acgggctgta ccagggactg agcaccgcca ctaaggatac ctacgatgcc   1440

ttgcatatgc aagcactccc accccgg                                        1467


<210> SEQ ID NO 108
```

```
<211> LENGTH: 489
<212> TYPE: PRT
<213> ORGANISM: Artificial Sequence
<220> FEATURE:
<223> OTHER INFORMATION: LTG 2501 (hScFv aCD38 CD8 TM 4-1BB CD3 zeta)

<400> SEQUENCE: 108

Met Leu Leu Leu Val Thr Ser Leu Leu Leu Cys Glu Leu Pro His Pro
1               5                   10                  15

Ala Phe Leu Leu Ile Pro Gln Val Thr Leu Lys Glu Ser Gly Pro Val
            20                  25                  30

Leu Val Lys Pro Thr Glu Thr Leu Thr Leu Thr Cys Thr Phe Ser Gly
        35                  40                  45

Phe Ser Leu Ser Thr Ser Gly Val Gly Val Ala Trp Ile Arg Gln Pro
    50                  55                  60

Pro Gly Lys Asp Leu Glu Trp Leu Ala Leu Ile Tyr Trp Asp Asp Asp
65                  70                  75                  80

Lys Arg Tyr Ser Pro Ser Leu Glu Ser Arg Leu Thr Ile Thr Lys Asp
                85                  90                  95

Thr Ser Lys Asn Gln Val Ala Leu Thr Met Ser Asp Met Asp Pro Val
            100                 105                 110

Asp Thr Ala Thr Tyr Tyr Cys Ala Arg Gly Asp Tyr Trp Gly Arg Leu
        115                 120                 125

Asp Tyr Trp Gly Gln Gly Thr Leu Val Thr Val Ser Ser Gly Gly Gly
    130                 135                 140

Gly Pro Gly Gly Gly Ala Ser Gly Gly Gly Gly Ser Asp Ile Gln Leu
145                 150                 155                 160

Thr Gln Ser Pro Ser Ser Leu Ser Ala Ser Ile Gly Asp Arg Val Thr
                165                 170                 175

Ile Thr Cys Gln Ala Ser Glu Asp Ile Asn Asn Tyr Leu Asn Trp Tyr
            180                 185                 190

Gln Gln Lys Pro Gly Lys Ala Pro Lys Leu Leu Ile Tyr Asp Ala Ser
        195                 200                 205

Asn Leu Glu Thr Gly Val Pro Ser Arg Phe Ser Gly Ser Gly Ser Gly
    210                 215                 220

Thr Asp Phe Thr Phe Thr Ile Asn Ser Leu Gln Pro Glu Asp Ile Ala
225                 230                 235                 240

Thr Tyr Tyr Cys Gln Gln Phe Asp Asn Met Pro Leu Thr Phe Gly Gly
                245                 250                 255

Gly Thr Lys Leu Glu Ile Lys Ala Ala Ala Thr Thr Thr Pro Ala Pro
            260                 265                 270

Arg Pro Pro Thr Pro Ala Pro Thr Ile Ala Ser Gln Pro Leu Ser Leu
        275                 280                 285

Arg Pro Glu Ala Cys Arg Pro Ala Ala Gly Gly Ala Val His Thr Arg
    290                 295                 300

Gly Leu Asp Phe Ala Cys Asp Ile Tyr Ile Trp Ala Pro Leu Ala Gly
305                 310                 315                 320

Thr Cys Gly Val Leu Leu Leu Ser Leu Val Ile Thr Leu Tyr Cys Lys
                325                 330                 335

Arg Gly Arg Lys Lys Leu Leu Tyr Ile Phe Lys Gln Pro Phe Met Arg
            340                 345                 350

Pro Val Gln Thr Thr Gln Glu Glu Asp Gly Cys Ser Cys Arg Phe Pro
        355                 360                 365

Glu Glu Glu Glu Gly Gly Cys Glu Leu Arg Val Lys Phe Ser Arg Ser
    370                 375                 380
```

```
Ala Asp Ala Pro Ala Tyr Gln Gln Gly Gln Asn Gln Leu Tyr Asn Glu
385                 390                 395                 400

Leu Asn Leu Gly Arg Arg Glu Glu Tyr Asp Val Leu Asp Lys Arg Arg
                405                 410                 415

Gly Arg Asp Pro Glu Met Gly Gly Lys Pro Arg Arg Lys Asn Pro Gln
            420                 425                 430

Glu Gly Leu Tyr Asn Glu Leu Gln Lys Asp Lys Met Ala Glu Ala Tyr
        435                 440                 445

Ser Glu Ile Gly Met Lys Gly Glu Arg Arg Arg Gly Lys Gly His Asp
    450                 455                 460

Gly Leu Tyr Gln Gly Leu Ser Thr Ala Thr Lys Asp Thr Tyr Asp Ala
465                 470                 475                 480

Leu His Met Gln Ala Leu Pro Pro Arg
                485


<210> SEQ ID NO 109
<211> LENGTH: 1479
<212> TYPE: DNA
<213> ORGANISM: Artificial Sequence
<220> FEATURE:
<223> OTHER INFORMATION: LTG 2502 (hScFv aCD38 CD8 TM 4-1BB CD3 zeta)

<400> SEQUENCE: 109

atgctgctgc tggtgaccag cctgctgctg tgcgaactgc cgcatccggc gtttctgctg     60

attccgcaag tgcaactcca agaatccggt cctggcctcg tcaaaccttc cgaaacactg    120

tccctgacct gtaccgtgtc cggagggtcg attagctcgt cgtcatacta ctggggatgg    180

atcagacagc cgccgggaaa gggactcgag tggatcgggt ccatctacta ctcgggtagc    240

acttactaca acccgtcgct gaagtcccgc gtgactattt ccgtggacac ctccaagaac    300

cagttcagcc tgaagctgag ctccgtgacc gctgccgata ccgcagtgta ctactgcgcg    360

cgccggggaa gcatccgcgc ctttgacatc tggggacagg gaactatggt cacggtgtcc    420

agcggcggtg gcggatctgg cggcggcgga tccggggggg ggggaagcca gtcagtgctg    480

actcagccgc cttcggtgtc cgaggcgccc ggccagaggg tcaccatttc ctgctctgga    540

tcgtccagca acattggcaa caacgccgtc aactggtacc agcagctgcc cggggaagcc    600

cccaagctgt tgatctacta cgacgagtat ctgccaagcg gagtgtcaga cagattctcc    660

gcgtcgaagt ccggcacctc cgcctcactt gcaatctccg gcctgcggtc cgaggacgaa    720

gccgattact attgcgccgc ctgggacgat aatctgtccg gttgggtgtt cggcggtgga    780

acccagctta ccgtgctcgg agcggccgca actaccaccc ctgcccctcg gccgccgact    840

ccggccccaa ccatcgcaag ccaacccctc tccttgcgcc ccgaagcttg ccgcccggcc    900

gcgggtggag ccgtgcatac ccgggggctg gactttgcct gcgatatcta catttgggcc    960

ccgctggccg gcacttgcgg cgtgctcctg ctgtcgctgg tcatcaccct ttactgcaag   1020

aggggccgga agaagctgct ttacatcttc aagcagccgt tcatgcggcc cgtgcagacg   1080

actcaggaag aggacggatg ctcgtgcaga ttccctgagg aggaagaggg gggatgcgaa   1140

ctgcgcgtca agttctcacg gtccgccgac gcccccgcat atcaacaggg ccagaatcag   1200

ctctacaacg agctgaacct gggaaggaga gaggagtacg acgtgctgga caagcgacgc   1260

ggacgcgacc cggagatggg ggggaaacca cggcggaaaa accctcagga aggactgtac   1320

aacgaactcc agaaagacaa gatggcggaa gcctactcag aaatcgggat gaagggagag   1380

cggaggaggg gaaagggtca cgacgggctg taccagggac tgagcaccgc cactaaggat   1440
```

acctacgatg ccttgcatat gcaagcactc ccacccccgg 1479

<210> SEQ ID NO 110
<211> LENGTH: 493
<212> TYPE: PRT
<213> ORGANISM: Artificial Sequence
<220> FEATURE:
<223> OTHER INFORMATION: LTG 2502 (hScFv aCD38 CD8 TM 4-1BB CD3 zeta)

<400> SEQUENCE: 110

```
Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Gly Ser Ile Ser Ser Ser Ser Tyr Tyr Trp Gly Trp Ile Arg Gln Pro
    50                  55                  60

Pro Gly Lys Gly Leu Glu Trp Ile Gly Ser Ile Tyr Tyr Ser Gly Ser
65                  70                  75                  80

Thr Tyr Tyr Asn Pro Ser Leu Lys Ser Arg Val Thr Ile Ser Val Asp
                85                  90                  95

Thr Ser Lys Asn Gln Phe Ser Leu Lys Leu Ser Ser Val Thr Ala Ala
            100                 105                 110

Asp Thr Ala Val Tyr Tyr Cys Ala Arg Arg Gly Ser Ile Arg Ala Phe
        115                 120                 125

Asp Ile Trp Gly Gln Gly Thr Met Val Thr Val Ser Ser Gly Gly Gly
    130                 135                 140

Gly Ser Gly Gly Gly Gly Ser Gly Gly Gly Gly Ser Gln Ser Val Leu
145                 150                 155                 160

Thr Gln Pro Pro Ser Val Ser Glu Ala Pro Gly Gln Arg Val Thr Ile
                165                 170                 175

Ser Cys Ser Gly Ser Ser Ser Asn Ile Gly Asn Asn Ala Val Asn Trp
            180                 185                 190

Tyr Gln Gln Leu Pro Gly Glu Ala Pro Lys Leu Leu Ile Tyr Tyr Asp
        195                 200                 205

Glu Tyr Leu Pro Ser Gly Val Ser Asp Arg Phe Ser Ala Ser Lys Ser
    210                 215                 220

Gly Thr Ser Ala Ser Leu Ala Ile Ser Gly Leu Arg Ser Glu Asp Glu
225                 230                 235                 240

Ala Asp Tyr Tyr Cys Ala Ala Trp Asp Asp Asn Leu Ser Gly Trp Val
                245                 250                 255

Phe Gly Gly Gly Thr Gln Leu Thr Val Leu Gly Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350
```

```
Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 111
<211> LENGTH: 1479
<212> TYPE: DNA
<213> ORGANISM: Artificial Sequence
<220> FEATURE:
<223> OTHER INFORMATION: LTG 2503 (hScFv aCD38 CD8 TM 4-1BB CD3 zeta)

<400> SEQUENCE: 111

```
atgctgctgc tggtgaccag cctgctgctg tgcgaactgc cgcatccggc gtttctgctg     60

attccgcaag tgcaactcca agaatccggt cctggtctgg tcaaaccctc cgaaactctg    120

tccctgacgt gcaccgtgtc gggatactcc atttcctccg gatactactg gggttggatc    180

cgccagcctc cgggaaaagg cctggaatgg gtcggaacca tcgggaagga cggatccact    240

ttctattccc cgtcgctgaa gtcacggatc accattagcc aggacacctc caagaaccag    300

ttcagcctga agctgaactc cgtgaacgcc gcggacactg ccgtctacta ctgtgcgaag    360

cacaagtggt ccttcgactc cgggaacgat tacttcgacc actggggcca ggggaccctc    420

gtgaccgtgt cgtccggcgg cgggggatcc ggtggcgggg gaagcggcgg cggcggatca    480

gacattcagc tgacccagtc tccctcatcc ctgtcggcta gcgtgggcga tagagtgacc    540

atcacatgcc aggcatcgca ggacatttcg aactatctga actggtacca gcagaagcct    600

ggaaaggccc cgaagctttt gatctacgac gccagcaacc tggagactgg agtgcccagc    660

cggttcagcg gatcgggatc cggtaccgat ttcaccttta ccatctcctc actgcaacca    720

gaggatatcg ccacctacta ctgccagcag taccagaatc tcccgctcac tttcggacaa    780

gggactaggc ttgagatcaa ggcggccgca actaccaccc ctgcccctcg gccgccgact    840

ccggccccaa ccatcgcaag ccaacccctc tccttgcgcc ccgaagcttg ccgcccggcc    900

gcgggtggag ccgtgcatac ccgggggctg gactttgcct gcgatatcta catttgggcc    960

ccgctggccg gcacttgcgg cgtgctcctg ctgtcgctgg tcatcaccct ttactgcaag   1020

aggggccgga agaagctgct ttacatcttc aagcagccgt tcatgcggcc cgtgcagacg   1080

actcaggaag aggacggatg ctcgtgcaga ttccctgagg aggaagaggg ggatgcgaa    1140

ctgcgcgtca agttctcacg gtccgccgac gcccccgcat atcaacaggg ccagaatcag   1200

ctctacaacg agctgaacct gggaaggaga gaggagtacg acgtgctgga caagcgacgc   1260
```

```
ggacgcgacc cggagatggg ggggaaacca cggcggaaaa accctcagga aggactgtac   1320

aacgaactcc agaaagacaa gatggcggaa gcctactcag aaatcgggat gaagggagag   1380

cggaggaggg gaaagggtca cgacgggctg taccagggac tgagcaccgc cactaaggat   1440

acctacgatg ccttgcatat gcaagcactc ccaccccgg                          1479
```

```
<210> SEQ ID NO 112
<211> LENGTH: 493
<212> TYPE: PRT
<213> ORGANISM: Artificial Sequence
<220> FEATURE:
<223> OTHER INFORMATION: LTG 2503 (hScFv aCD38 CD8 TM 4-1BB CD3 zeta)

<400> SEQUENCE: 112

Met Leu Leu Leu Val Thr Ser Leu Leu Leu Cys Glu Leu Pro His Pro
1               5                   10                  15

Ala Phe Leu Leu Ile Pro Gln Val Gln Leu Gln Glu Ser Gly Pro Gly
            20                  25                  30

Leu Val Lys Pro Ser Glu Thr Leu Ser Leu Thr Cys Thr Val Ser Gly
        35                  40                  45

Tyr Ser Ile Ser Ser Gly Tyr Tyr Trp Gly Trp Ile Arg Gln Pro Pro
    50                  55                  60

Gly Lys Gly Leu Glu Trp Val Gly Thr Ile Gly Lys Asp Gly Ser Thr
65                  70                  75                  80

Phe Tyr Ser Pro Ser Leu Lys Ser Arg Ile Thr Ile Ser Gln Asp Thr
                85                  90                  95

Ser Lys Asn Gln Phe Ser Leu Lys Leu Asn Ser Val Asn Ala Ala Asp
            100                 105                 110

Thr Ala Val Tyr Tyr Cys Ala Lys His Lys Trp Ser Phe Asp Ser Gly
        115                 120                 125

Asn Asp Tyr Phe Asp His Trp Gly Gln Gly Thr Leu Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Leu Thr Gln Ser Pro Ser Ser Leu Ser Ala Ser Val Gly
                165                 170                 175

Asp Arg Val Thr Ile Thr Cys Gln Ala Ser Gln Asp Ile Ser Asn Tyr
            180                 185                 190

Leu Asn Trp Tyr Gln Gln Lys Pro Gly Lys Ala Pro Lys Leu Leu Ile
        195                 200                 205

Tyr Asp Ala Ser Asn Leu Glu Thr Gly Val Pro Ser Arg Phe Ser Gly
    210                 215                 220

Ser Gly Ser Gly Thr Asp Phe Thr Phe Thr Ile Ser Ser Leu Gln Pro
225                 230                 235                 240

Glu Asp Ile Ala Thr Tyr Tyr Cys Gln Gln Tyr Gln Asn Leu Pro Leu
                245                 250                 255

Thr Phe Gly Gln Gly Thr Arg Leu Glu Ile Lys Ala Ala Ala Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
```

```
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490
```

<210> SEQ ID NO 113
<211> LENGTH: 1482
<212> TYPE: DNA
<213> ORGANISM: Artificial Sequence
<220> FEATURE:
<223> OTHER INFORMATION: LTG 2525 (hScFv aCD38 CD8 TM 4-1BB CD3 zeta)

<400> SEQUENCE: 113

```
atgctgctgc tggtgaccag cctgctgctg tgcgaactgc cgcatccggc gtttctgctg      60

attccggagg tacagttgct ggagagtgga ggtggtctgg tacagccggg agggtccttg     120

cggctgtcat gcgcagttag cggatttact ttcaactcct tcgccatgtc ctgggttagg     180

caggcccctg gaaagggtct cgaatgggtc tctgccatca gtgggagtgg aggtggcact     240

tactatgctg acagcgtcaa agggcgcttc actattagtc gagacaactc aaagaatact     300

ctgtaccttc aaatgaactc cctccgagcc gaagacactg ccgtatactt ttgtgctaaa     360

gacaaaatcc tctggttcgg cgagcctgtg ttcgactact ggggacaggg tacgctcgtg     420

accgtgtcat ctgctagcgg tggtggcggc tcaggtggtg gtggctctgg tggaggtggt     480

agtgagatag tactgacaca gagcccggca actctttctc tctcacctgg tgaaagagca     540

accctcagtt gcagggcttc ccagtccgta tcttcttatc tcgcctggta ccaacagaaa     600

ccggggcaag caccacgact cttgatctat gatgcctcta accgcgcaac agggattccg     660

gcccgattta gcggcagcgg tagcggcacg gactttacac tgacgatttc ttcccttgag     720

ccggaagact ttgctgtgta ttattgtcaa caacggtcta attggccgcc gacgtttgga     780

cagggcacaa aggttgaaat aaaggcggcc gcaactacca cccctgcccc tcggccgccg     840

actccggccc caaccatcgc aagccaaccc ctctccttgc gccccgaagc ttgccgcccg     900

gccgcgggtg gagccgtgca tacccggggg ctggactttg cctgcgatat ctacatttgg     960

gccccgctgg ccggcacttg cggcgtgctc ctgctgtcgc tggtcatcac cctttactgc    1020

aagaggggcc ggaagaagct gctttacatc ttcaagcagc cgttcatgcg gcccgtgcag    1080

acgactcagg aagaggacgg atgctcgtgc agattccctg aggaggaaga ggggggatgc    1140
```

```
gaactgcgcg tcaagttctc acggtccgcc gacgcccccg catatcaaca gggccagaat   1200

cagctctaca acgagctgaa cctgggaagg agagaggagt acgacgtgct ggacaagcga   1260

cgcggacgcg acccggagat gggggggaaa ccacggcgga aaaaccctca ggaaggactg   1320

tacaacgaac tccagaaaga caagatggcg gaagcctact cagaaatcgg gatgaaggga   1380

gagcggagga ggggaaaggg tcacgacggg ctgtaccagg gactgagcac cgccactaag   1440

gatacctacg atgccttgca tatgcaagca ctcccacccc gg                      1482
```

<210> SEQ ID NO 114
<211> LENGTH: 494
<212> TYPE: PRT
<213> ORGANISM: Artificial Sequence
<220> FEATURE:
<223> OTHER INFORMATION: LTG 2525 (hScFv aCD38 CD8 TM 4-1BB CD3 zeta)

<400> SEQUENCE: 114

```
Met Leu Leu Leu Val Thr Ser Leu Leu Leu Cys Glu Leu Pro His Pro
1               5                   10                  15

Ala Phe Leu Leu Ile Pro Glu Val Gln Leu Leu Glu Ser Gly Gly Gly
            20                  25                  30

Leu Val Gln Pro Gly Gly Ser Leu Arg Leu Ser Cys Ala Val Ser Gly
        35                  40                  45

Phe Thr Phe Asn Ser Phe Ala Met Ser Trp Val Arg Gln Ala Pro Gly
    50                  55                  60

Lys Gly Leu Glu Trp Val Ser Ala Ile Ser Gly Ser Gly Gly Gly Thr
65                  70                  75                  80

Tyr Tyr Ala Asp Ser Val Lys Gly Arg Phe Thr Ile Ser Arg Asp Asn
                85                  90                  95

Ser Lys Asn Thr Leu Tyr Leu Gln Met Asn Ser Leu Arg Ala Glu Asp
            100                 105                 110

Thr Ala Val Tyr Phe Cys Ala Lys Asp Lys Ile Leu Trp Phe Gly Glu
        115                 120                 125

Pro Val Phe Asp Tyr Trp Gly Gln Gly Thr Leu Val Thr Val Ser Ser
    130                 135                 140

Ala Ser Gly Gly Gly Gly Ser Gly Gly Gly Gly Ser Gly Gly Gly Gly
145                 150                 155                 160

Ser Glu Ile Val Leu Thr Gln Ser Pro Ala Thr Leu Ser Leu Ser Pro
                165                 170                 175

Gly Glu Arg Ala Thr Leu Ser Cys Arg Ala Ser Gln Ser Val Ser Ser
            180                 185                 190

Tyr Leu Ala Trp Tyr Gln Gln Lys Pro Gly Gln Ala Pro Arg Leu Leu
        195                 200                 205

Ile Tyr Asp Ala Ser Asn Arg Ala Thr Gly Ile Pro Ala Arg Phe Ser
    210                 215                 220

Gly Ser Gly Ser Gly Thr Asp Phe Thr Leu Thr Ile Ser Ser Leu Glu
225                 230                 235                 240

Pro Glu Asp Phe Ala Val Tyr Tyr Cys Gln Gln Arg Ser Asn Trp Pro
                245                 250                 255

Pro Thr Phe Gly Gln Gly Thr Lys Val Glu Ile Lys Ala Ala Ala Thr
            260                 265                 270

Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300
```

```
Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```

<210> SEQ ID NO 115
<211> LENGTH: 1482
<212> TYPE: DNA
<213> ORGANISM: Artificial Sequence
<220> FEATURE:
<223> OTHER INFORMATION: LTG 2526 (hScFv aCD38 CD8 TM 4-1BB CD3 zeta)

<400> SEQUENCE: 115

```
atgctgctgc tggtgaccag cctgctgctg tgcgaactgc cgcatccggc gtttctgctg     60

attccggaaa ttgttttgac tcagagtcct gcgacattga gcttgagtcc gggtgaacgg    120

gctactctta gttgccgcgc ctcacagtcc gtatcttcat acctcgcctg gtatcaacag    180

aagccggggc aggcccctcg cctgcttata tatgatgcca gcaatagagc tactggaata    240

cctgcccgat tttctgggtc tggaagtggg acggatttca cactgacaat atcttctctt    300

gagccggaag actttgccgt ctattactgc caacagcgct ctaactggcc gcccacgttt    360

ggtcagggaa caaaggtaga gataaagggg ggcggtggct ccggtggggg agggagcgga    420

ggaggtggtt ctgaagtcca gcttctcgaa tccggtgggg gtctggttca acctggaggt    480

agtctccgct tgtcctgtgc tgtctcaggg ttcacattta actcttttgc tatgtcttgg    540

gttcggcaag ctcctggcaa gggcctggag tgggtgtccg ctattagtgg ctccggaggc    600

ggcacgtact atgcagatag tgtgaagggc aggtttacta tttcccggga taactctaag    660

aacaccctgt acttgcagat gaatagtttg cgagccgaag acactgcagt gtatttttgc    720

gccaaggata aaatactctg gtttggcgag ccggtatttg actattgggg gcaaggcaca    780

cttgtcacag tatccagcgc ctccgcggcc gcaactacca cccctgcccc tcggccgccg    840

actccggccc caaccatcgc aagccaaccc ctctccttgc gccccgaagc ttgccgcccg    900

gccgcgggtg gagccgtgca tacccggggg ctggactttg cctgcgatat ctacatttgg    960
```

```
gccccgctgg ccggcacttg cggcgtgctc ctgctgtcgc tggtcatcac cctttactgc   1020

aagaggggcc ggaagaagct gctttacatc ttcaagcagc cgttcatgcg gcccgtgcag   1080

acgactcagg aagaggacgg atgctcgtgc agattccctg aggaggaaga gggggggatgc   1140

gaactgcgcg tcaagttctc acggtccgcc gacgcccccg catatcaaca gggccagaat   1200

cagctctaca acgagctgaa cctgggaagg agagaggagt acgacgtgct ggacaagcga   1260

cgcggacgcg acccggagat gggggggaaa ccacggcgga aaaaccctca ggaaggactg   1320

tacaacgaac tccagaaaga caagatggcg gaagcctact cagaaatcgg gatgaaggga   1380

gagcggagga ggggaaaggg tcacgacggg ctgtaccagg gactgagcac cgccactaag   1440

gatacctacg atgccttgca tatgcaagca ctcccacccc gg                       1482
```

<210> SEQ ID NO 116
<211> LENGTH: 494
<212> TYPE: PRT
<213> ORGANISM: Artificial Sequence
<220> FEATURE:
<223> OTHER INFORMATION: LTG 2526 (hScFv aCD38 CD8 TM 4-1BB CD3 zeta)

<400> SEQUENCE: 116

```
Met Leu Leu Leu Val Thr Ser Leu Leu Leu Cys Glu Leu Pro His Pro
1               5                   10                  15

Ala Phe Leu Leu Ile Pro Glu Ile Val Leu Thr Gln Ser Pro Ala Thr
            20                  25                  30

Leu Ser Leu Ser Pro Gly Glu Arg Ala Thr Leu Ser Cys Arg Ala Ser
        35                  40                  45

Gln Ser Val Ser Ser Tyr Leu Ala Trp Tyr Gln Gln Lys Pro Gly Gln
    50                  55                  60

Ala Pro Arg Leu Leu Ile Tyr Asp Ala Ser Asn Arg Ala Thr Gly Ile
65                  70                  75                  80

Pro Ala Arg Phe Ser Gly Ser Gly Ser Gly Thr Asp Phe Thr Leu Thr
                85                  90                  95

Ile Ser Ser Leu Glu Pro Glu Asp Phe Ala Val Tyr Tyr Cys Gln Gln
            100                 105                 110

Arg Ser Asn Trp Pro Pro Thr Phe Gly Gln Gly Thr Lys Val Glu Ile
        115                 120                 125

Lys Gly Gly Gly Gly Ser Gly Gly Gly Gly Ser Gly Gly Gly Gly Ser
    130                 135                 140

Glu Val Gln Leu Leu Glu Ser Gly Gly Gly Leu Val Gln Pro Gly Gly
145                 150                 155                 160

Ser Leu Arg Leu Ser Cys Ala Val Ser Gly Phe Thr Phe Asn Ser Phe
                165                 170                 175

Ala Met Ser Trp Val Arg Gln Ala Pro Gly Lys Gly Leu Glu Trp Val
            180                 185                 190

Ser Ala Ile Ser Gly Ser Gly Gly Gly Thr Tyr Tyr Ala Asp Ser Val
        195                 200                 205

Lys Gly Arg Phe Thr Ile Ser Arg Asp Asn Ser Lys Asn Thr Leu Tyr
    210                 215                 220

Leu Gln Met Asn Ser Leu Arg Ala Glu Asp Thr Ala Val Tyr Phe Cys
225                 230                 235                 240

Ala Lys Asp Lys Ile Leu Trp Phe Gly Glu Pro Val Phe Asp Tyr Trp
                245                 250                 255

Gly Gln Gly Thr Leu Val Thr Val Ser Ser Ala Ser Ala Ala Ala Thr
            260                 265                 270
```

-continued

```
Thr Thr Pro Ala Pro Arg Pro Pro Thr Pro Ala Pro Thr Ile Ala Ser
        275                 280                 285

Gln Pro Leu Ser Leu Arg Pro Glu Ala Cys Arg Pro Ala Ala Gly Gly
    290                 295                 300

Ala Val His Thr Arg Gly Leu Asp Phe Ala Cys Asp Ile Tyr Ile Trp
305                 310                 315                 320

Ala Pro Leu Ala Gly Thr Cys Gly Val Leu Leu Leu Ser Leu Val Ile
                325                 330                 335

Thr Leu Tyr Cys Lys Arg Gly Arg Lys Lys Leu Leu Tyr Ile Phe Lys
            340                 345                 350

Gln Pro Phe Met Arg Pro Val Gln Thr Thr Gln Glu Glu Asp Gly Cys
        355                 360                 365

Ser Cys Arg Phe Pro Glu Glu Glu Glu Gly Gly Cys Glu Leu Arg Val
    370                 375                 380

Lys Phe Ser Arg Ser Ala Asp Ala Pro Ala Tyr Gln Gln Gly Gln Asn
385                 390                 395                 400

Gln Leu Tyr Asn Glu Leu Asn Leu Gly Arg Arg Glu Glu Tyr Asp Val
                405                 410                 415

Leu Asp Lys Arg Arg Gly Arg Asp Pro Glu Met Gly Gly Lys Pro Arg
            420                 425                 430

Arg Lys Asn Pro Gln Glu Gly Leu Tyr Asn Glu Leu Gln Lys Asp Lys
        435                 440                 445

Met Ala Glu Ala Tyr Ser Glu Ile Gly Met Lys Gly Glu Arg Arg Arg
    450                 455                 460

Gly Lys Gly His Asp Gly Leu Tyr Gln Gly Leu Ser Thr Ala Thr Lys
465                 470                 475                 480

Asp Thr Tyr Asp Ala Leu His Met Gln Ala Leu Pro Pro Arg
                485                 490
```